US012807711B2

(12) United States Patent
Daniyan et al.

(10) Patent No.: US 12,807,711 B2
(45) Date of Patent: Nov. 24, 2026

(54) CHIMERIC ANTIGEN RECEPTORS WITH CD28 MUTATIONS AND USE THEREOF

(71) Applicant: MEMORIAL SLOAN-KETTERING CANCER CENTER, New York, NY (US)

(72) Inventors: Anthony Daniyan, Somers, NY (US); Renier J. Brentjens, Short Hills, NJ (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 935 days.

(21) Appl. No.: 17/817,735

(22) Filed: Aug. 5, 2022

(65) Prior Publication Data

US 2023/0051064 A1 Feb. 16, 2023

Related U.S. Application Data

(63) Continuation of application No. PCT/US2021/016713, filed on Feb. 5, 2021.

(60) Provisional application No. 62/970,401, filed on Feb. 5, 2020.

(51) Int. Cl.

| | |
|---|---|
| ***A61K 40/31*** | (2025.01) |
| ***A61K 40/11*** | (2025.01) |
| ***A61K 40/42*** | (2025.01) |
| ***A61P 35/00*** | (2006.01) |
| ***C07K 16/28*** | (2006.01) |
| ***C12N 5/0783*** | (2010.01) |
| ***C12N 15/63*** | (2006.01) |

(52) U.S. Cl.

CPC .......... *C07K 16/2818* (2013.01); *A61K 40/11* (2025.01); *A61K 40/31* (2025.01); *A61K 40/4211* (2025.01); *A61P 35/00* (2018.01); *C07K 16/2896* (2013.01); *C12N 5/0636* (2013.01); *C12N 5/0646* (2013.01); *C12N 15/63* (2013.01); *A61K 2239/22* (2023.05); *C07K 2317/622* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 5,525,503 A | 6/1996 | Rudd et al. | |
| 10,058,585 B2 | 8/2018 | Chaudhari et al. | |
| 2003/0105000 A1 | 6/2003 | Pero et al. | |
| 2013/0330335 A1 | 12/2013 | Bremel et al. | |
| 2018/0044399 A1 * | 2/2018 | Rajpal | C07K 14/70521 |
| 2019/0023764 A1 | 1/2019 | Wu et al. | |
| 2019/0389928 A1 | 12/2019 | Posey et al. | |

FOREIGN PATENT DOCUMENTS

| | | | |
|---|---|---|---|
| WO | WO 2017/176525 A1 | 10/2017 | |
| WO | WO-2018140725 A1 * | 8/2018 | A61P 35/00 |
| WO | WO 2019/010383 A1 | 1/2019 | |

OTHER PUBLICATIONS

Posey 2017 (Molecular Therapy, May 2017, 25:154, abstract 330, IDS).*

Kessels et al (PNAS, 2002, 99:8524-8529).*

Harada et al., "Novel Role of Phosphatidylinositol 3-Kinase in CD28-mediated Costimulation," The Journal of Biological Chemistry 276(12):9003-9008 (2001).

Kessels et al., "Specificity and affinity motifs for Grb2 SH2-ligand interactions," Proceedings of The National Academy of Sciences, 99(13):8524-8529 (2002).

Long et al., "4-1BB costimulation ameliorates T cell exhaustion induced by tonic signaling of chimeric antigen receptors," Nature Medicine, 21(6):581-590 (2015).

Posey et al., "Mixed Signals: Alteration of CD28 Signaling Motifs Improves Anti-Tumor Efficacy and Persistence of CAR T Cells," Molecular Therapy, 25(5S1):154 (2017).

International Search Report dated Jun. 3, 2021 in International Application No. PCT/US2021/016713.

* cited by examiner

*Primary Examiner* — Laura B Goddard

(74) *Attorney, Agent, or Firm* — Baker Botts L.L.P.

(57) ABSTRACT

The present disclosure provides methods and compositions for enhancing the immune response toward cancers and pathogens. It relates to chimeric antigen receptors (CARs) comprising a mutated CD28 intracellular motif, and cells comprising such CARs. The presently disclosed subject matter further relates to the use of said cells for treating diseases, e.g., for treating cancers.

28 Claims, 41 Drawing Sheets

Specification includes a Sequence Listing.

ah19h28hZ h19hYKNlhZ

Donor B

| | Etah19YKNlz (n=6) | Etah1928z (n=6) | Etah19hDEL (n=6) |
|---|---|---|---|
| Median survival | 31 | 23 | 18 |

| | |
|---|---|
| P value | <0.0001 |
| P value summary | **** |
| Are the survival curves sig different? | Yes |

| | Etah19hDEL (n=4) | Etah19h28Z(n=4) | Etah19hYENVhZ(n=5) | Etah19hYGGGhZ(n=4) |
|---|---|---|---|---|
| Median survival | 20.5 | 24 | 27 | Undefined |

| Etah19hYKNihZ(n=4) | Etah19hYKNLhZ(n=4) | Etah19hYMDMhZ(n=4) | Etah19hYSNVhZ(n=4) |
|---|---|---|---|
| Undefined | 20 | Undefined | 20.5 |

| | Etah19hDEL (n=4) | Etah19h28Z(n=4) | Etah19hYENVhZ(n=5) | Etah19hYGGGhZ(n=4) |
|---|---|---|---|---|
| Median survival | 20.5 | 24 | 27 | 63.5 |

| Etah19hYKNIhZ(n=4) | Etah19hYKNLhZ(n=4) | Etah19hYMDMhZ(n=4) | Etah19hYSNVhZ(n=4) |
|---|---|---|---|
| 40 | 20 | 63 | 20.5 |

ah19hYENVhZ

DA
Y21

Click # ED20191112125112_001 Comment: Cage 6
Tue, Nov 12, 2019 12:51:18 Time Point: 15s ah19hYMDMhZ

DA
Y21

Click # ED20191112130139_001 Comment: Cage 10
Tue, Nov 12, 2019 13:01:45 Time Point: 15s

| | Etah19hDEL, 5e5 (n=9) | Etah19h28Z, 5e5 (n=9) | Etah19hYMDMhZ, 5e5 (n=9) | Etah19hYKNihZ, 5e5 (n=9) |
|---|---|---|---|---|
| Median survival | 19 | 31 | 75 | 42 |

| Etah19hYGGGhZ, 5e5 (n=8) | Etah19hYENVhZ, 5e5 (n=8) | Etah19hYSNVhZ, 5e5 (n=8) |
|---|---|---|
| 52.5 | Undefined | 54.5 |

| | Etah19hDEL 2e5 (n=5) | Etah19hZ 2e5 (n=5) | Etah19h28hZ 2e5 (n=5) | Etah19hYKNIhZ 2e5 (n=5) |
|---|---|---|---|---|
| Median survival | 19 | 19 | 19 | 32 |

| Etah19hYMDMhZ 2e5 (n=5) | Etah19hYGGGhZ 2e5 (n=5) | Etah19hYENVhZ 2e5 (n=5) | Etah19hYSNVhZ 2e5 (n=5) |
|---|---|---|---|
| 45 | 51 | 25 | 67 |

CHIMERIC ANTIGEN RECEPTORS WITH CD28 MUTATIONS AND USE THEREOF

CROSS-REFERENCE TO RELATED APPLICATIONS

The present application is a continuation of International Patent Application No. PCT/US21/16713, filed Feb. 5, 2021, which claims priority to U.S. Provisional Patent Application No. 62/970,401, filed Feb. 5, 2020, the contents of each of which are incorporated by reference in their entireties, and to each of which priority is claimed.

SEQUENCE LISTING

The specification further incorporates by reference the Sequence Listing submitted herewith via EFS on Aug. 5, 2022. Pursuant to 37 C.F.R. § 1.52(e) (5), the Sequence Listing file, identified as 089339_0245.xml, is 113,939 bytes and was created on Aug. 4, 2022. The Sequence Listing, electronically filed herewith, does not extend beyond the scope of the specification and thus does not contain new matter.

1. TECHNICAL FIELD

The present disclosure provides methods and compositions for enhancing an immune response toward cancers and pathogens. It relates to chimeric antigen receptors (CARs) comprising a mutated CD28 intracellular motif, i.e., a mutated YMNM motif. The presently disclosed subject matter also provides cells comprising the CARs and compositions comprising the cells, and uses of the cells and compositions for treating diseases, e.g., for treating cancers.

2. BACKGROUND

Cell-based immunotherapy is a therapy with curative potential for the treatment of cancer. T cells and other immune cells may be modified to target tumor antigens through the introduction of genetic material coding for natural or modified T cell receptors (TCR) or synthetic receptors for antigen, termed Chimeric Antigen Receptors (CARs), specific to selected antigens. Patient-engineered CAR T cells have demonstrated remarkable efficacy against a range of liquid and solid malignancies.

CARs that are being used in clinic and are in preclinical development predominantly use co-stimulatory signaling domains such as CD28 or 4-1BB. CD28 is a transmembrane protein that plays a critical role in T cell activation via its role as a costimulatory molecule, and is an integral part of the CD28-based CAR construct. Persistence, especially functional persistence of these CARs has shown been to be associated with better outcomes. There is unmet need for improved CARs having enhanced proliferation and persistence, and/or with improved efficiency and activities as compared to the existing CARs.

3. SUMMARY OF THE INVENTION

The presently disclosed subject matter provides chimeric antigen receptors (CARs) comprising a mutated CD28 intracellular motif, i.e., a mutated YMNM motif.

The present disclosure provides chimeric antigen receptor (CAR) comprising an extracellular antigen-binding domain, a transmembrane domain, and an intracellular signaling domain comprising at least one co-stimulatory signaling domain that comprises a CD28 polypeptide comprising a mutated YMNM motif.

In certain embodiments, the CD28 polypeptide has reduced recruitment of a p85 subunit of a phosphoinositide 3-kinase (PI3K) as compared to a CD28 molecule comprising a native YMNM motif. In certain embodiments, a p85 subunit of a PI3K does not bind to the mutated YMNM motif. In certain embodiments, the mutated YMNM motif consists of the amino acid sequence set forth in YxNx (SEQ ID NO: 21), wherein x is not a methionine (M). In certain embodiments, the mutated YMNM motif consists of the amino acid sequence set forth in YENV (SEQ ID NO: 22), YSNV (SEQ ID NO: 23), YKNL (SEQ ID NO: 24), YENQ (SEQ ID NO: 25), YKNI (SEQ ID NO: 26), YINQ (SEQ ID NO: 27), YHNK (SEQ ID NO: 28), YVNQ (SEQ ID NO: 29), YLNP (SEQ ID NO: 30), YLNT (SEQ ID NO: 31), YDND (SEQ ID NO: 66), YENI (SEQ ID NO: 67), YENL (SEQ ID NO: 68), YKNQ (SEQ ID NO: 72), YKNV (SEQ ID NO: 73), or YANG (SEQ ID NO: 87) . . . . In certain embodiments, the mutated YMNM motif consists of the amino acid sequence set forth in YSNV (SEQ ID NO: 23), YENV (SEQ ID NO: 22), or YKNI (SEQ ID NO: 26). In certain embodiments, the mutated YMNM motif consists of the amino acid sequence set forth in YSNV (SEQ ID NO: 23). In certain embodiments, the mutated YMNM motif binds to growth factor receptor bound receptor 2 (Grb2) and/or Grb2-related adaptor downstream of Shc (GADS).

In certain embodiments, the mutated YMNM motif does not bind to Grb2 and/or GADS. In certain embodiments, the mutated YMNM motif consists of the amino acid sequence set forth in YMxM (SEQ ID NO: 20), wherein x is not an aspartic acid (N). In certain embodiments, the mutated YMNM motif consists of the amino acid sequence set forth in YMDM (SEQ ID NO: 32), YMPM (SEQ ID NO: 79), YMRM (SEQ ID NO: 37), or YMSM (SEQ ID NO: 80). In certain embodiments, the mutated YMNM motif consists of the amino acid sequence set forth in YMDM (SEQ ID NO: 32). In certain embodiments, the mutated YMNM motif consists of the amino acid sequence set forth in YbxM (SEQ ID NO: 33), wherein x is not an aspartic acid (N), and b is not a methionine (M). In certain embodiments, the mutated YMNM motif consists of the amino acid sequence set forth in YTHM (SEQ ID NO: 34), YVLM (SEQ ID NO: 35), YIAM (SEQ ID NO: 36), YVEM (SEQ ID NO: 83), YVKM (SEQ ID NO: 85), or YVPM (SEQ ID NO: 86). In certain embodiments, the mutated YMNM motif consists of the amino acid sequence set forth in YMxb (SEQ ID NO: 65), wherein x is not an aspartic acid (N), and b is not a methionine (M). In certain embodiments, the mutated YMNM motif consists of the amino acid sequence set forth in YMAP (SEQ ID NO: 77). In certain embodiments, a p85 subunit of a PI3K signaling binds to the mutated YMNM motif.

In certain embodiments, the mutated YMNM motif does not bind to Grb2 and/or GADS or a p85 subunit of a PI3K. In certain embodiments, the mutated YMNM motif consists of the amino acid sequence set forth in Ybxb (SEQ ID NO: 43), wherein x is not an aspartic acid (N), and b is not a methionine (M). In certain embodiments, the mutated YMNM motif consists of the amino acid sequence set forth in YGGG (SEQ ID NO: 44), YAAA (SEQ ID NO: 45), YFFF (SEQ ID NO: 46)), YETV (SEQ ID NO: 69), YQQQ (SEQ ID NO: 70), YHAE (SEQ ID NO: 71), YLDL (SEQ ID NO: 74), YLIP (SEQ ID NO: 75), YLRV (SEQ ID NO: 76), YTAV (SEQ ID NO: 82), or YVHV (SEQ ID NO: 84).

In certain embodiments, the mutated YMNM motif consists of the amino acid sequence set forth in YGGG (SEQ ID NO: 44).

In certain embodiments, the mutated YMNM motif is capable of modulating PI3K signaling by limiting the number of methionine residues that can bind to a p85 subunit of PI3K. In certain embodiments, the mutated YMNM motif consists of the amino acid sequence set forth in YMNx (SEQ ID NO: 38) or YxNM (SEQ ID NO: 39), wherein x is not a methionine (M). In certain embodiments, the mutated YMNM motif consists of the amino acid sequence set forth in YMNV (SEQ ID NO: 40), YENM (SEQ ID NO: 41), and YMNQ (SEQ ID NO: 42), YMNL (SEQ ID NO: 78), or YSNM (SEQ ID NO: 81).

In certain embodiments, the extracellular antigen-binding domain binds to an antigen. In certain embodiments, the antigen is a tumor antigen or a pathogen antigen. In certain embodiments, the antigen is a tumor antigen. In certain embodiments, the tumor antigen is selected from the group consisting of CD19, mesothelin, AXL, TIM3, HVEM, MUC16, MUC1, CA1X, CEA, CD8, CD7, CD10, CD20, CD22, CD30, CLL1, CD33, CD34, CD38, CD41, CD44, CD49f, CD56, CD70, CD74, CD99, CD123, CD133, CD138, EGP-2, EGP-40, EpCAM, Erb-B (e.g., Eerb-B2, Erb-B3, Erb-B4), FBP, Fetal acetylcholine receptor, folate receptor-α, GD2, GD3, HER-2, hTERT, IL-13R-α2, κ-light chain, KDR, LeY, L1 cell adhesion molecule, MAGE-A1, ERBB2, MAGEA3, CT83 (also known as KK-LC-1), p53, MART1,GP100, Proteinase3 (PR1), Tyrosinase, Survivin, hTERT, EphA2, NKG2D ligands, NY-ESO-1, oncofetal antigen (h5T4), PSCA, PSMA, ROR1, TAG-72, VEGF-R2, WT-1, BCMA, CD44V6, NKCS1, EGF1R, EGFR-VIII, ADGRE2, CCR1, LILRB2, PRAME, HPV E6 oncoprotein, and HPV E7 oncoprotein. In certain embodiments, the tumor antigen is CD19.

In certain embodiments, the mutated YMNM motif consists of the amino acid sequence set forth in YMDM (SEQ ID NO: 32). In certain embodiments, the extracellular antigen-binding domain binds to CD19. In certain embodiments, the CAR comprises the amino acid sequence set forth in SEQ ID NO: 51.

In certain embodiments, the mutated YMNM motif consists of the amino acid sequence set forth in YKNI (SEQ ID NO: 26). In certain embodiments, the extracellular antigen-binding domain binds to CD19. In certain embodiments, the CAR comprises the amino acid sequence set forth in SEQ ID NO: 55.

In certain embodiments, the mutated YMNM motif consists of the amino acid sequence set forth in YENV (SEQ ID NO: 22). In certain embodiments, the extracellular antigen-binding domain binds to CD19. In certain embodiments, the CAR comprises the amino acid sequence set forth in SEQ ID NO: 53.

In certain embodiments, the mutated YMNM motif consists of the amino acid sequence set forth in YSNV (SEQ ID NO: 64). In certain embodiments, the extracellular antigen-binding domain binds to CD19. In certain embodiments, the CAR comprises the amino acid sequence set forth in SEQ ID NO: 57.

In certain embodiments, the mutated YMNM motif consists of the amino acid sequence set forth in YGGG (SEQ ID NO: 63). In certain embodiments, the extracellular antigen-binding domain binds to CD19. In certain embodiments, the CAR comprises the amino acid sequence set forth in SEQ ID NO: 61.

The presently disclosed subject matter also provides cells comprising a CAR described herein. In certain embodiments, the cell is an immunoresponsive cell. In certain embodiments, the cell is a cell of the lymphoid lineage or a cell of the myeloid lineage. In certain embodiments, the cell is selected from the group consisting of T cells, Natural Killer (NK) cells, and stem cells from which lymphoid cells may be differentiated. In certain embodiments, the cell is a T cell. In certain embodiments, the T cell is selected from the group consisting of a cytotoxic T lymphocyte (CTL), a γδ T cell, a tumor-infiltrating lymphocyte (TIL), a regulatory T cell, a Natural Killer T (NKT) cell, and a tumor-reactive lymphocyte.

Furthermore, the presently discloses subject matter provides compositions comprising a cell described herein. In certain embodiments, the composition is a pharmaceutical composition that further comprises a pharmaceutically acceptable excipient. In certain embodiments, the composition is for treating and/or preventing a neoplasm, and/or a pathogen infection.

The presently discloses subject matter further provides methods of reducing tumor burden in a subject. In certain embodiments, the method comprises administering to the subject a cell described herein or a composition described herein. In certain embodiments, the method reduces the number of tumor cells, reduces tumor size, and/or eradicates the tumor in the subject.

The presently discloses subject matter further provides methods of treating and/or preventing a neoplasm. In certain embodiments, the method comprises administering to the subject a cell described herein or a composition described herein.

The presently discloses subject matter further provides methods of lengthening survival of a subject having a neoplasm. In certain embodiments, the method comprises administering to the subject a cell described herein or a composition described herein.

In certain embodiments, the neoplasm and/or tumor is selected from the group consisting of B cell leukemia, B cell lymphoma, acute lymphoblastic leukemia (ALL), chronic lymphocytic leukemia (CLL), non-Hodgkin's lymphoma, Burkitt lymphoma, acute myeloid leukemia (AML) and Mixed-phenotype acute leukemia (MPAL).

The presently discloses subject matter further provides methods for producing an antigen-specific cell. In certain embodiments, the method comprises introducing into a cell a nucleic acid sequence encoding a CAR described herein. In certain embodiments, the nucleic acid sequence is present on a vector. In certain embodiments, the vector is a retroviral vector.

In addition, the presently discloses subject matter provides nucleic acid molecules encoding CARs described herein. In certain embodiments, the nucleic acid molecule comprises the nucleotide sequence set forth in SEQ ID NO: 52, SEQ ID NO: 54, SEQ ID NO: 56, or SEQ ID NO: 58. The presently discloses subject matter further provides vectors comprising the nucleic acid molecules described herein. In certain embodiments, the vector is a y-retroviral rector.

The presently discloses subject matter further provides host cells expressing the nucleic acid molecule described herein. In certain embodiments, the host cell is a T cell.

Furthermore, the presently discloses subject matter kits comprising a CAR described herein, a cell described herein, a composition described herein, a nucleic acid molecule described herein, or a vector described herein. In certain embodiments, the kit further comprises written instructions for treating and/or preventing a neoplasm and/or a pathogen infection.

4. BRIEF DESCRIPTION OF THE DRAWINGS

Figure 3A:
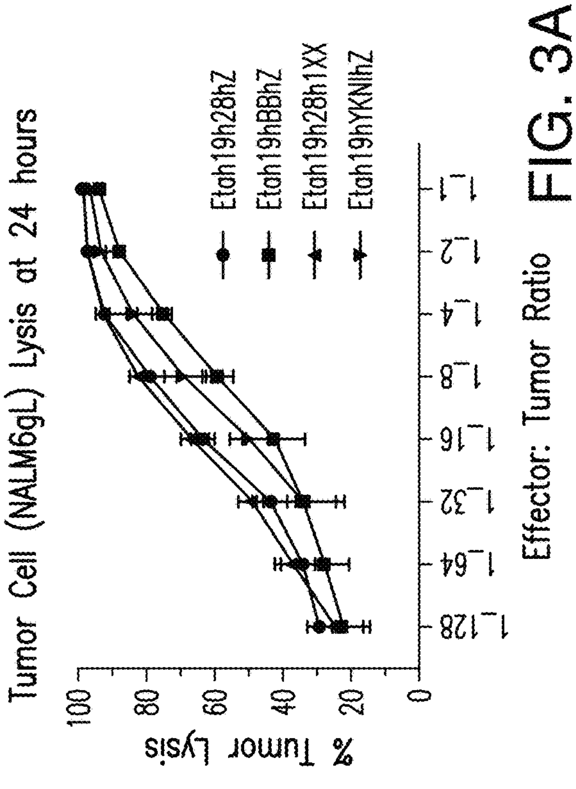
Figure 3B:
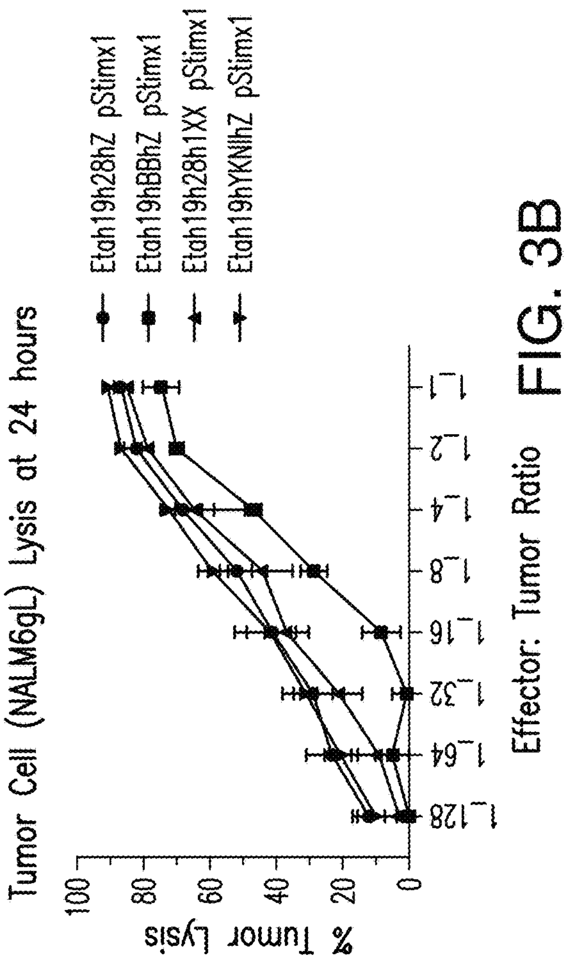
Figure 3C:
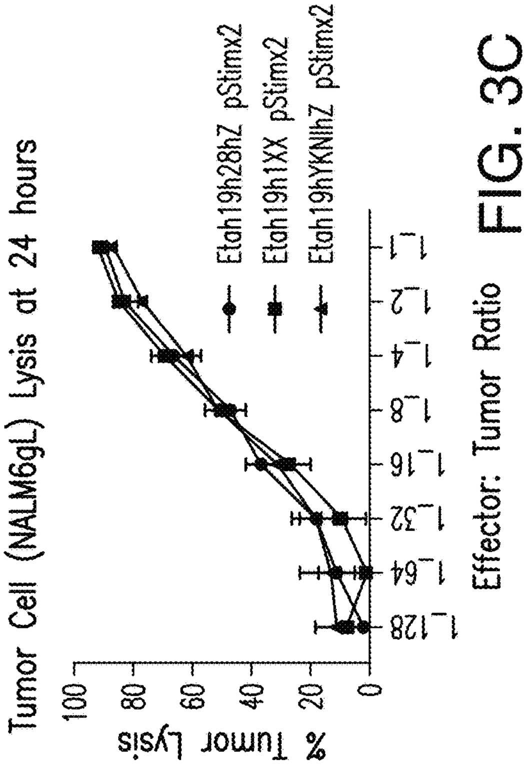
Figure 3D:
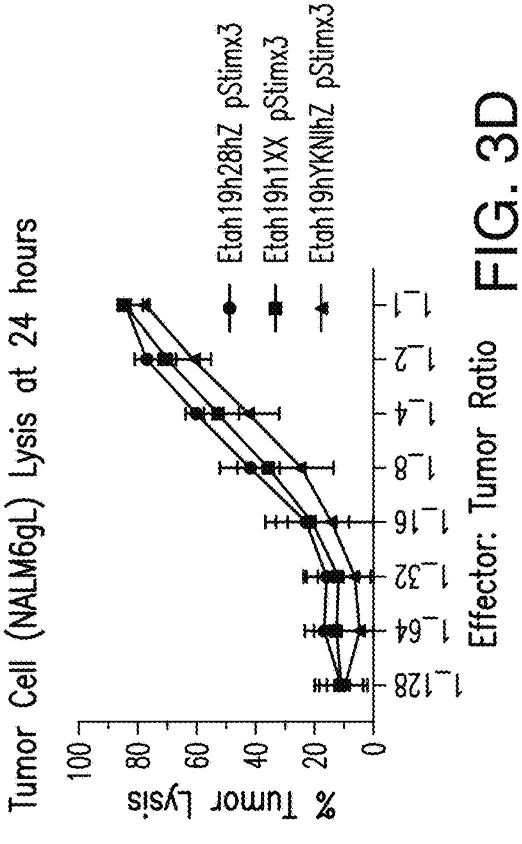

FIGS. 3A-3D show that CD28-YKNI mutant CAR T cells had potent killing capacity in vitro, which was comparable to certain CAR T cells (YKNI is SEQ ID NO: 26). Human CD19-targeted CAR T cells expressing a truncated EGFR domain (Etah 19) were cocultured with CD19+ NALM6 cells expressing GFP-ffLuciferase (NALM6gL) at different effector: tumor ratios. Tumor cell lysis (relative to a non-signaling CAR T cell) was measured by bioluminescence 24 hours later. h28Z: CD28-based+CD3Z signaling domain; hBBZ: 4-1BB-based+CD3Z signaling domain; h28h1XX: CD28-based+CD3Z signaling domain with mutated ITAM 2 and ITAM 3; hYKNIZ: mutated CD28-based (YMNM->YKNI)+CD3Z signaling domain. pStimx #refers to post-stimulation, where the number indicates the number of prior stimulations (SEQ ID NOs: 19 and 26, left to right respectively). FIG. 3A shows tumor cell lysis results of post manufacture. FIG. 3B shows tumor cell lysis results of post 1 stimulation. FIG. 3C shows tumor cell lysis results of post 2 stimulations. FIG. 3D shows tumor cell lysis results of post 4 stimulations.

Figure 4A:
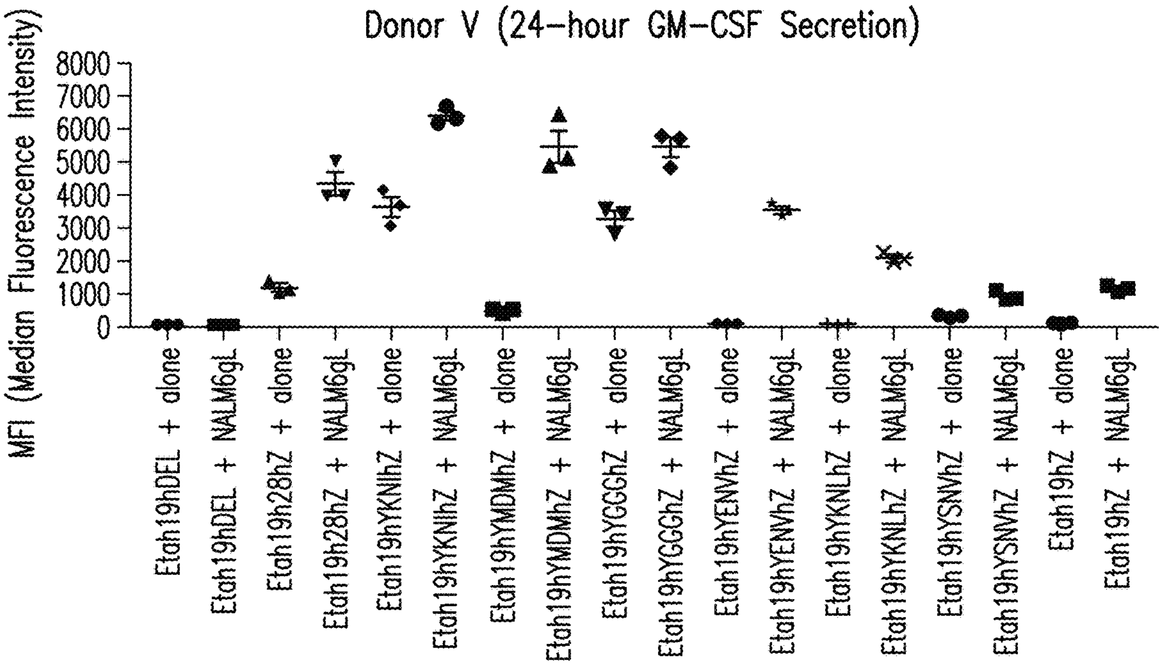
Figure 4B:
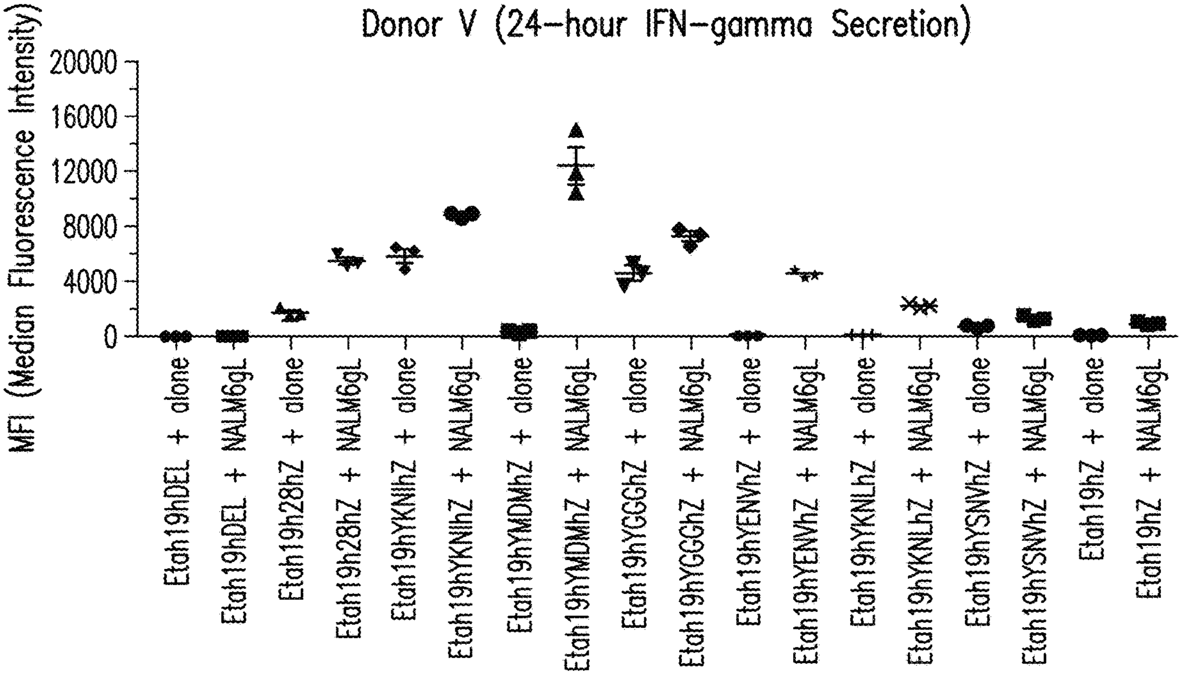
Figure 4C:
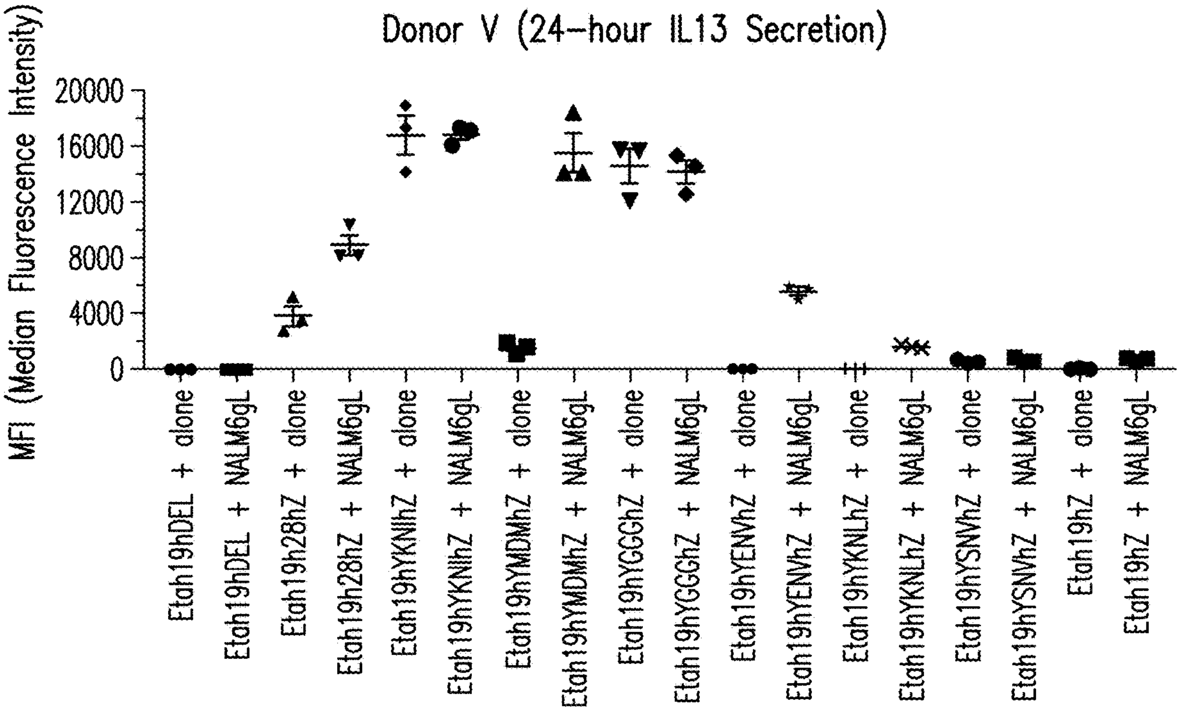
Figure 4D:
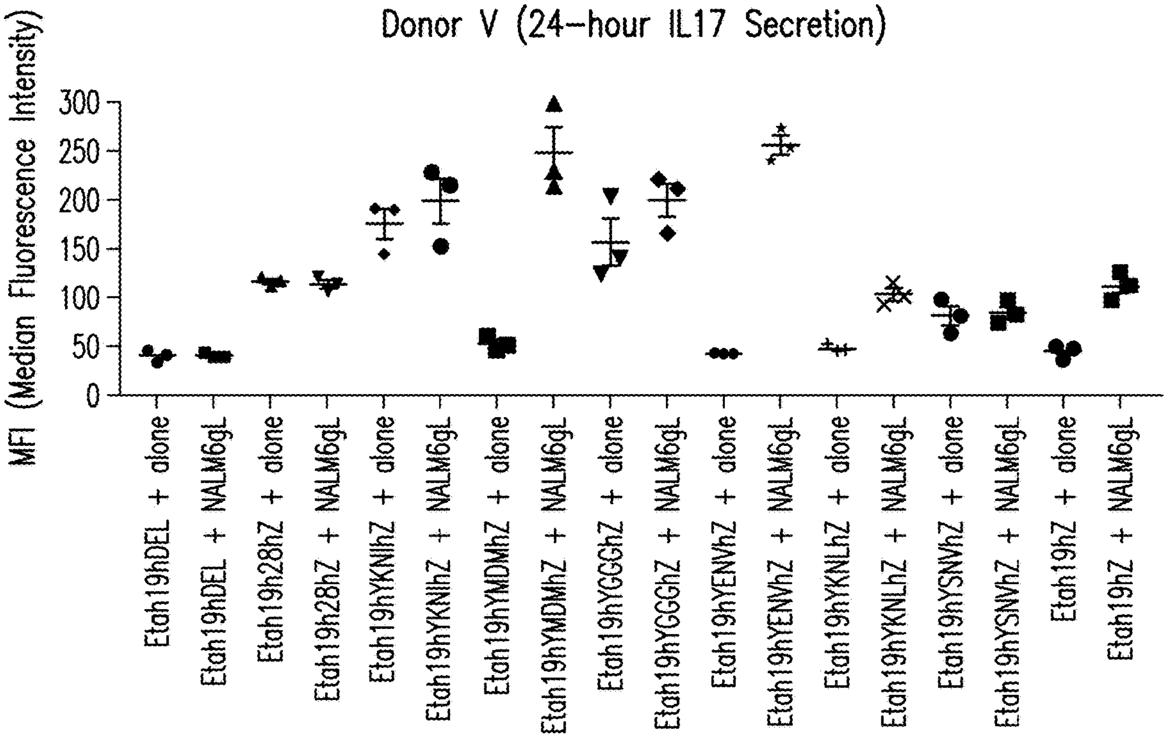
Figure 4E:
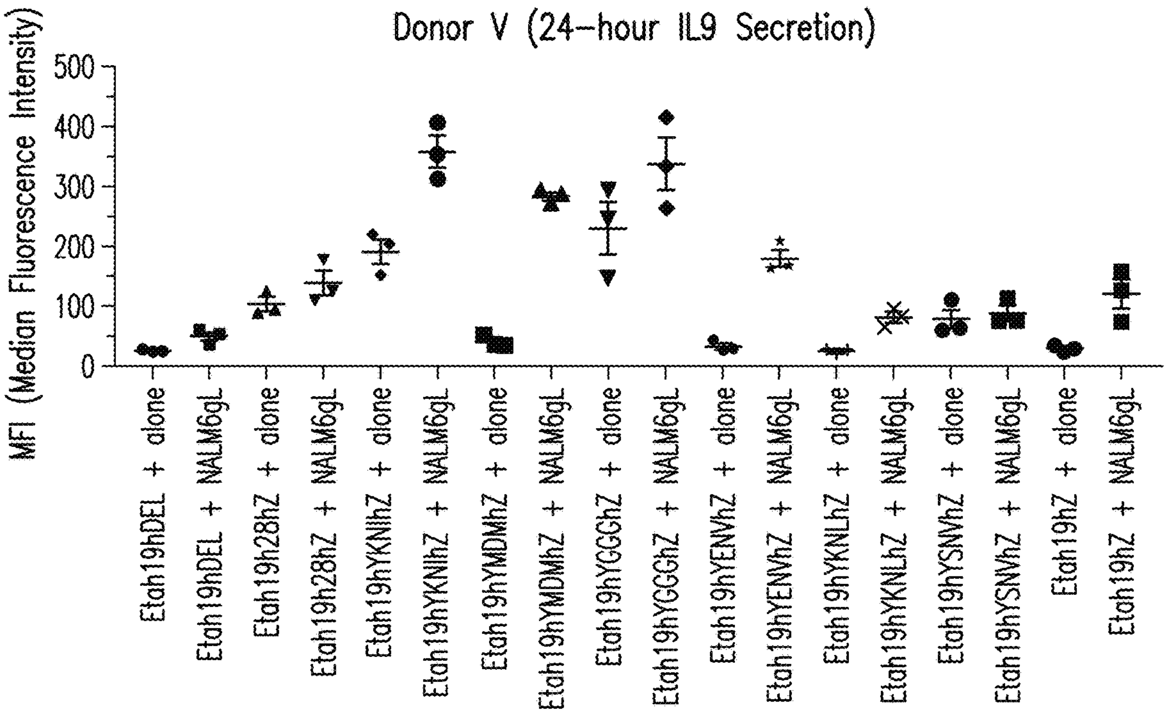
Figure 4F:
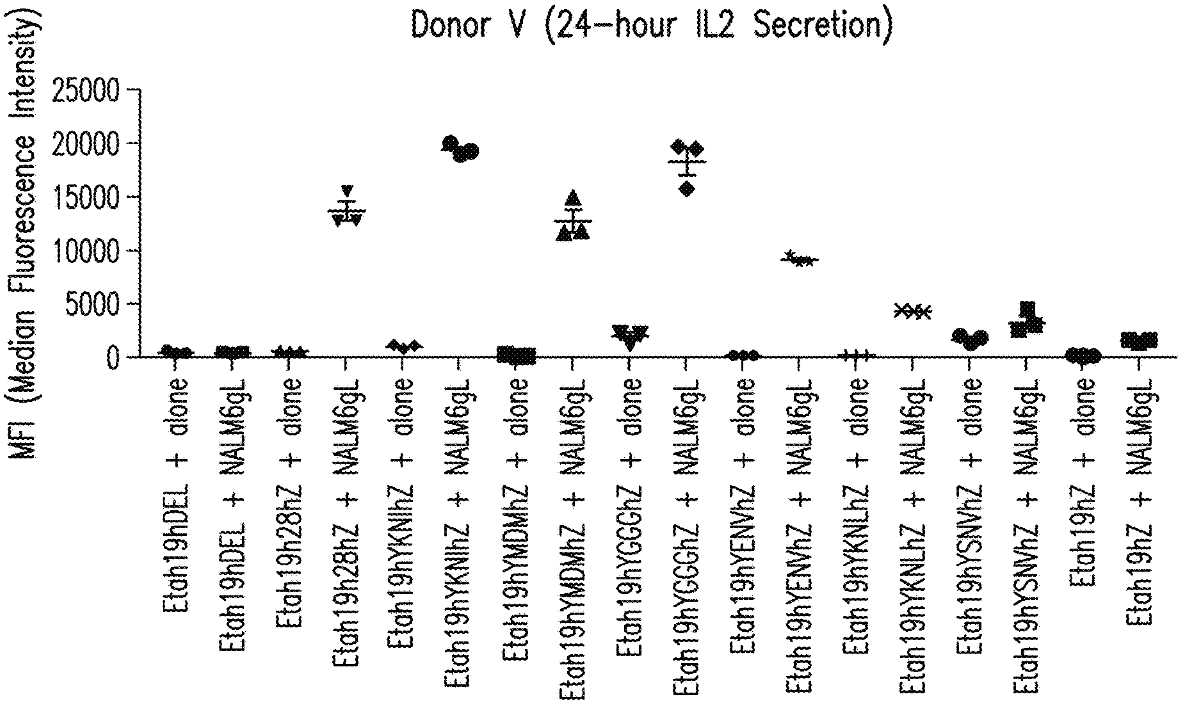
Figure 4G:
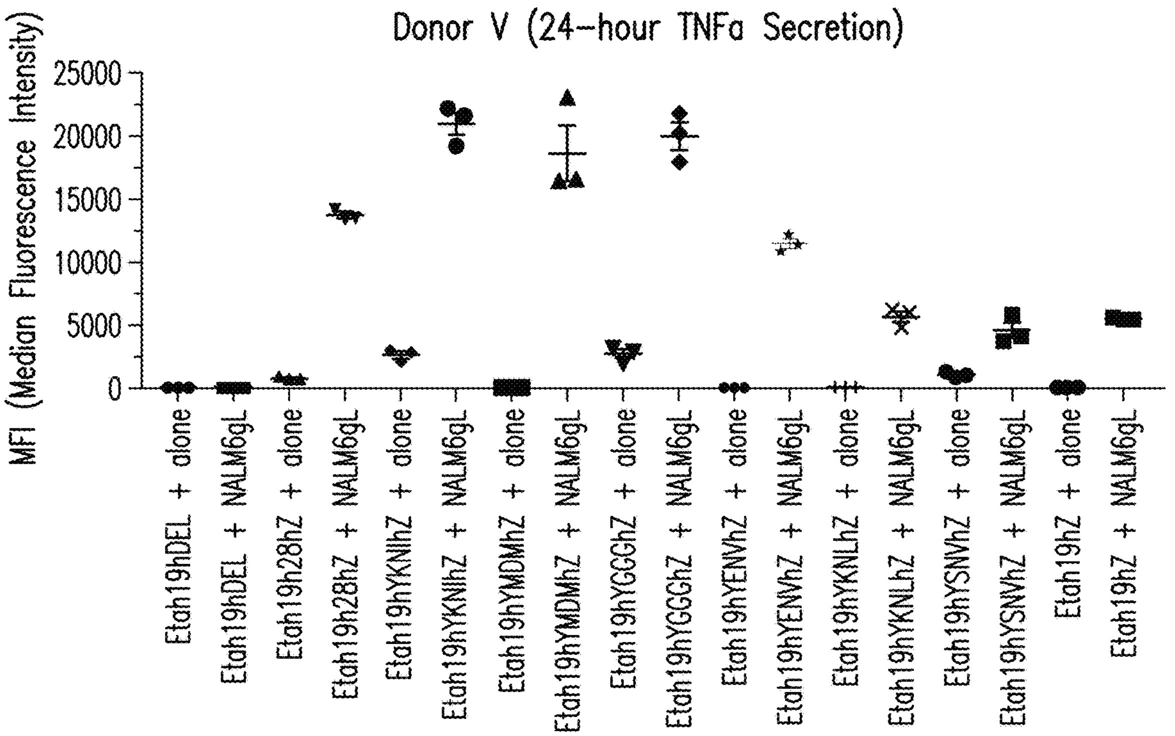
Figure 4H:
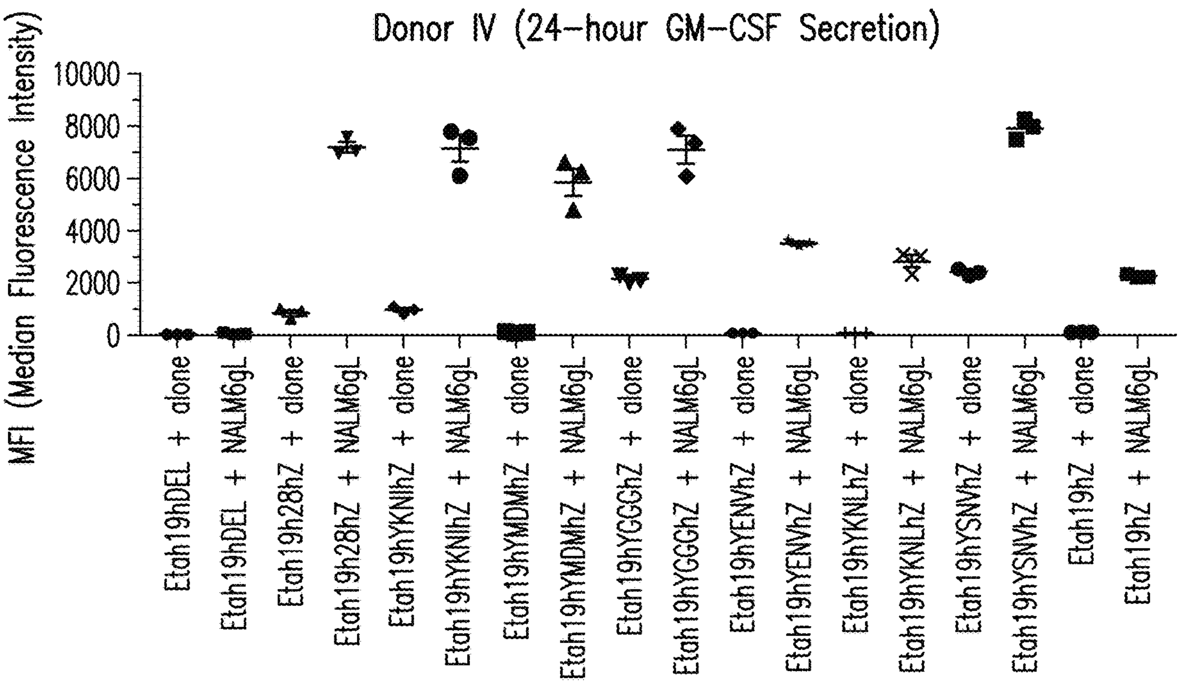
Figure 4I:
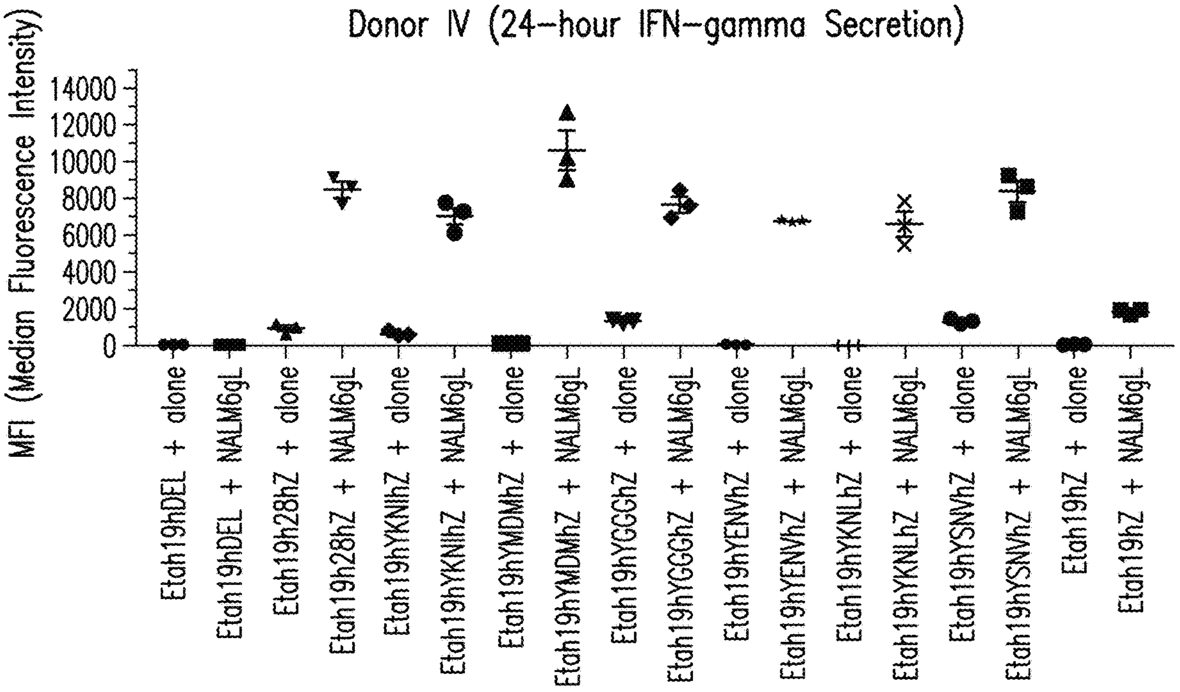
Figure 4J:
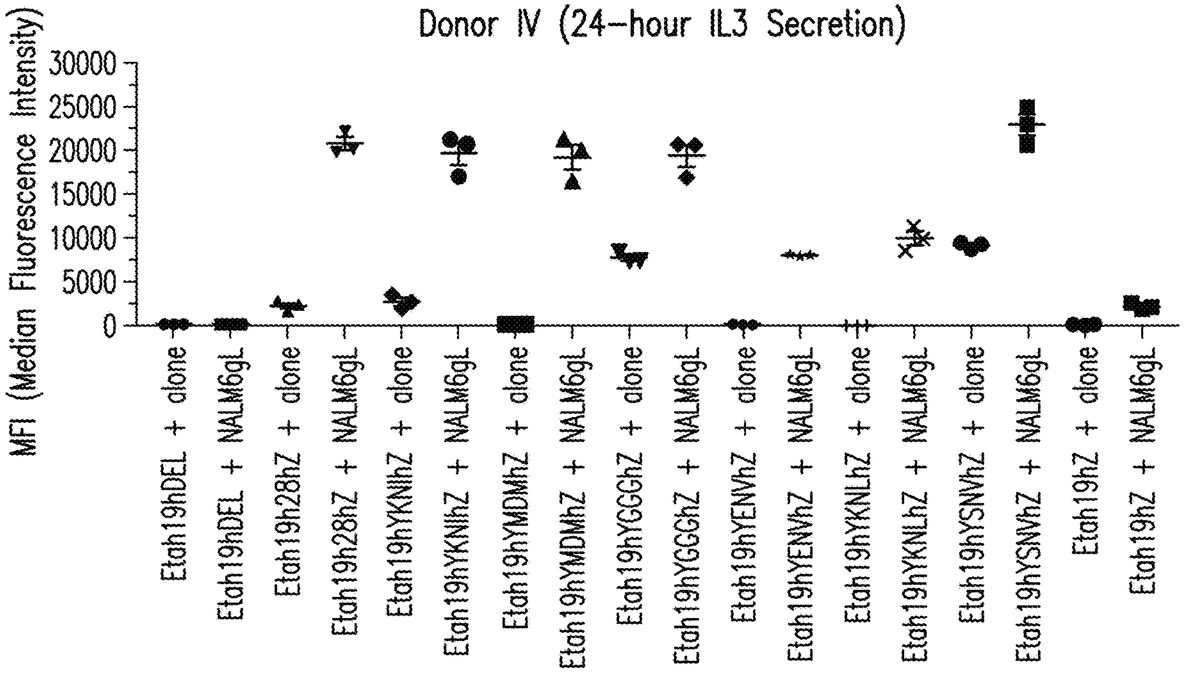
Figure 4K:
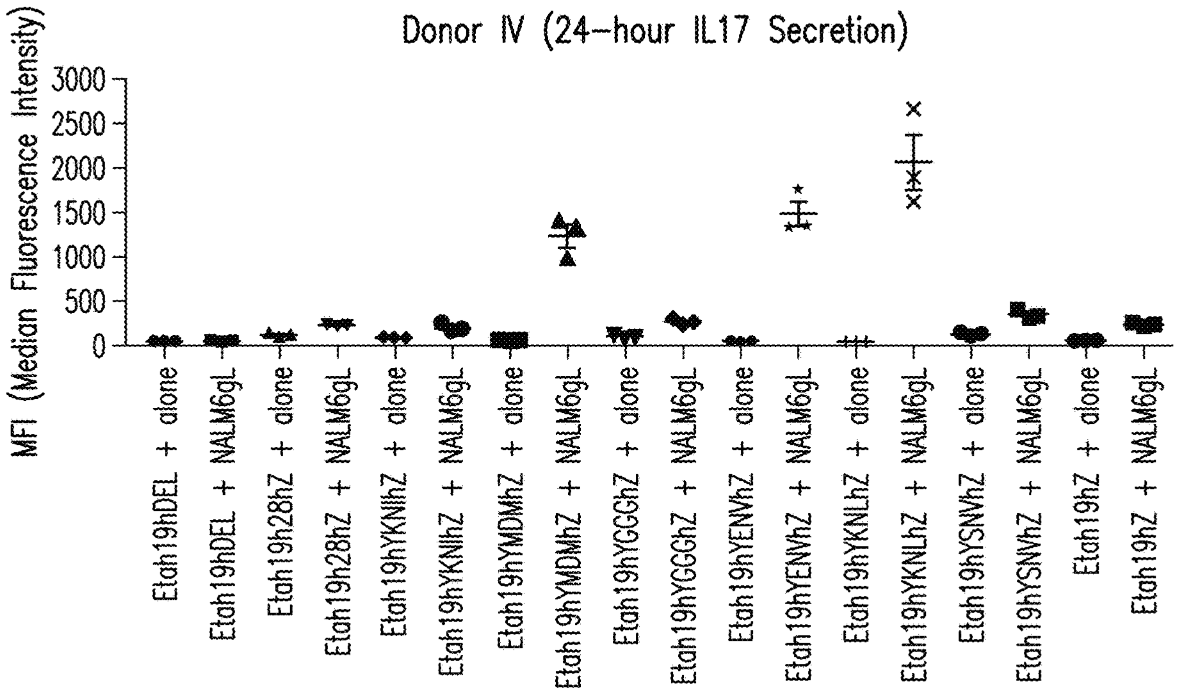
Figure 4L:
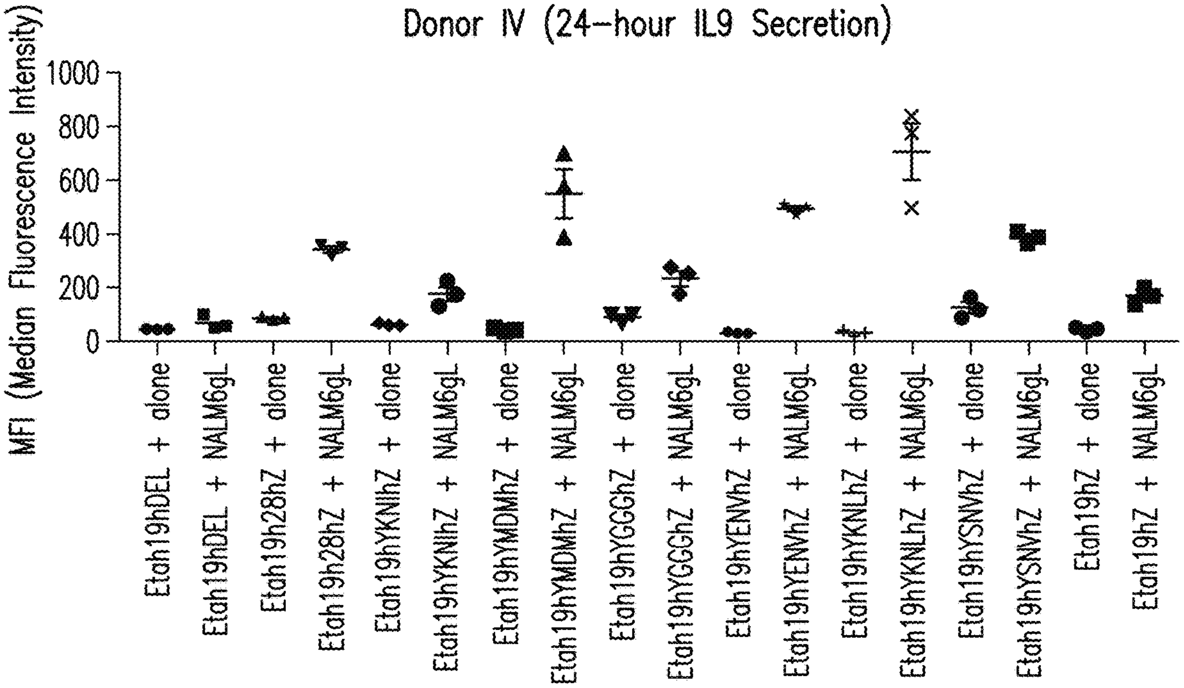
Figure 4M:
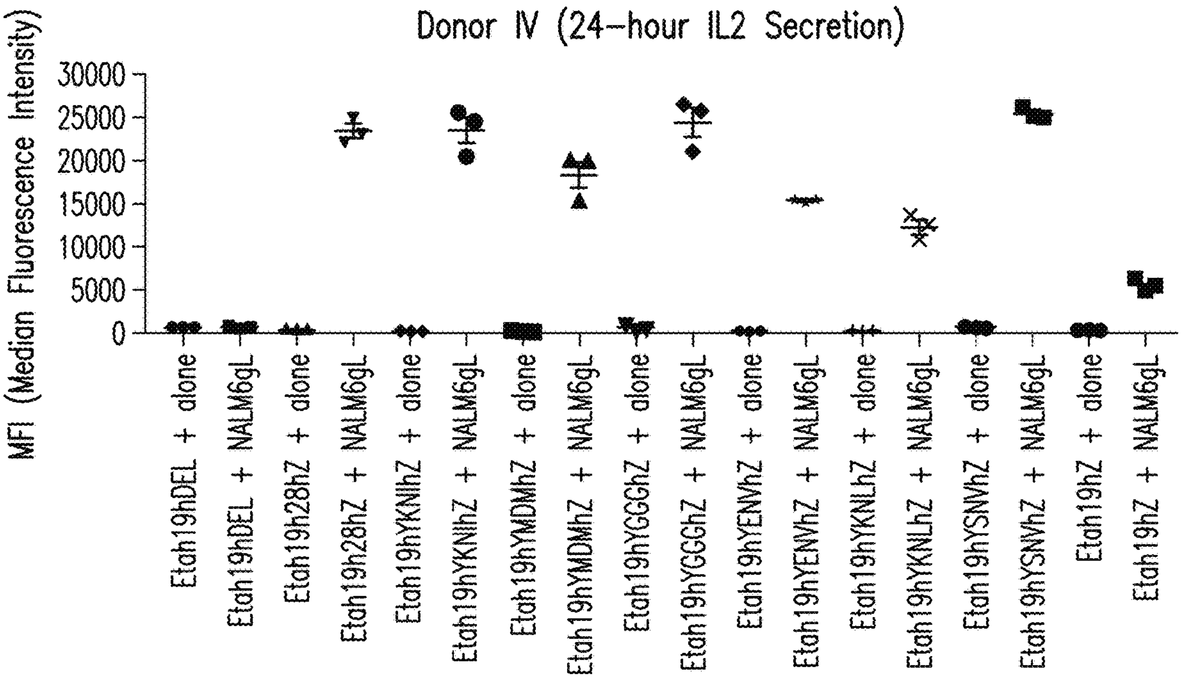
Figure 4N:
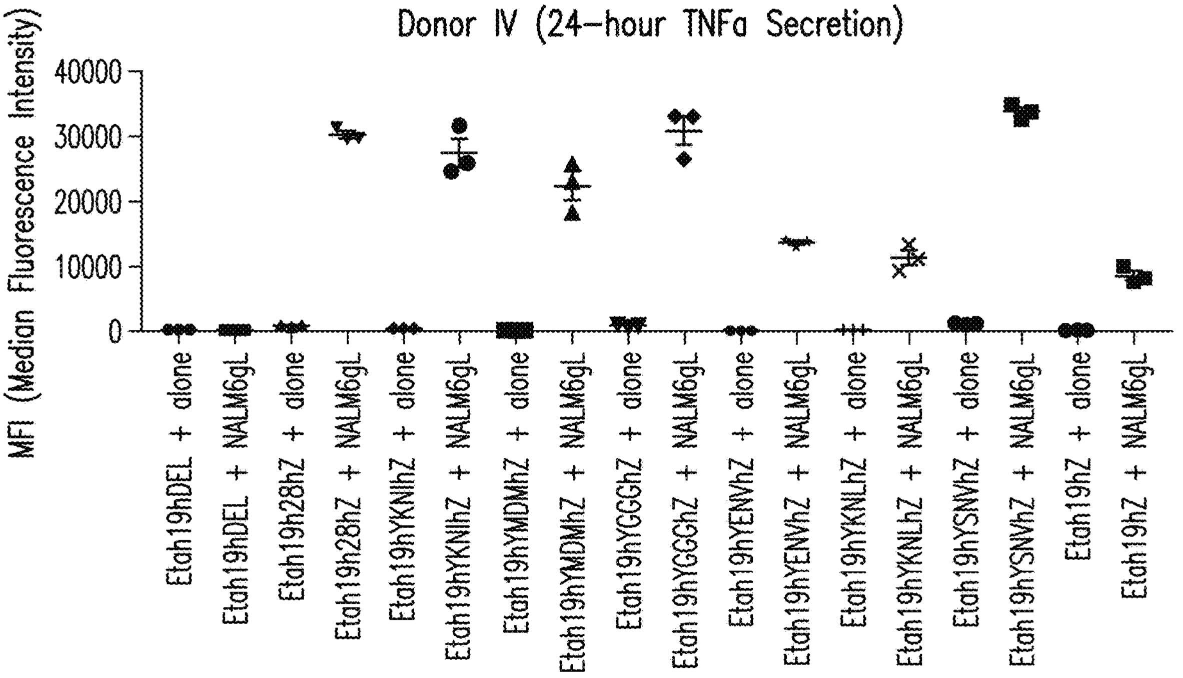

FIGS. 4A-4N show that mutant CD28 CAR T cells demonstrated a divergent pro-inflammatory cytokine secretion profile. Human CD19-targeted CAR T cells were cultured ALONE cocultured with CD19+ NALM6 cells at an effector: tumor ratio of 1:1. 24 hours later, supernatant was collected and cytokines were measured utilizing a bead-based multiplex assay. FIGS. 4A-4G show the cytokines profile from donor V, and FIGS. 4H-4N show the cytokine profile from donor IV. (FIG. 4A, 4H) GMCSF; (FIGS. 4B, 4I) IFN-γ; (FIGS. 4C, 4J) IL-13; (FIGS. 4D-4K) IL-17; (FIGS. 4E-4L) IL-9; (FIGS. 4F-4M) IL-2; (FIGS. 4G-4N) TNF-α.

Figure 5:
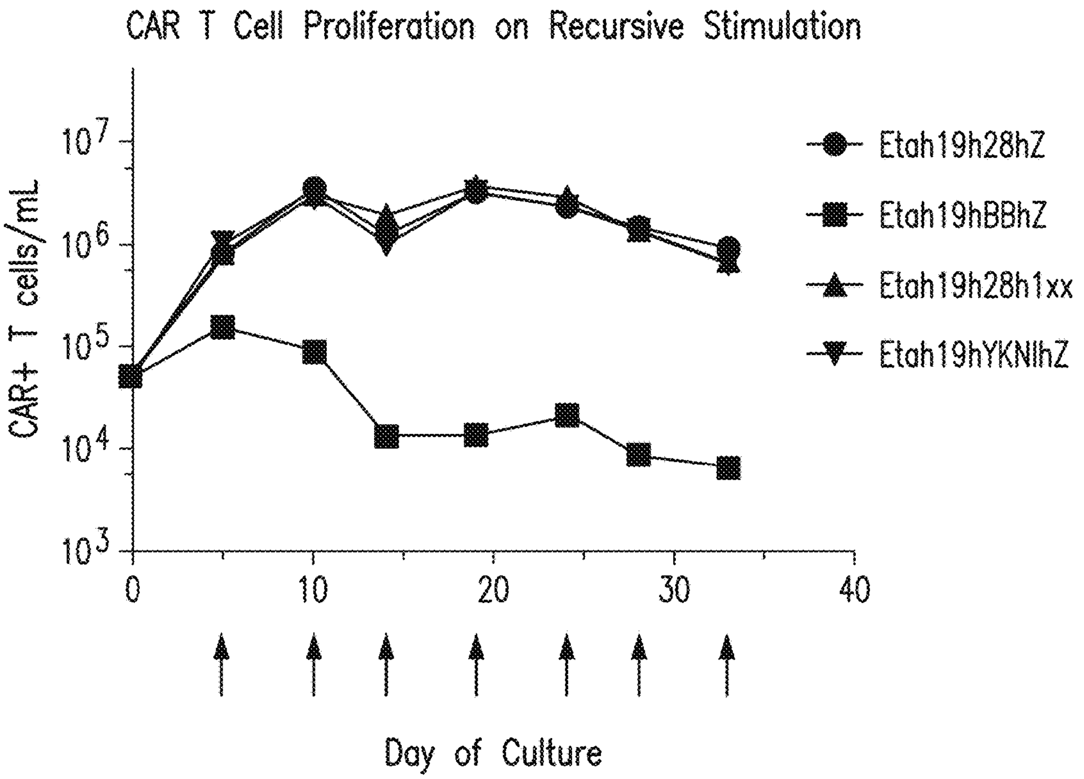

FIG. 5 shows that CD28-YKNI mutant CAR T cells had no quantitative differences in proliferation in response to repeated antigen exposure. Human CD19-targeted CAR T cells were cocultured with NALM6 at an E:T ratio of 1:5 and at a concentration of 50,000 CAR T cells/mL. Roughly every 5 days, CAR T cells were counted and characterized by flow cytometry, and the starting number of tumor cells were added back into the culture (indicated by arrows).

Figure 6:
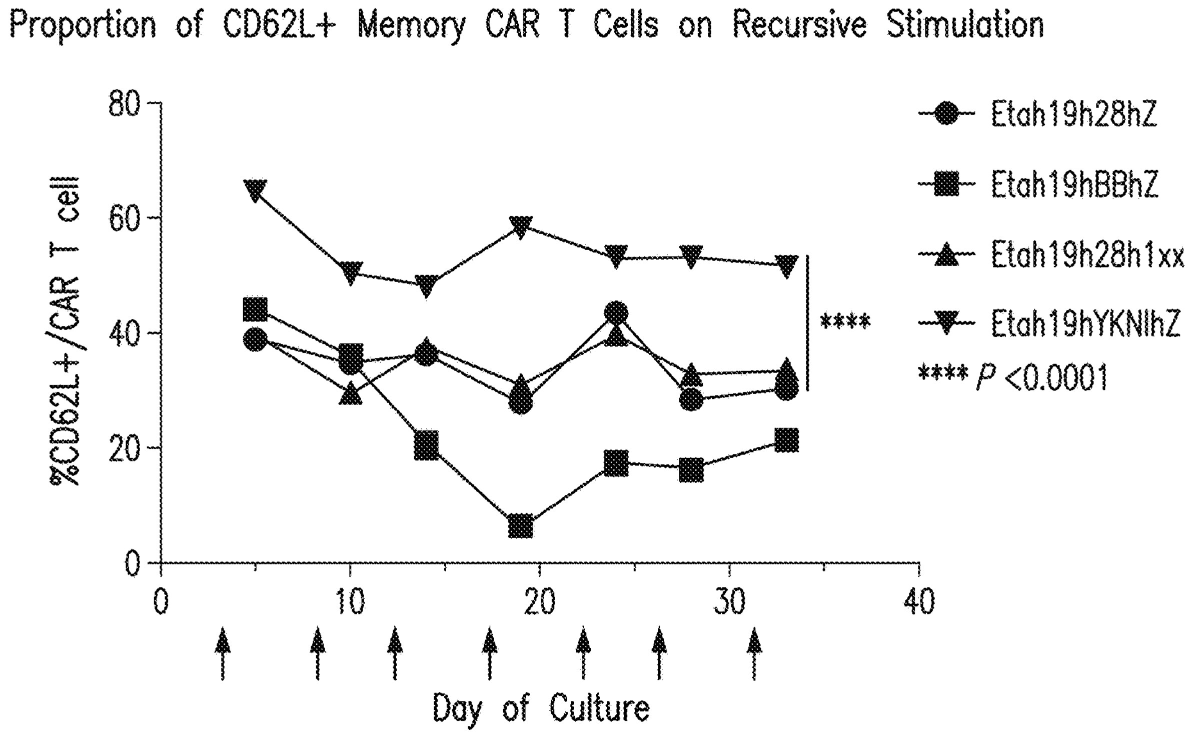

FIG. 6 shows that CD28-YKNI mutant CAR T cells retained a memory phenotype in the context of repeated antigen encounter in comparison to CD28 and CD28-1xx CAR T cells. Human CD19-targeted CAR T cells were cocultured with NALM6 at an E:T ratio of 1:5 and at a concentration of 50,000 CAR T cells/mL. Roughly every 5 days, CAR T cells were counted and characterized by flow cytometry for memory phenotype (CD62L+), and the starting number of NALM6 tumor cells were added back into the culture (indicated by arrows).

Figure 7:
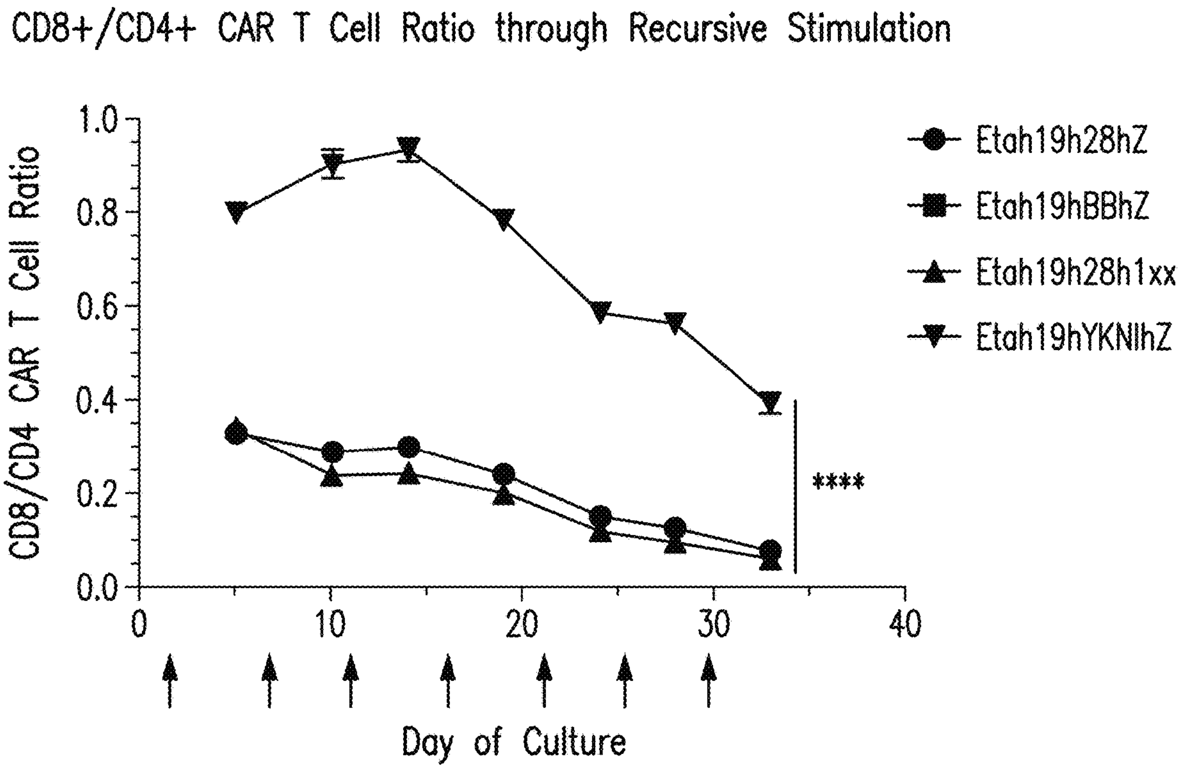

FIG. 7 shows that CD28-YKNI mutant CAR T cells retained a relatively balanced CD8: CD4 ratio in the context of repeated antigen encounter in comparison to CD28 and CD28-1xx CAR T cells. Human CD19-targeted CAR T cells were cocultured with NALM6 at an ET ratio of 1:5 and at a concentration of 50,000 CAR T cells/mL. Roughly every 5 days, CAR T cells were counted and characterized by flow cytometry for CD4/CD8 distribution, and the starting number of NALM6 tumor cells were added back into the culture (indicated by arrows).

Figure 8:
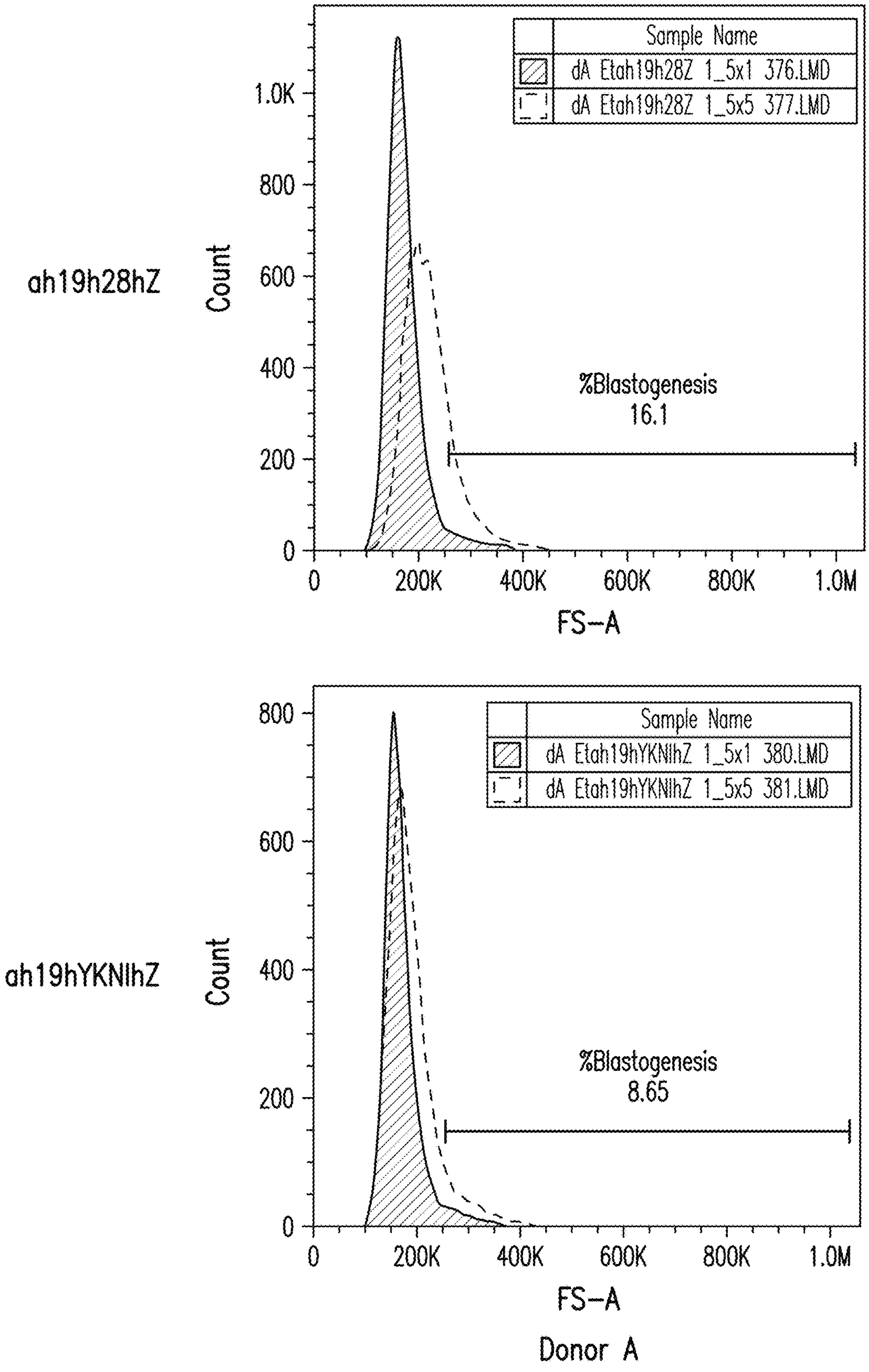
Figure 8:
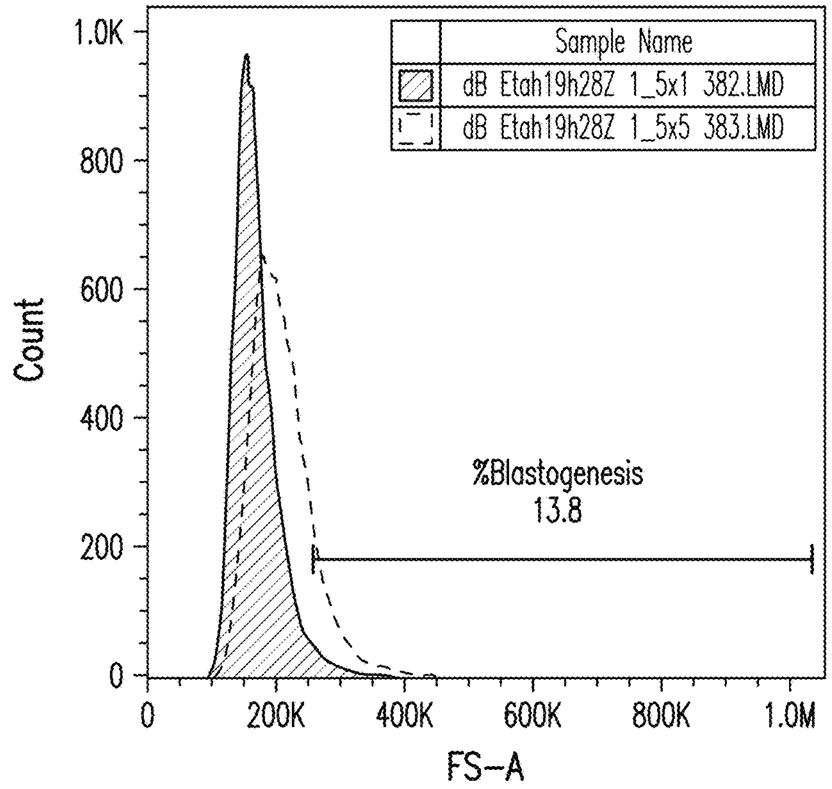
Figure 8:
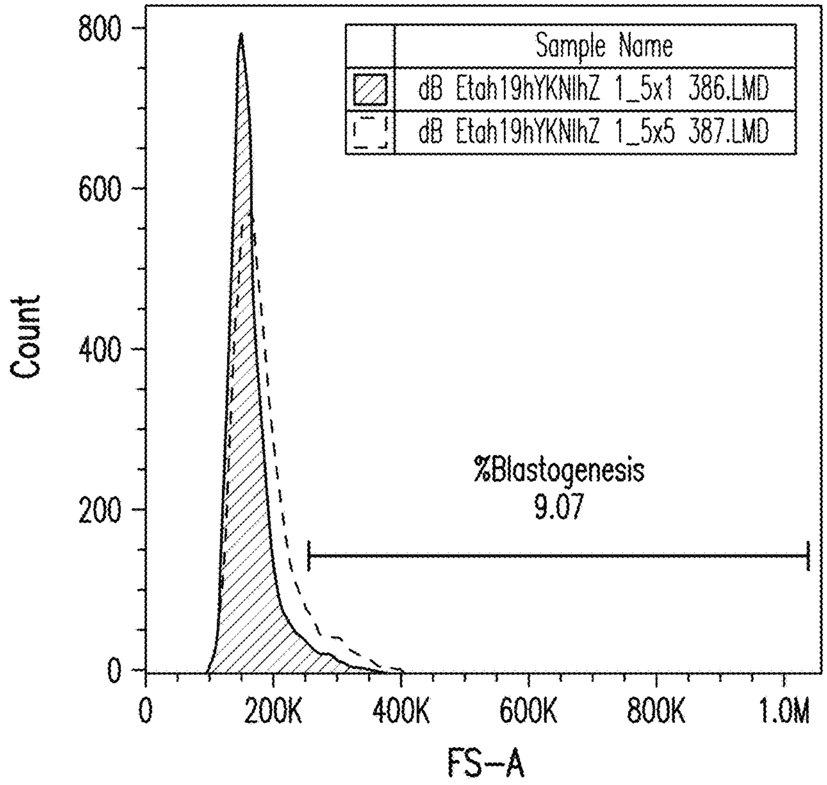

FIG. 8 shows that CD28-YKNI mutant CAR T cells demonstrated lower blastogenesis post single or multiple activations. CAR T cells were cocultured with NALM6gL at an initial E: T of 1:5 (1 stimulation, in blue). In parallel, CAR T cells were repeatedly stimulated with the same amount of tumor for a total of 5 stimulations (with 1 stimulation every 12 hours; in red). Approximately ten days post initiation of coculture, size/blastogenesis (as assessed by forward scatter) was assessed by flow cytometry.

Figure 9A:
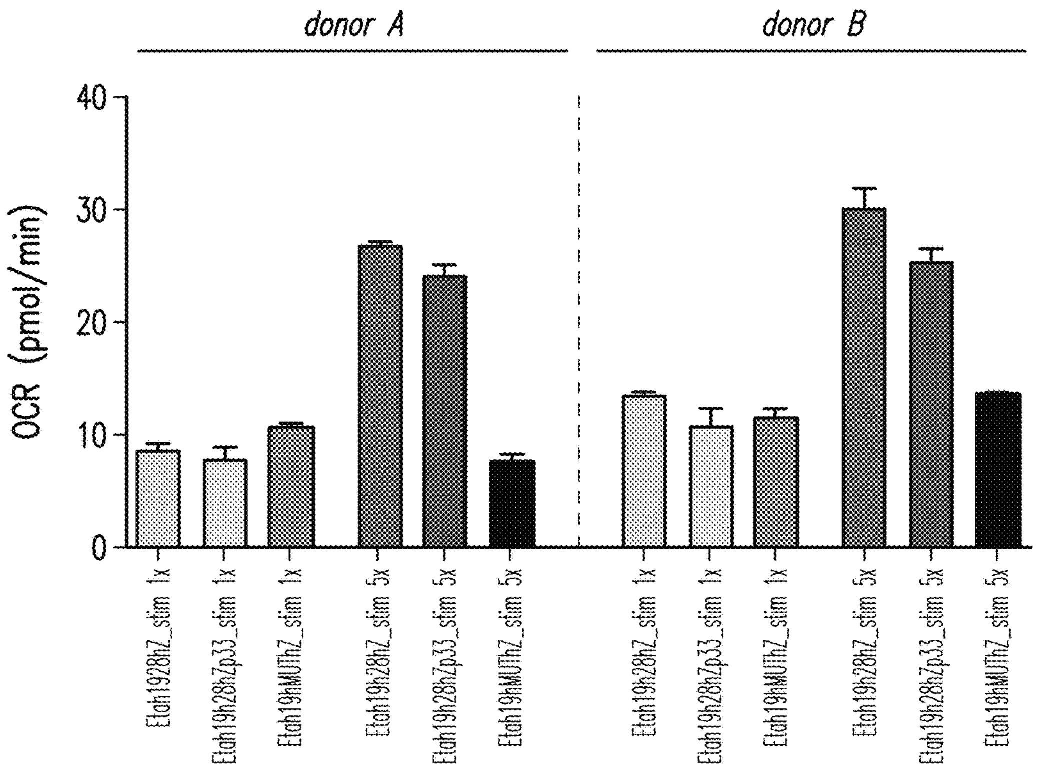
Figure 9B:
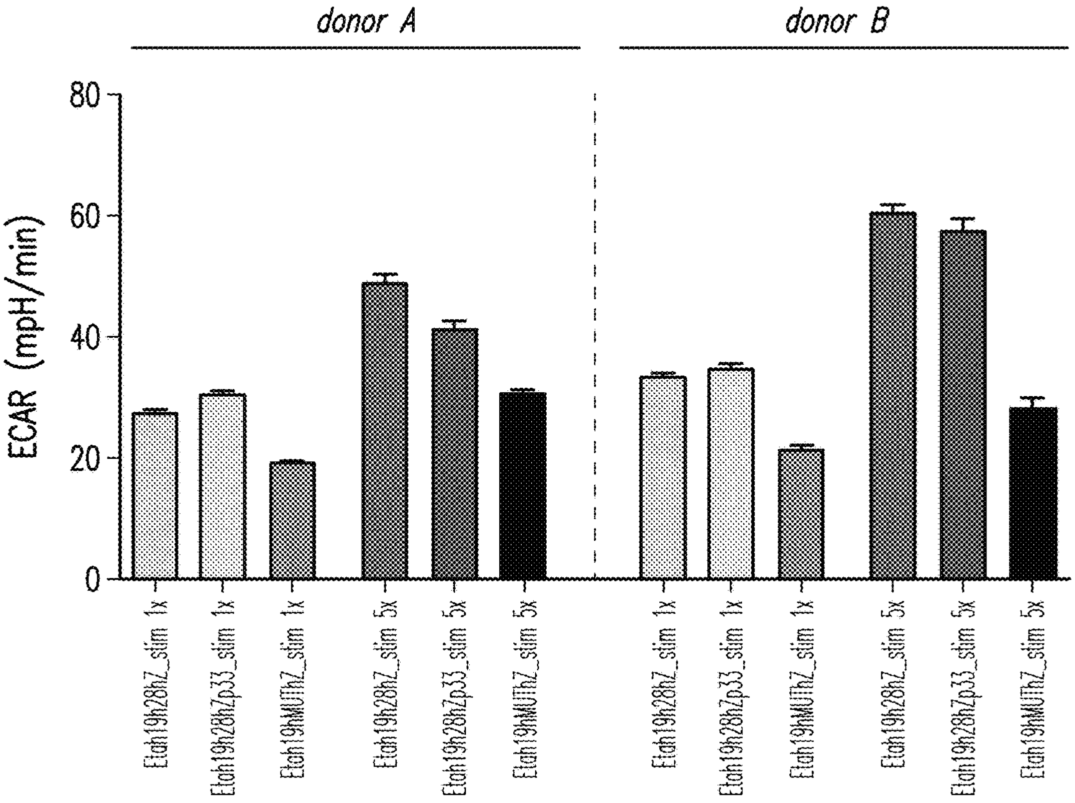

FIGS. 9A-9B show metabolic profile that was measured in CAR T cells nine days after single or multiple stimulations in donors A and B. Oxygen consumption rate (OCR) (FIG. 9A) and extracellular acidification rate (ECAR) (FIG. 9B) were measured in stimulated CAR T cells.

Figure 10A:
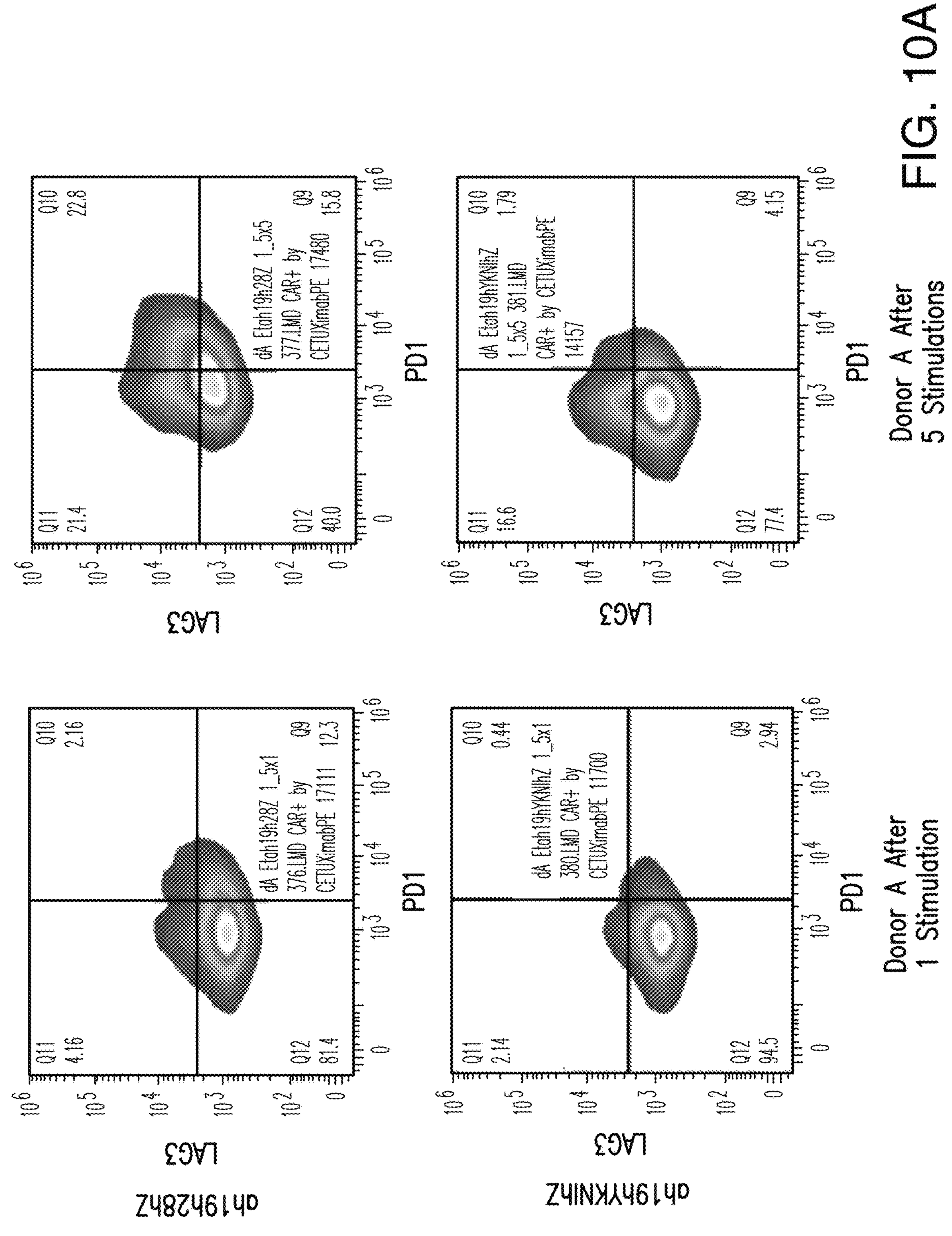
Figure 10A:
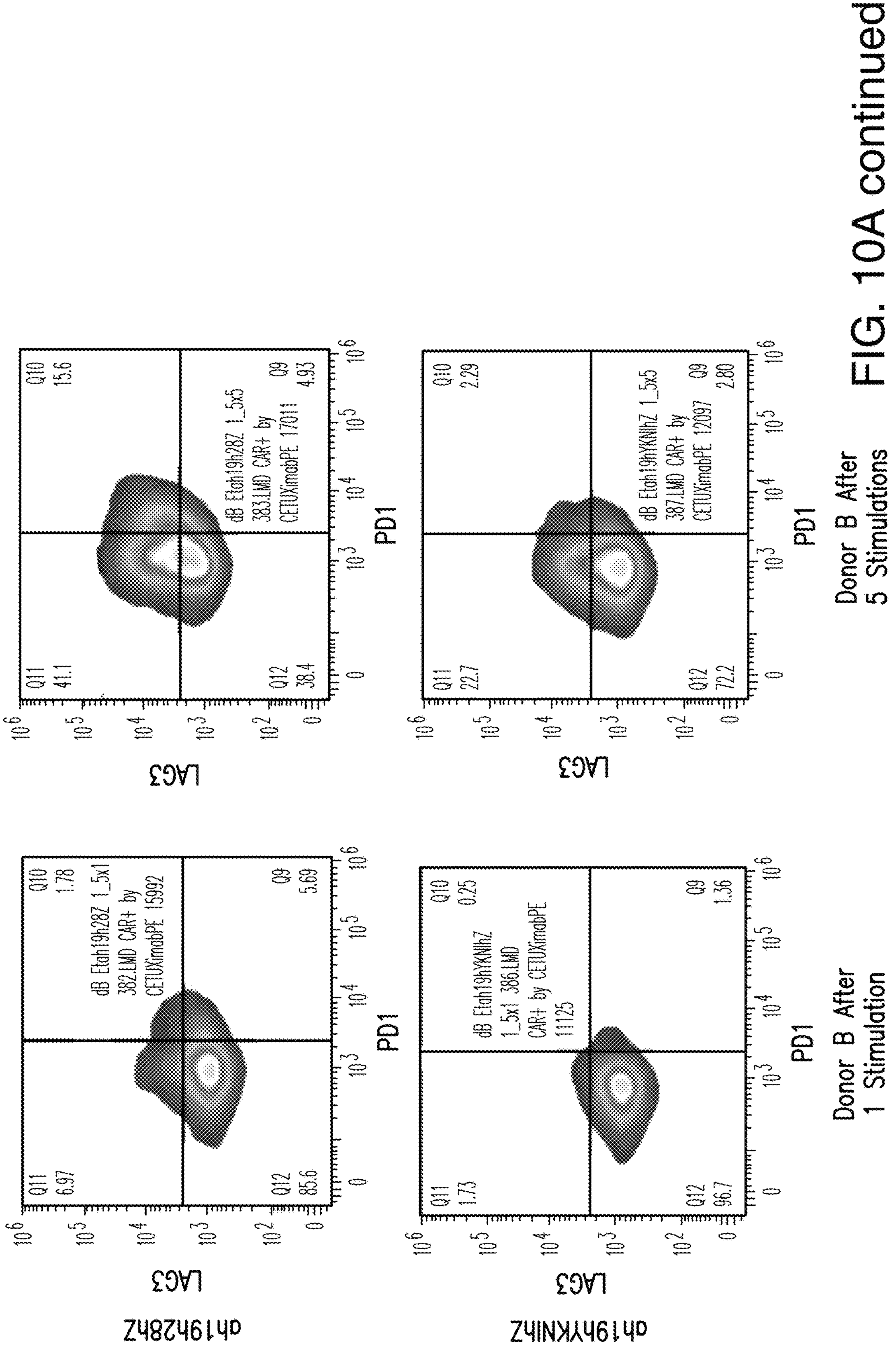
Figure 10B:
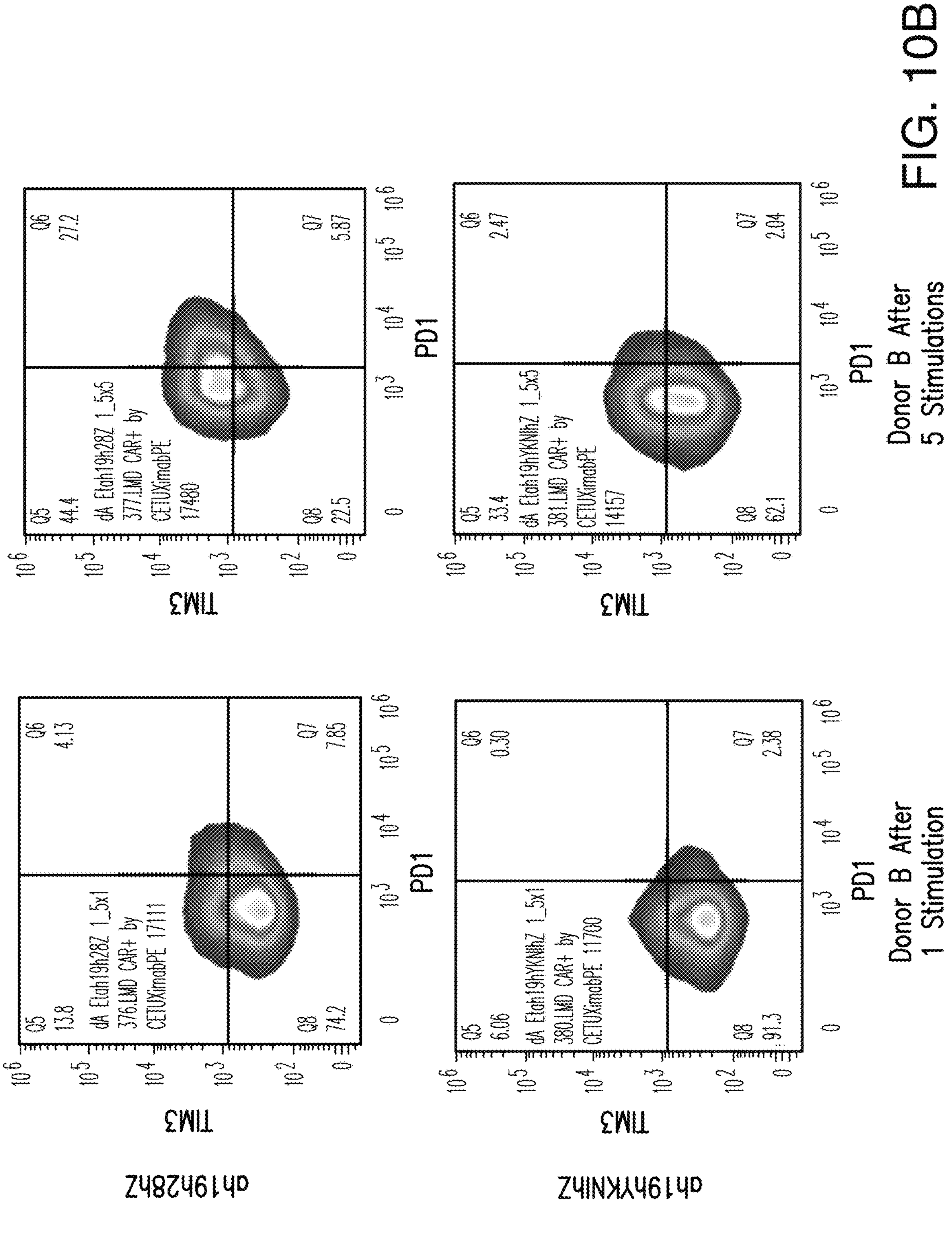
Figure 10B:
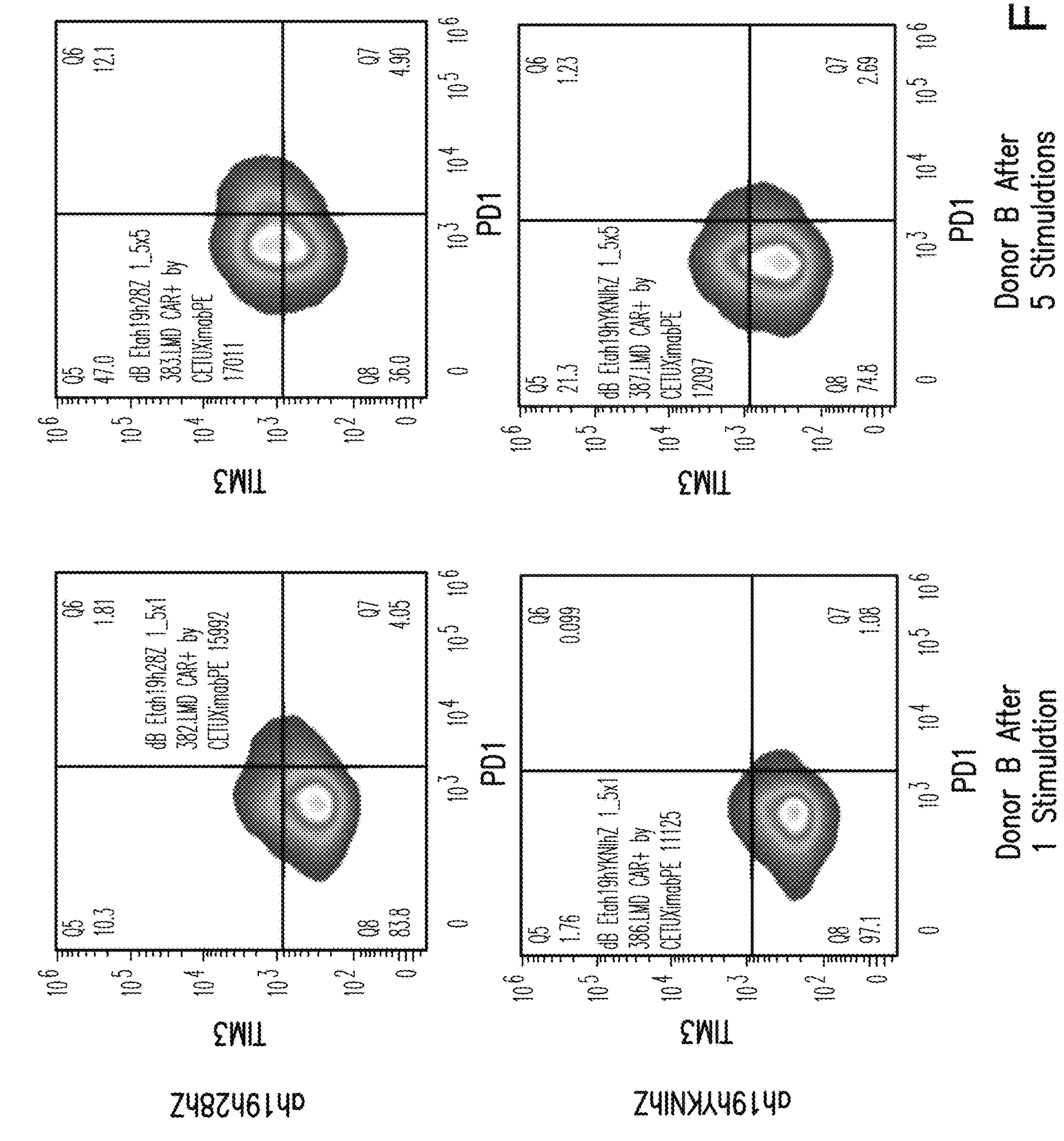

FIGS. 10A-10B show that CD28-YKNI mutant CAR T cells expressed lower levels of co-inhibitory molecules in the setting of single or multiple stimulations. LAG3 and PD1 (FIG. 10A) and TIM-3 and PD1 (FIG. 10B) expressions were measured in CD28-YKNI mutant CAR T cells (ah19hYKNIhZ) and wild-type CAR T cells (ah19h28 hZ) under single or multiple stimulations.

Figure 11:
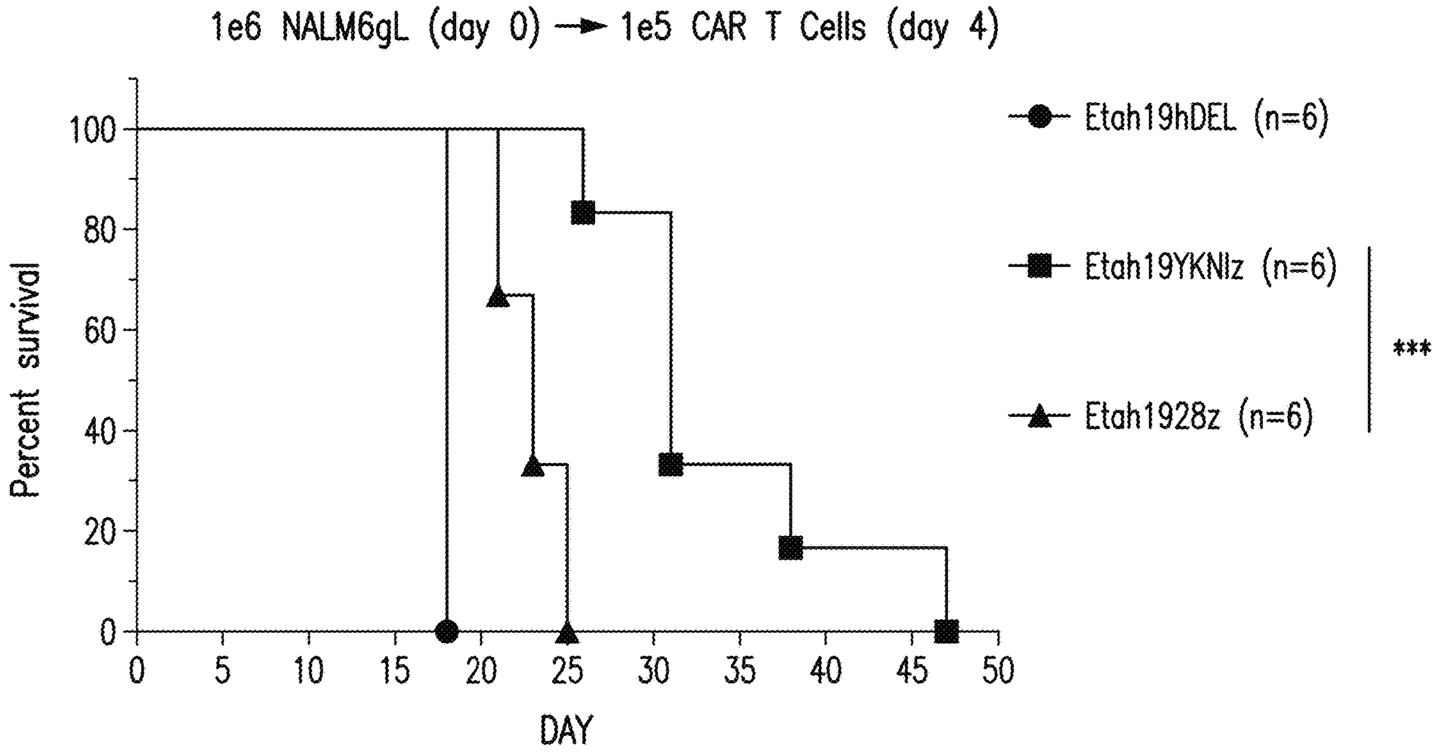

FIG. 11 shows that CD28-YKNI mutant CD19-targeted CAR T cells outperformed standard CD28-based CAR T cells in vivo. NCG mice were inoculated with $10^6$ NALM6gfp$^+$ffLUC$^+$ tumor cells, and were treated with CAR T cells 4 days later. Survival rate was charted. CAR T cells were derived from two different healthy donors.

Figure 12:
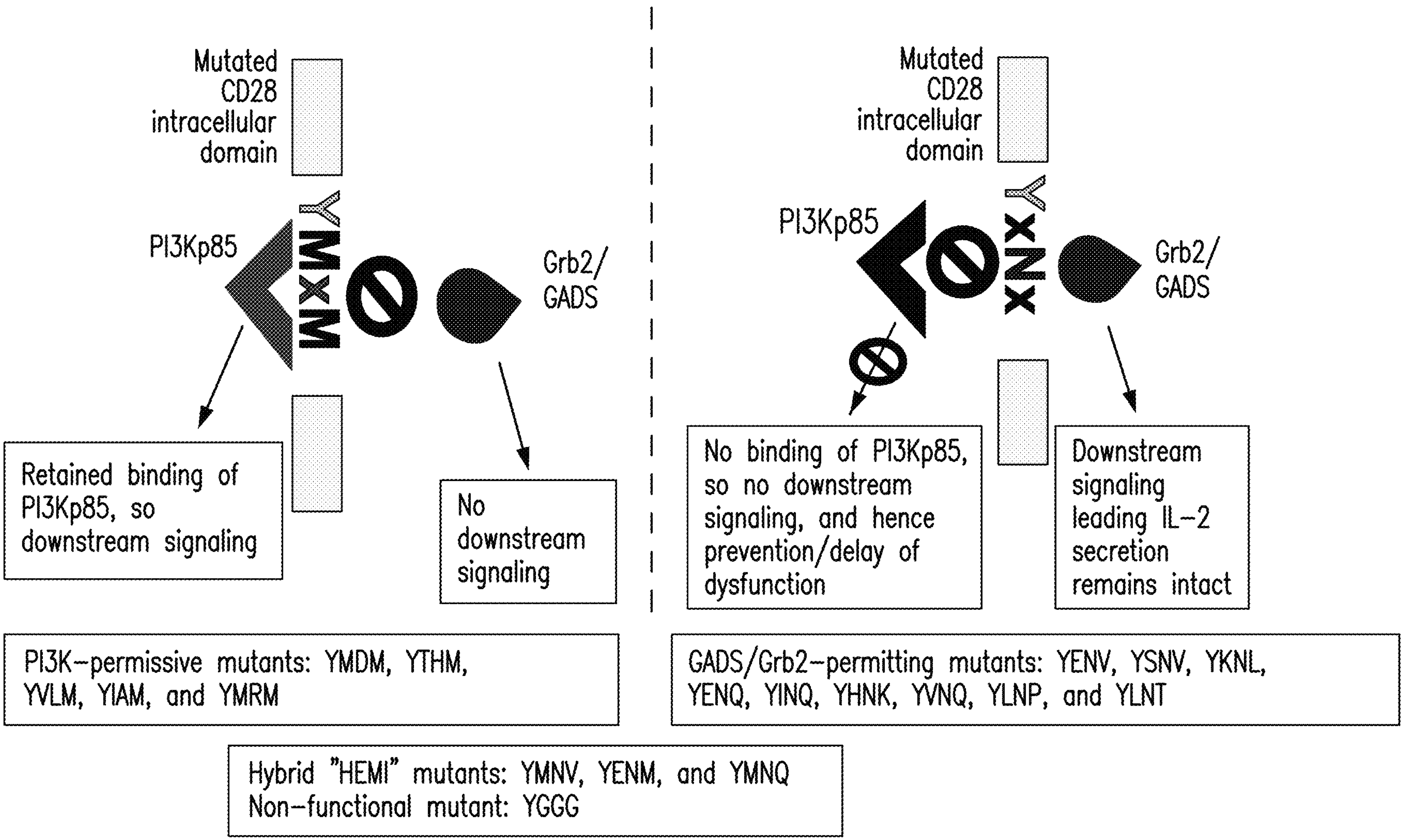

FIG. 12 is a schematic showing of exemplary CD28 mutants that have modified PI3Kp85 and Grb2/GADS binding ability to CD28 (SEQ ID NOs: 20 and 21, left to right, respectively).

Figure 13:
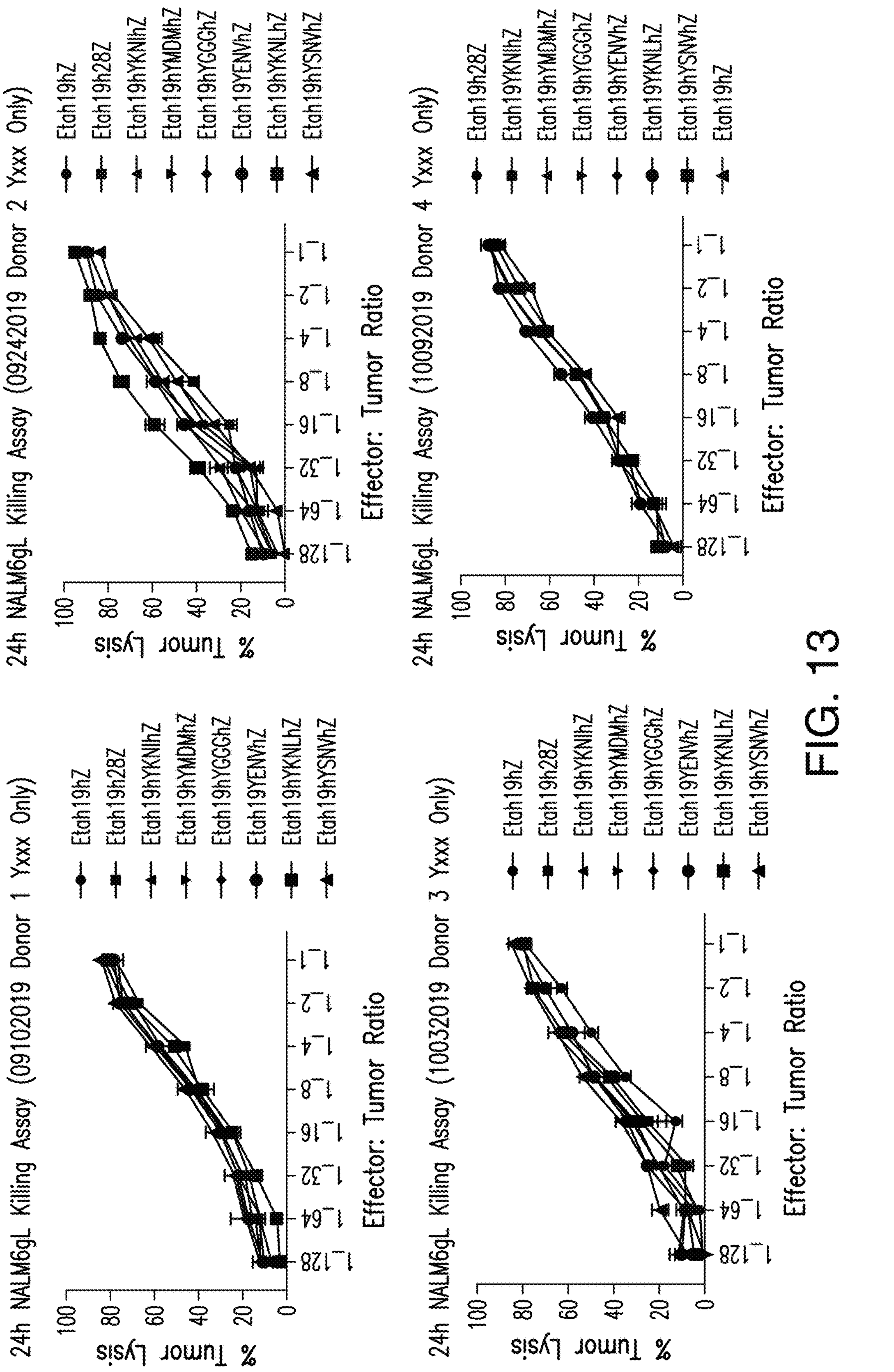

FIG. 13 shows that CD28-YKNI mutant CAR T cells demonstrated comparable killing capacity in 24-hour killing assays. Human CD19-targeted CAR T cells expressing a truncated EGFR domain (Etah19) were cocultured with CD19+ NALM6 cells expressing GFP-ffLuciferase (NALM6gL) at different effector: tumor ratios, and tumor cell lysis (relative to a non-signaling CAR T cell) was measured by bioluminescence 24 hours later.

Figure 14:
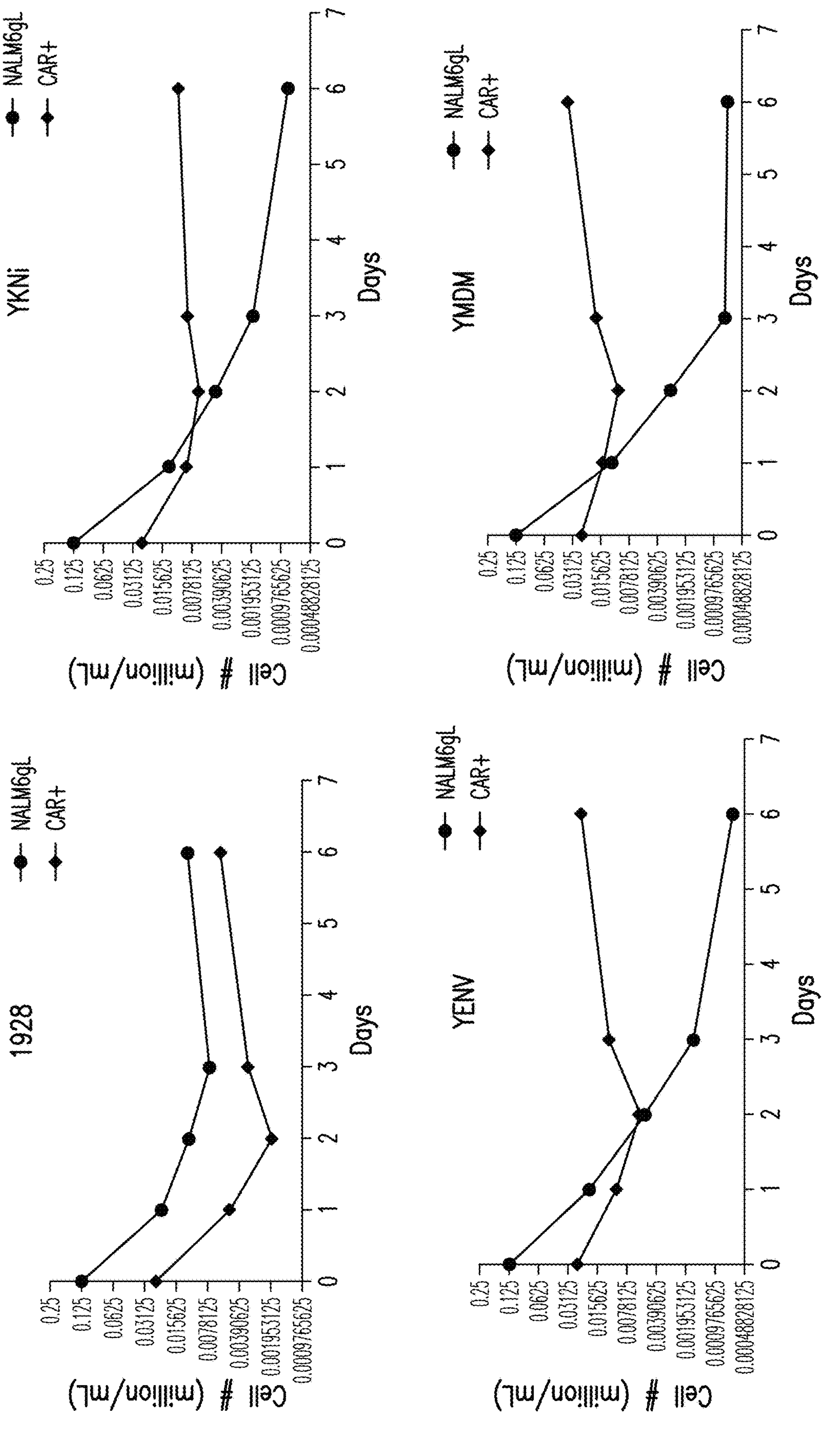

FIG. 14 shows that CD28-Yxxx mutant CD19-targeted CAR T cells (YKNI, YENV, and YMDM (SEQ ID NOs: 26, 22, 32, left to right, respectively)) outperformed standard CD28-based CAR T cells in vitro. Human CD19-targeted CAR T cells were cocultured with NALM6 at an E: T ratio of 1:5 at an initial concentration of 25,000 CAR T cells/mL. Concentrations of CAR+ and NALM6 were measured daily and plotted over the course of 6 days.

Figure 15:
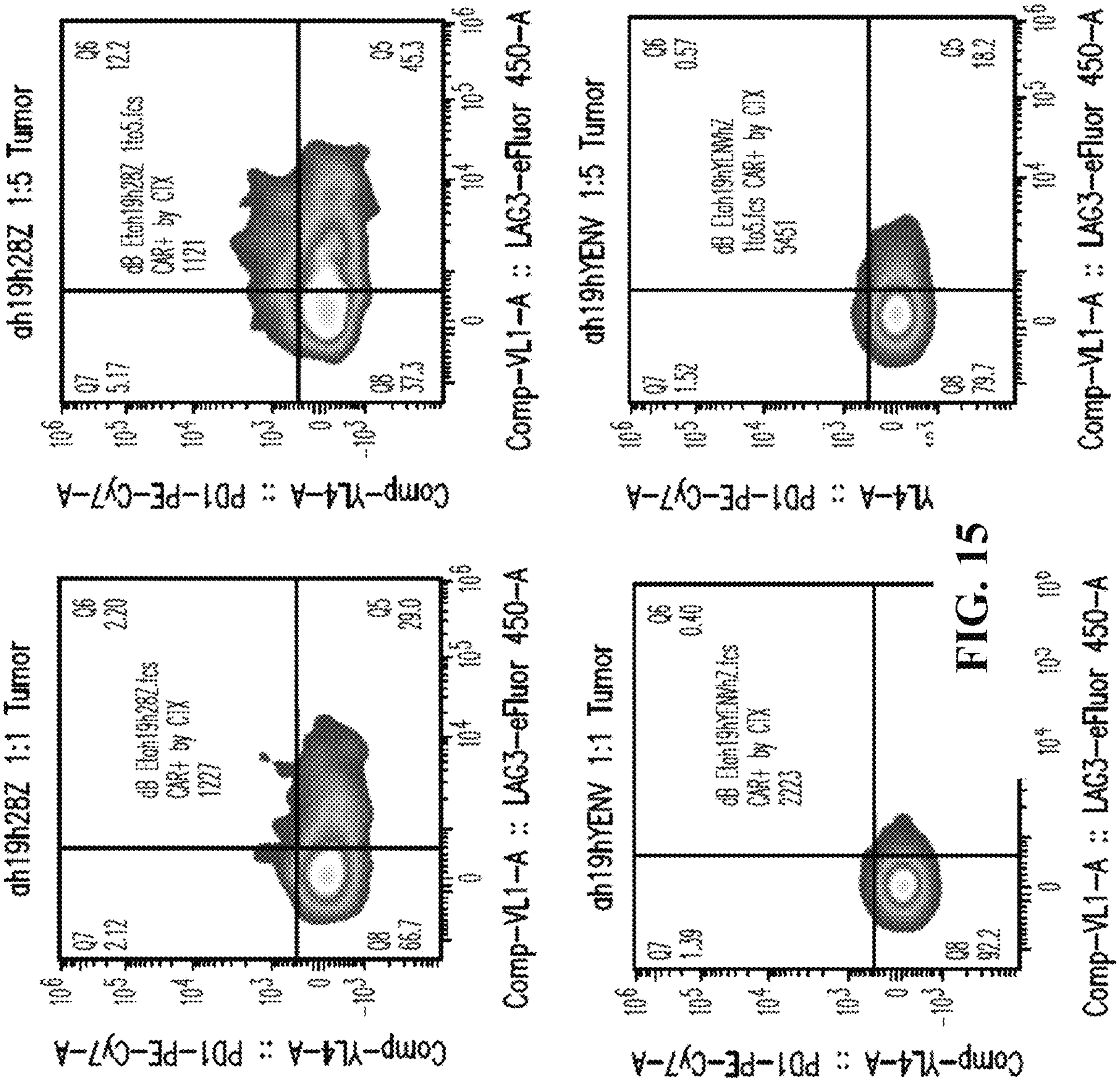
Figure 15:
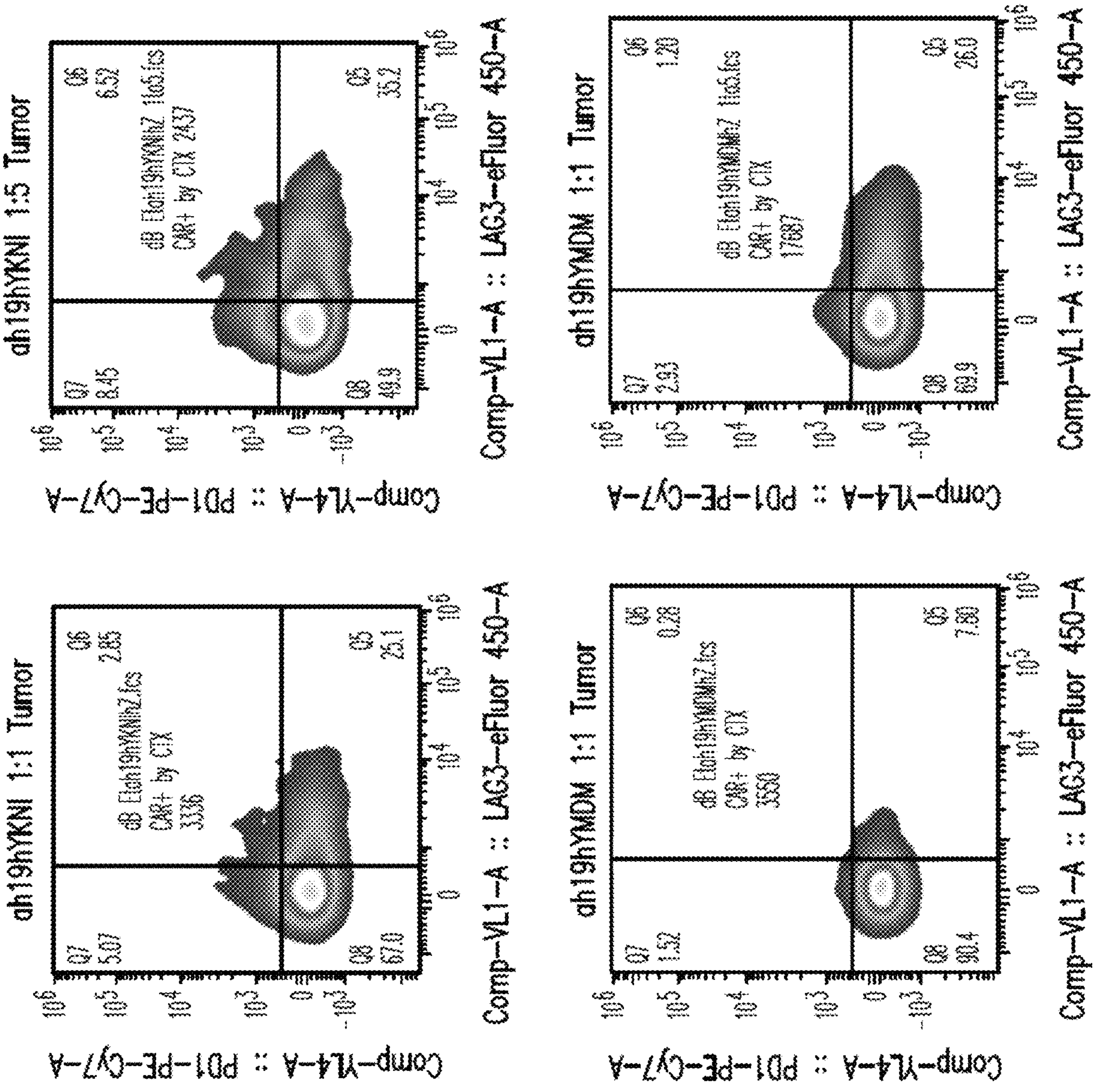

FIG. 15 shows that CD28 mutants demonstrated a favorable exhaustion immunophenotype. CAR T cells were cocultured with NALM6gL at an initial E: T of 1:5 (1 stimulation). In parallel, CAR T cells were repeatedly stimulated with the same amount of tumor for a total of 5 stimulations (with 1 stimulation every 12 hours). Approximately ten days post initiation of coculture, exhaustion markers (TIM3 and PD1) were assessed by flow cytometry.

Figure 16:
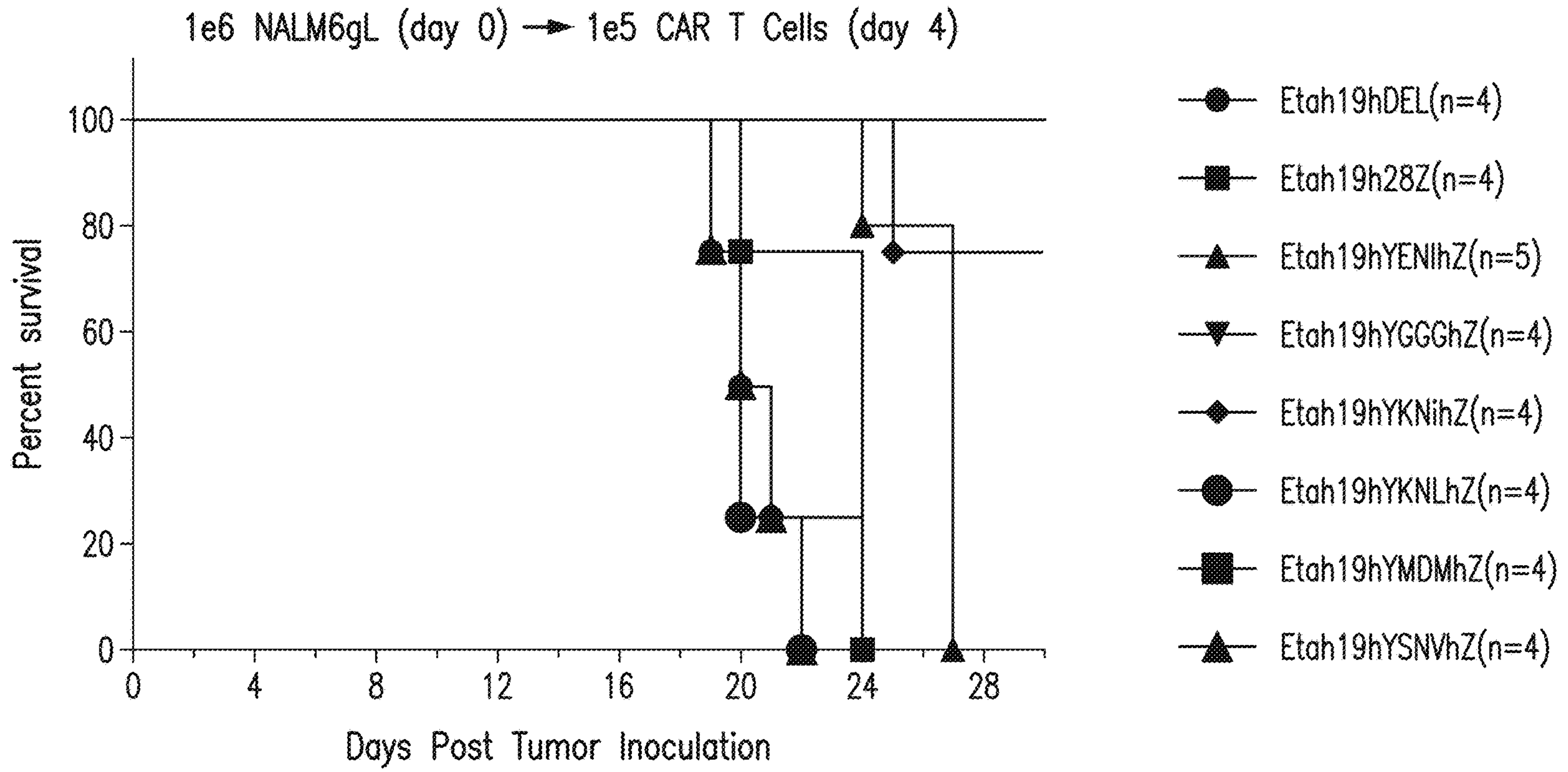

FIG. 16 shows the survival curve of NCG mice that were inoculated with $1x10^6$ NALM6gfp$^+$ffLUC$^+$ tumor cells and were treated with different CAR T cells.

Figure 17:
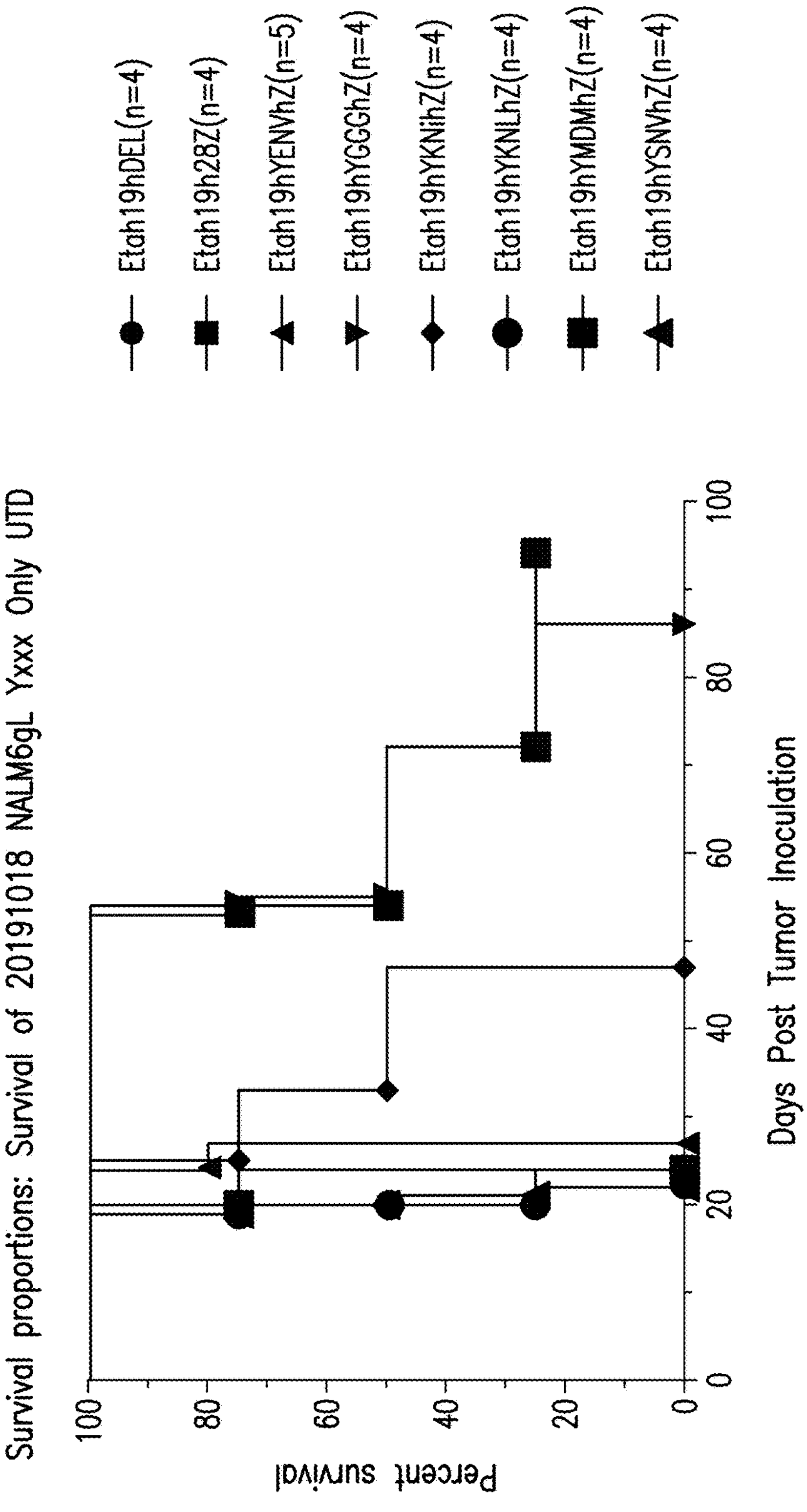
Figure 18:
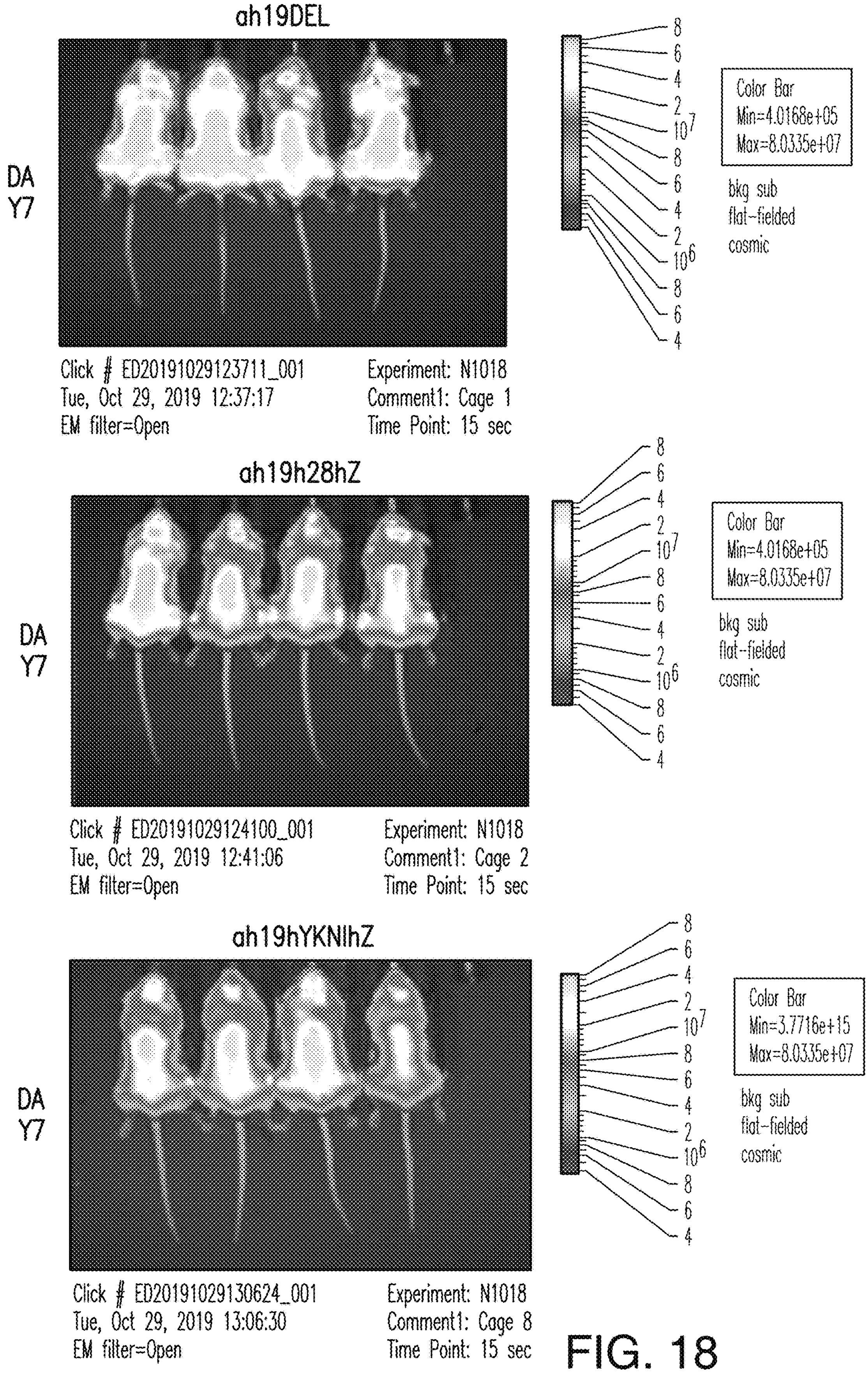
Figure 18:
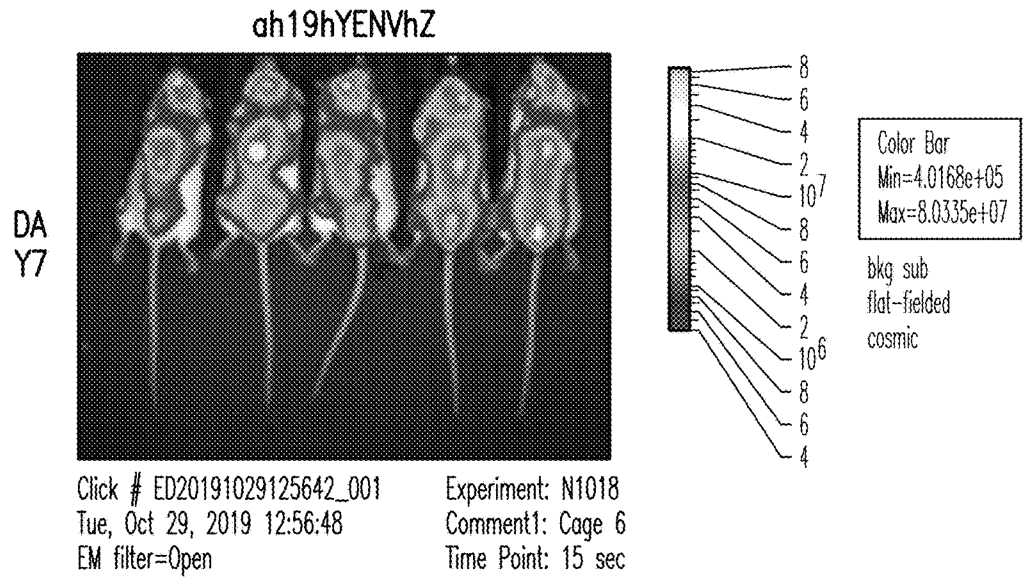
Figure 18:
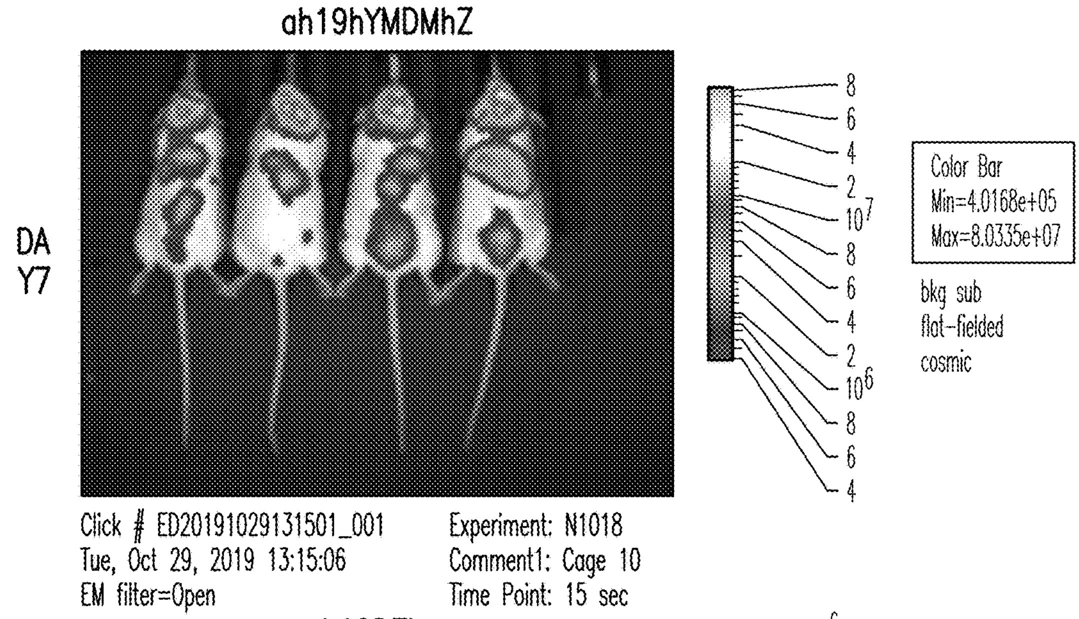
Figure 18:
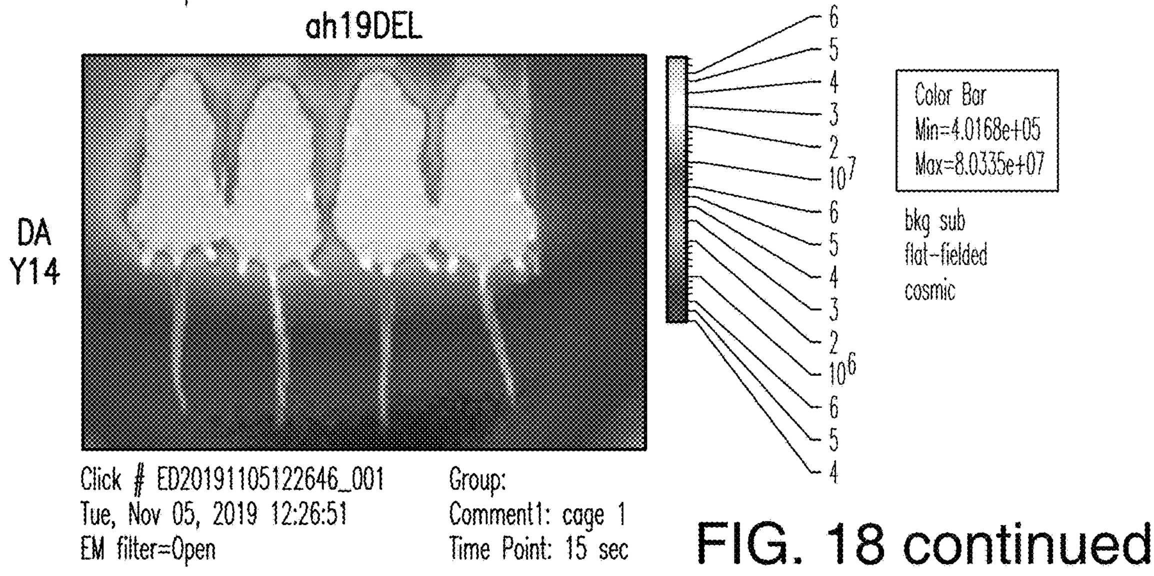
Figure 18:
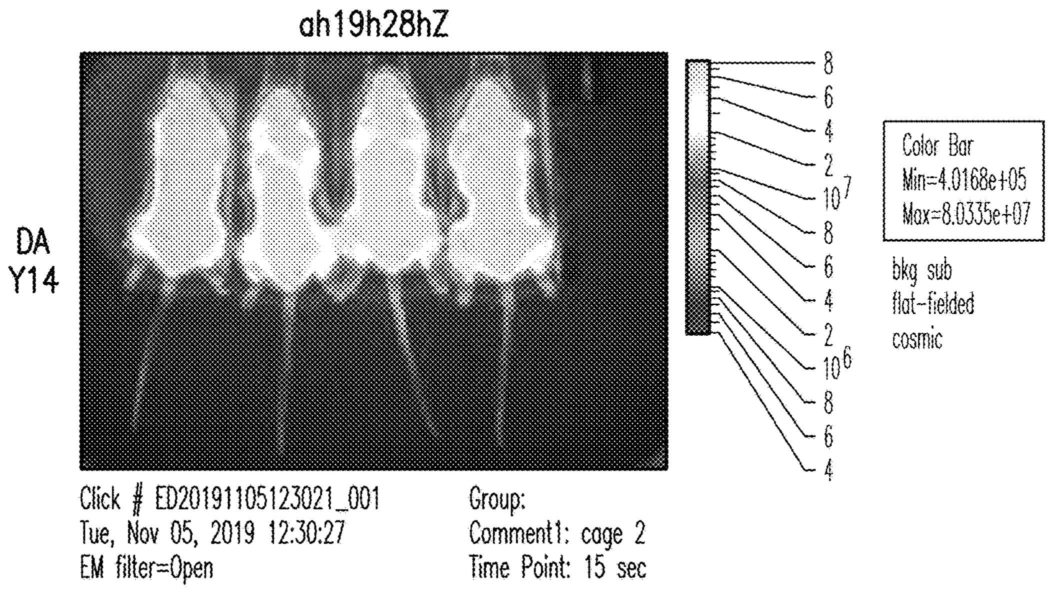
Figure 18:
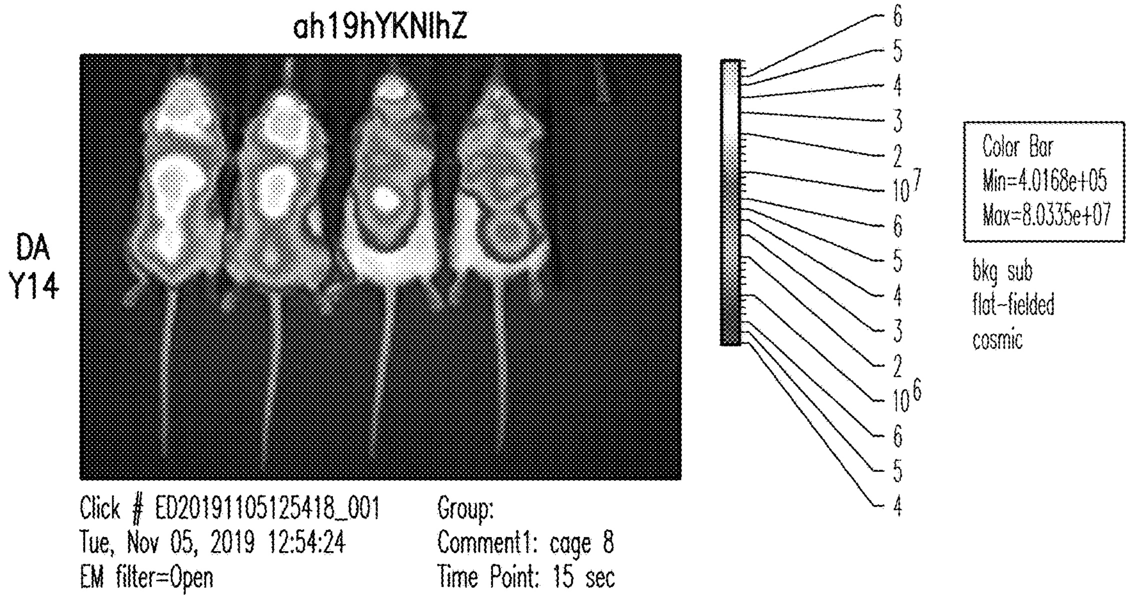
Figure 18:
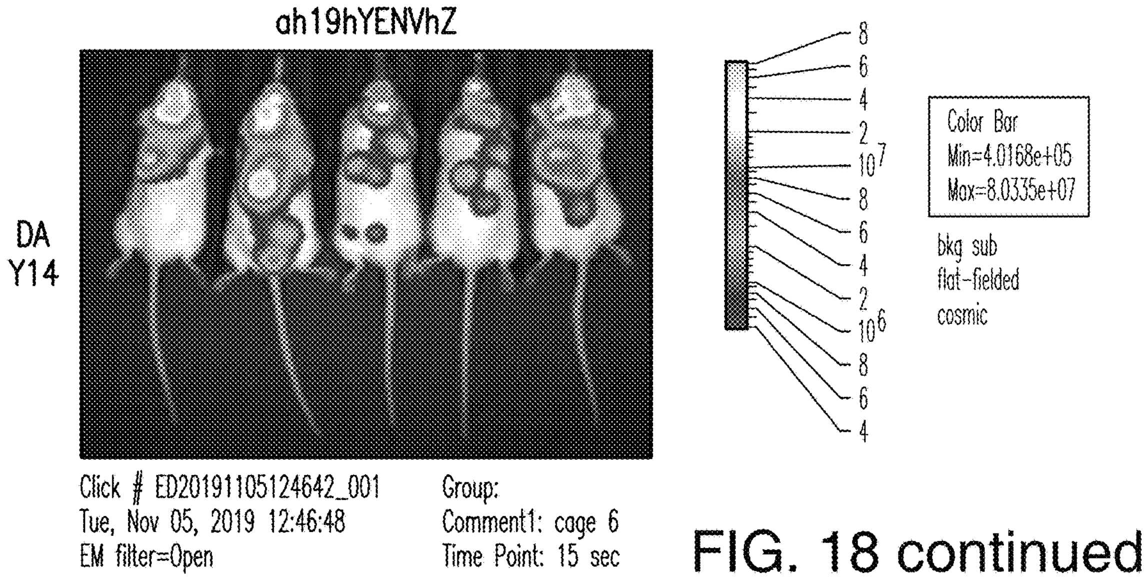
Figure 18:
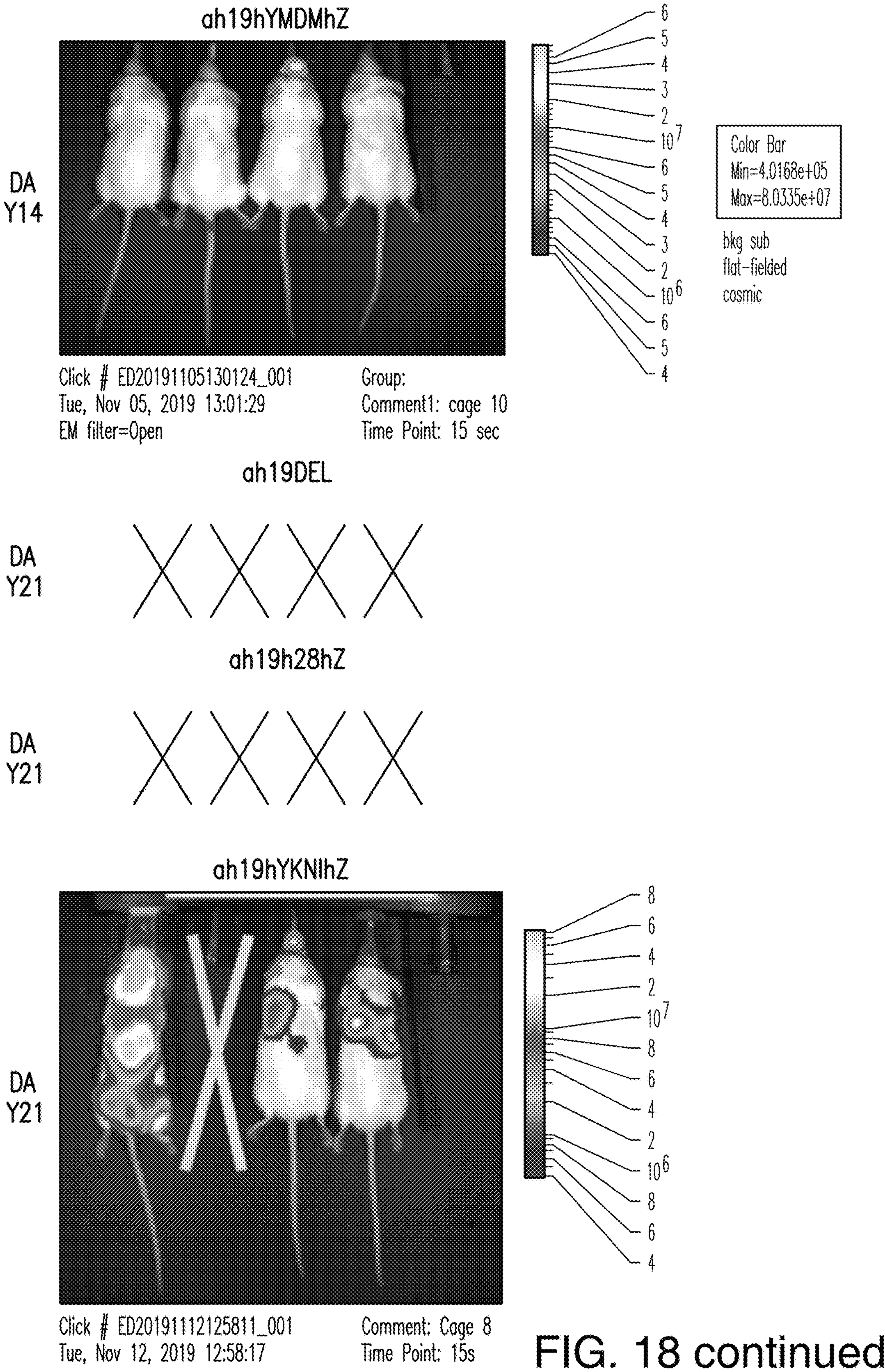
Figure 18:
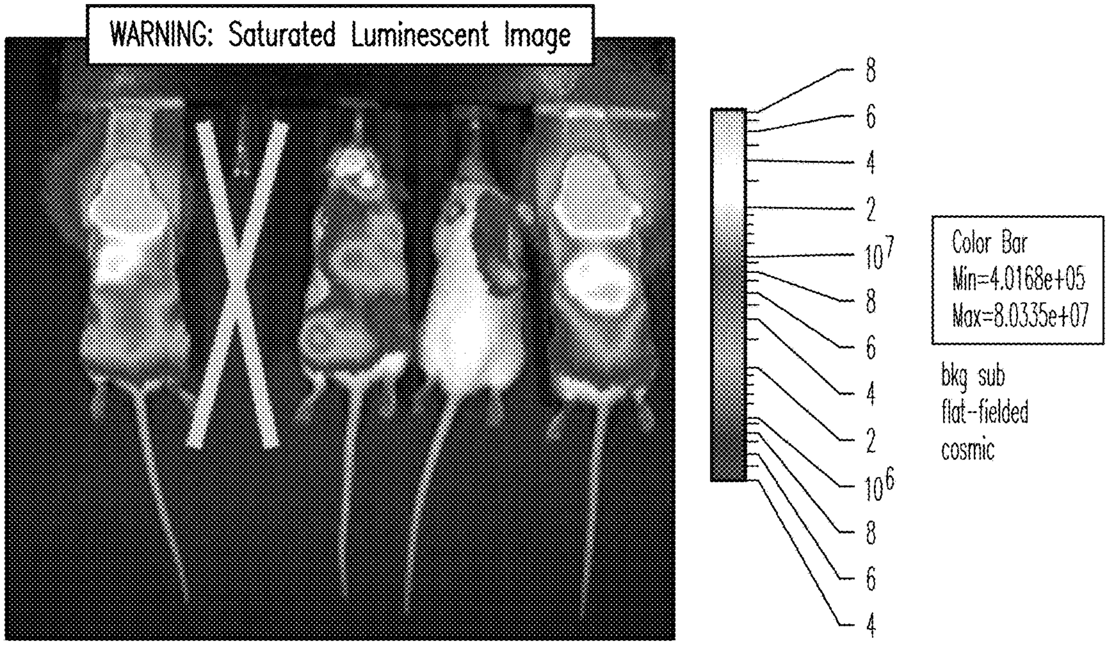
Figure 18:
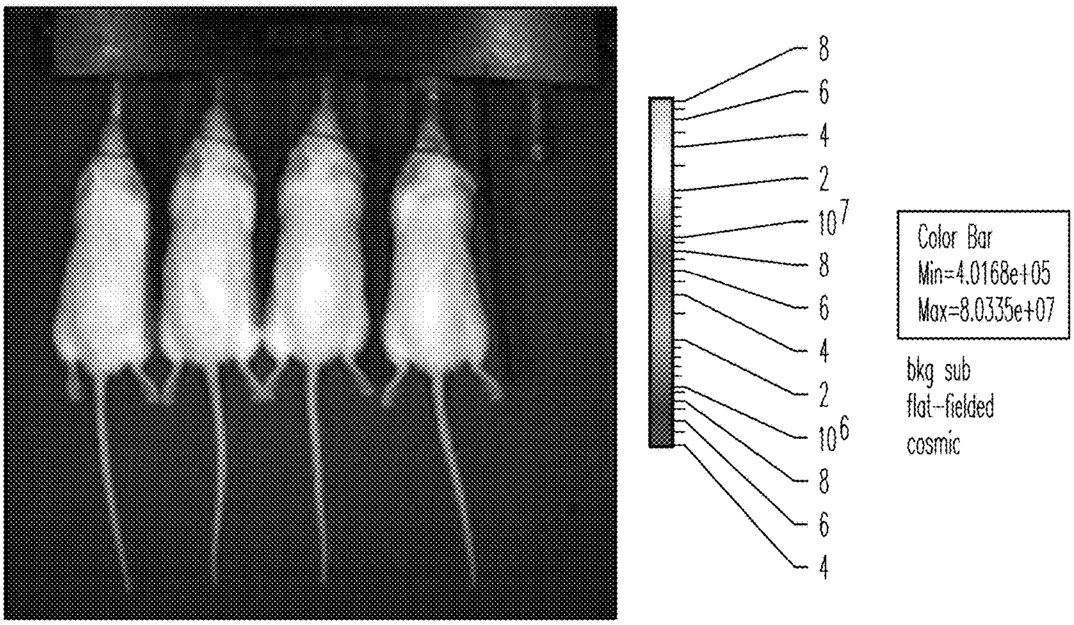

FIG. 17 shows the survival curve of NCG mice that were inoculated with $1\times10^6$ NALM6gfp$^+$ffLUC$^+$ tumor cells and were treated with different CAR T cells FIG. 18 shows the bioluminescence images of NCG mice that were inoculated with $1\times10^6$ NALM6gfp$^+$ffLUC$^+$ tumor cells and were treated with different CAR T cells. Bioluminescence was measured weekly.

Figure 19:
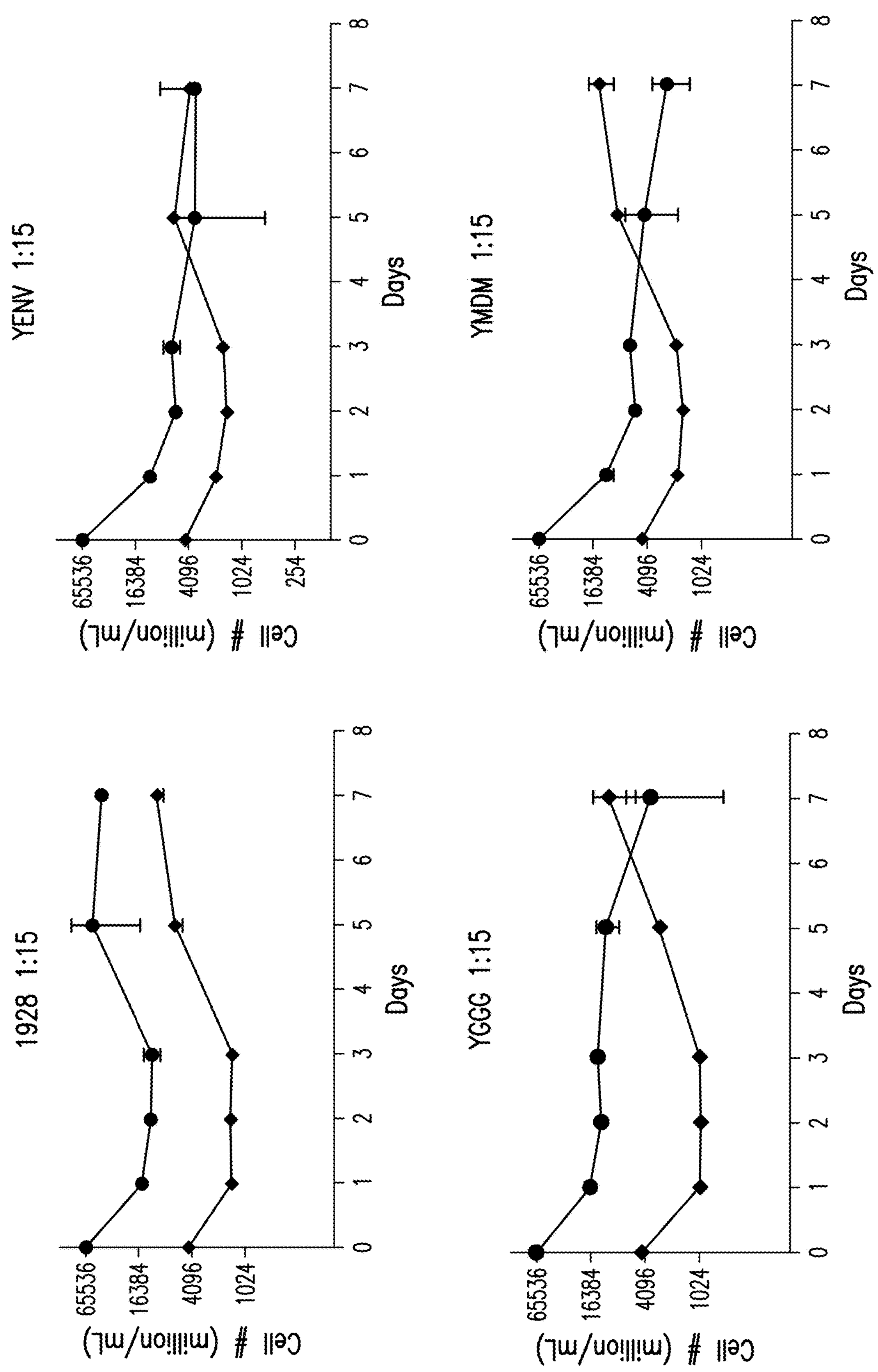
Figure 19:
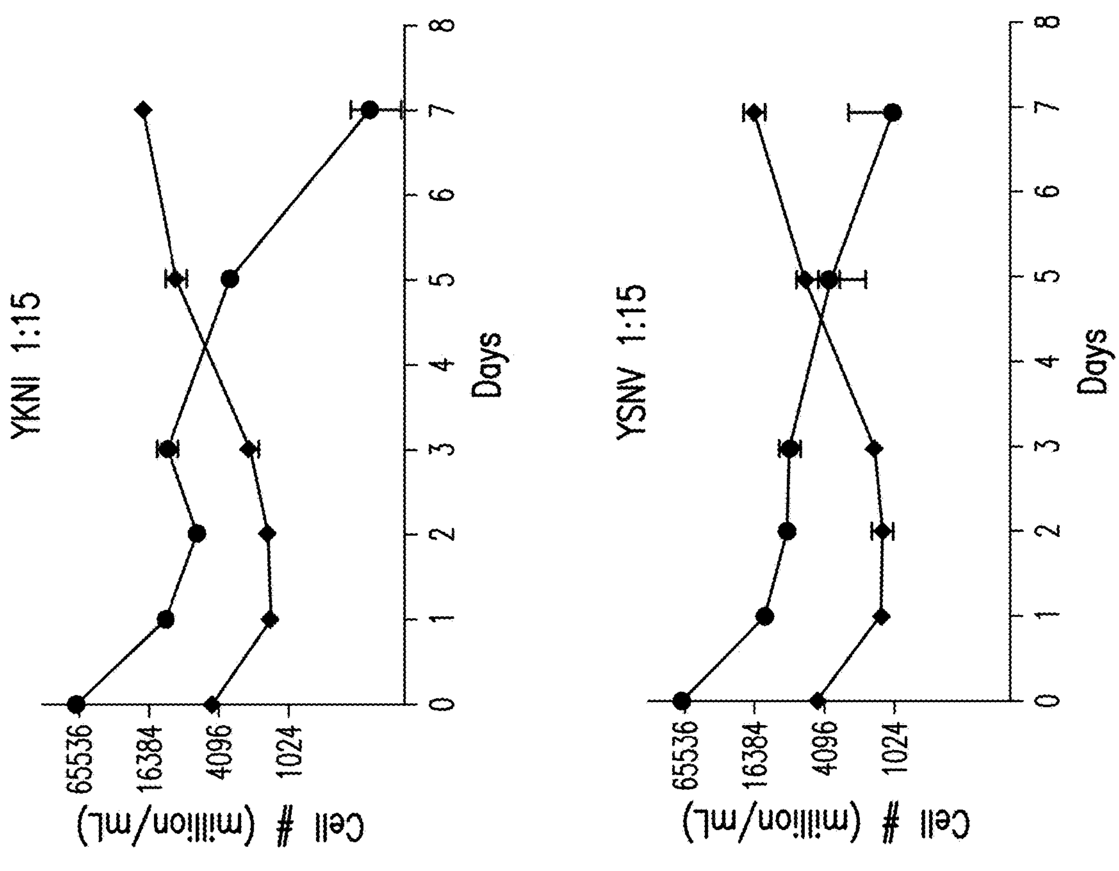

FIG. 19 shows that CD28-Yxxx mutant CD19-targeted CAR T cells demonstrated potent long-term cytotoxic capacity in vitro. Human CD19-targeted CAR T cells (lines with diamond signs) were cocultured with NALM6gL (lines with circle signs) at an E:T ratio of 1:15. Concentrations of CAR+ T cells and NALM6 were measured daily and were plotted over the course of 7 days as cells/mL.

Figure 20:
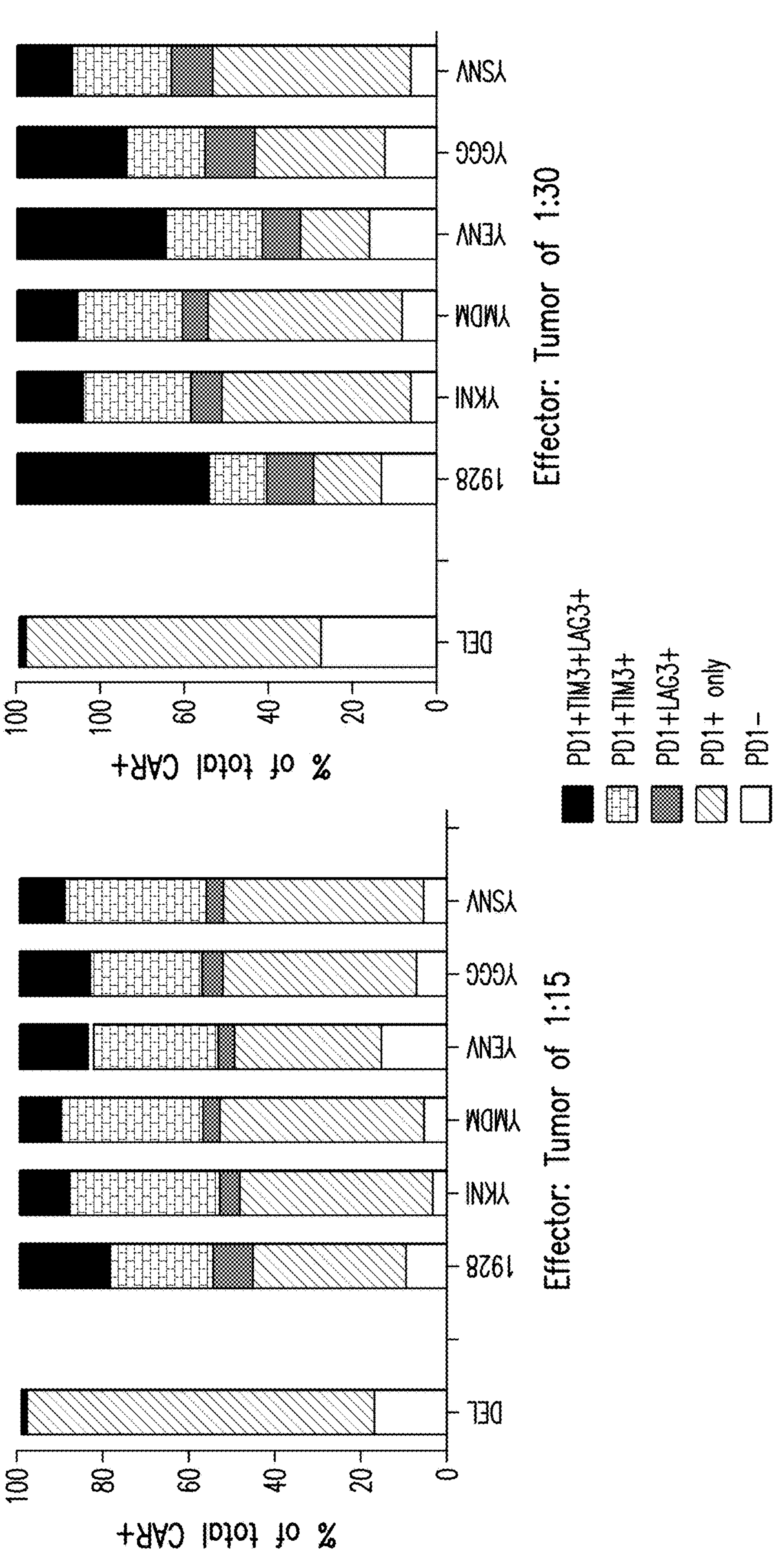

FIG. 20 shows that CD28-Yxxx mutant CD19-targeted CAR T cells displayed a favorable exhaustion immunophenotype. CAR T cells were cocultured with NALM6gL at an E:T ratio of 1:15 or 1:30. Five days later, the expressions of exhaustion marker including LAG3, TIM3 and PD1 in the CAR T cells were assessed by flow cytometry.

Figure 21:
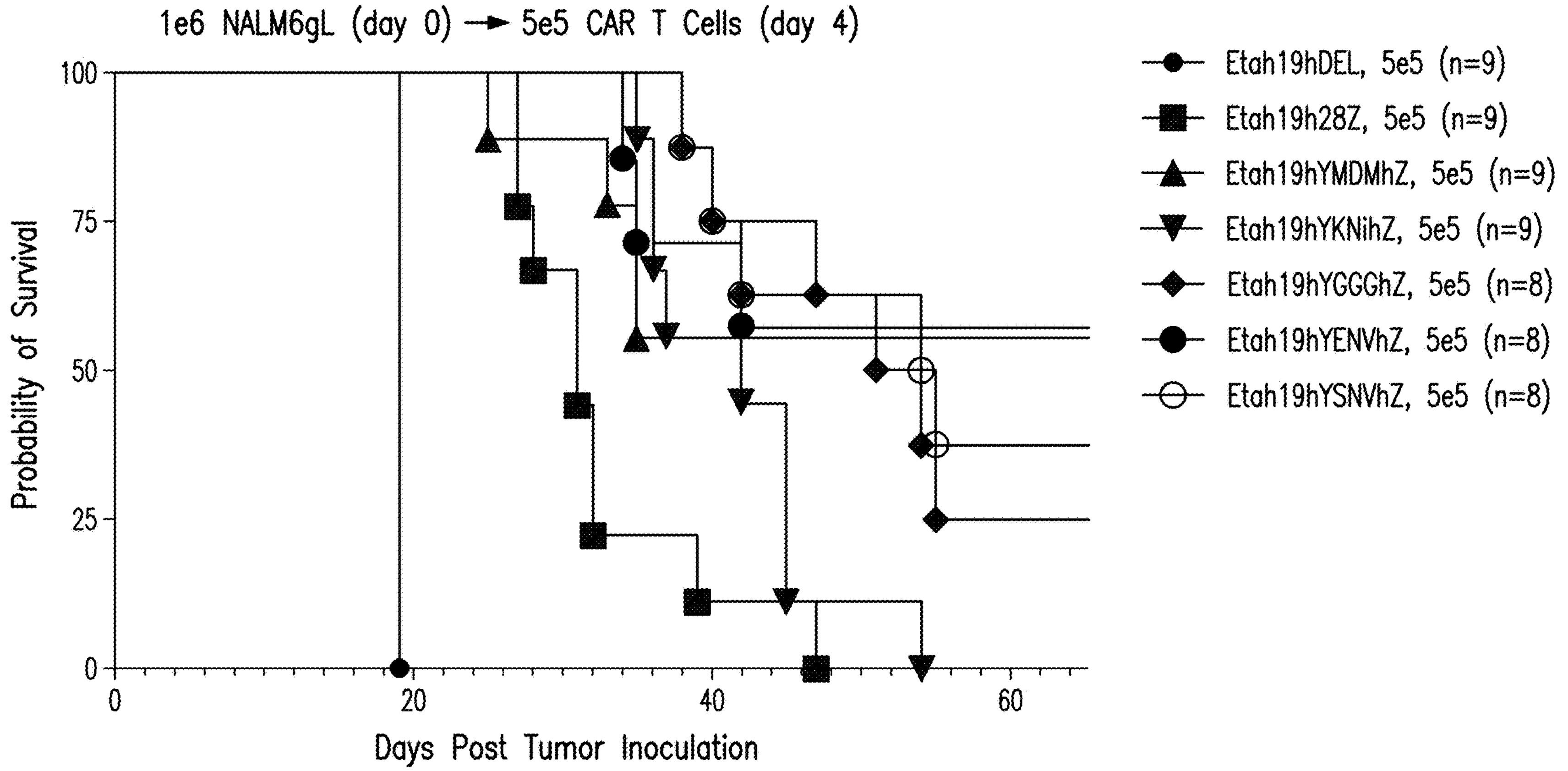

FIG. 21 shows the survival curve of NCG mice that received CD28-Yxxx mutant CD19-targeted CAR T cells. NCG mice were inoculated with $1\times10^6$ NALM6gfp$^+$ffLUC$^+$ tumor cells, and were treated with 500,000 CAR T cells 4 days later. CAR T cells were derived from two different healthy donors.

Figure 22:
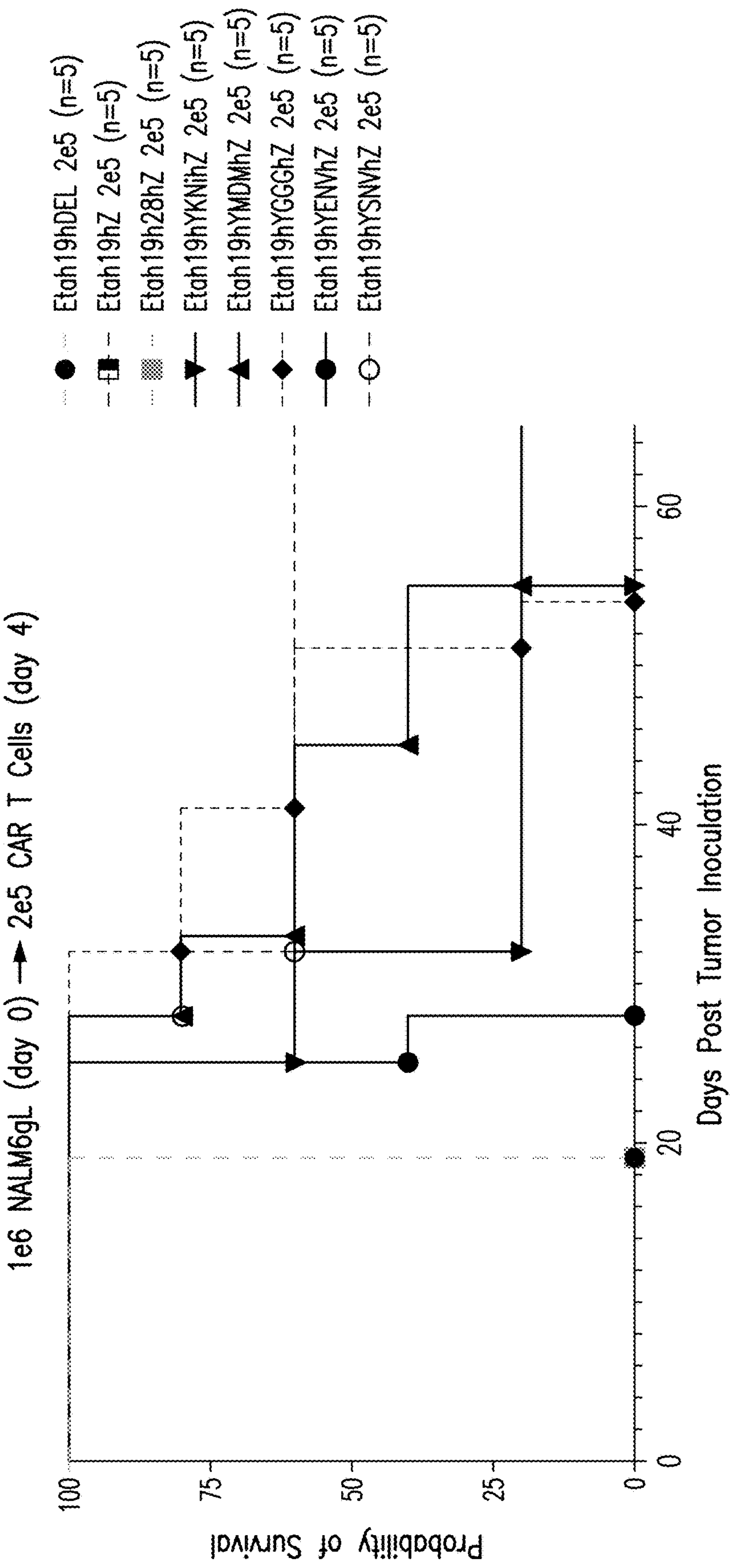

FIG. 22 shows the survival curve of NCG mice received CD28-Yxxx mutant CD19-targeted CAR T cells. NCG mice were inoculated with $1\times10^6$ NALM6gfp$^+$ffLUC$^+$ tumor cells, and were treated with 200,000 CAR T cells 4 days later. CAR T cells were derived from a single healthy donor.

Figure 23:
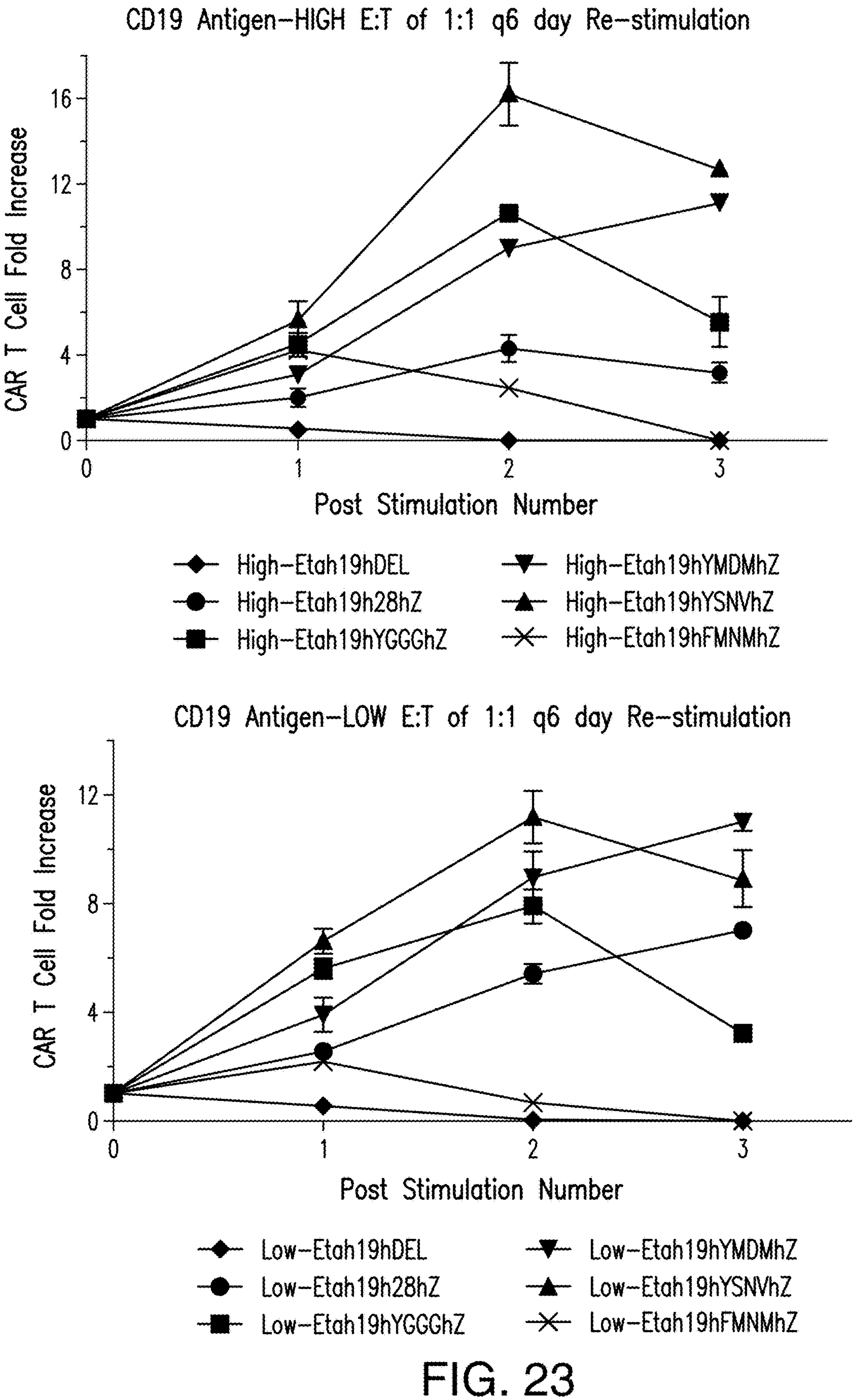

FIG. 23 shows that CD28-Yxxx mutant CD19-targeted CAR T cells displayed enhanced proliferation in vitro independent of antigen-density. Human CD19-targeted CD28-Yxxx mutant CAR T cells were cocultured with NALM6gL with either high or low CD19 antigen density at an E: T ratio of 1:1. Every 6 days, CAR$^+$ T cells were counted and re-stimulated with NALM6gL, for a total of three stimulations.

Figure 24A:
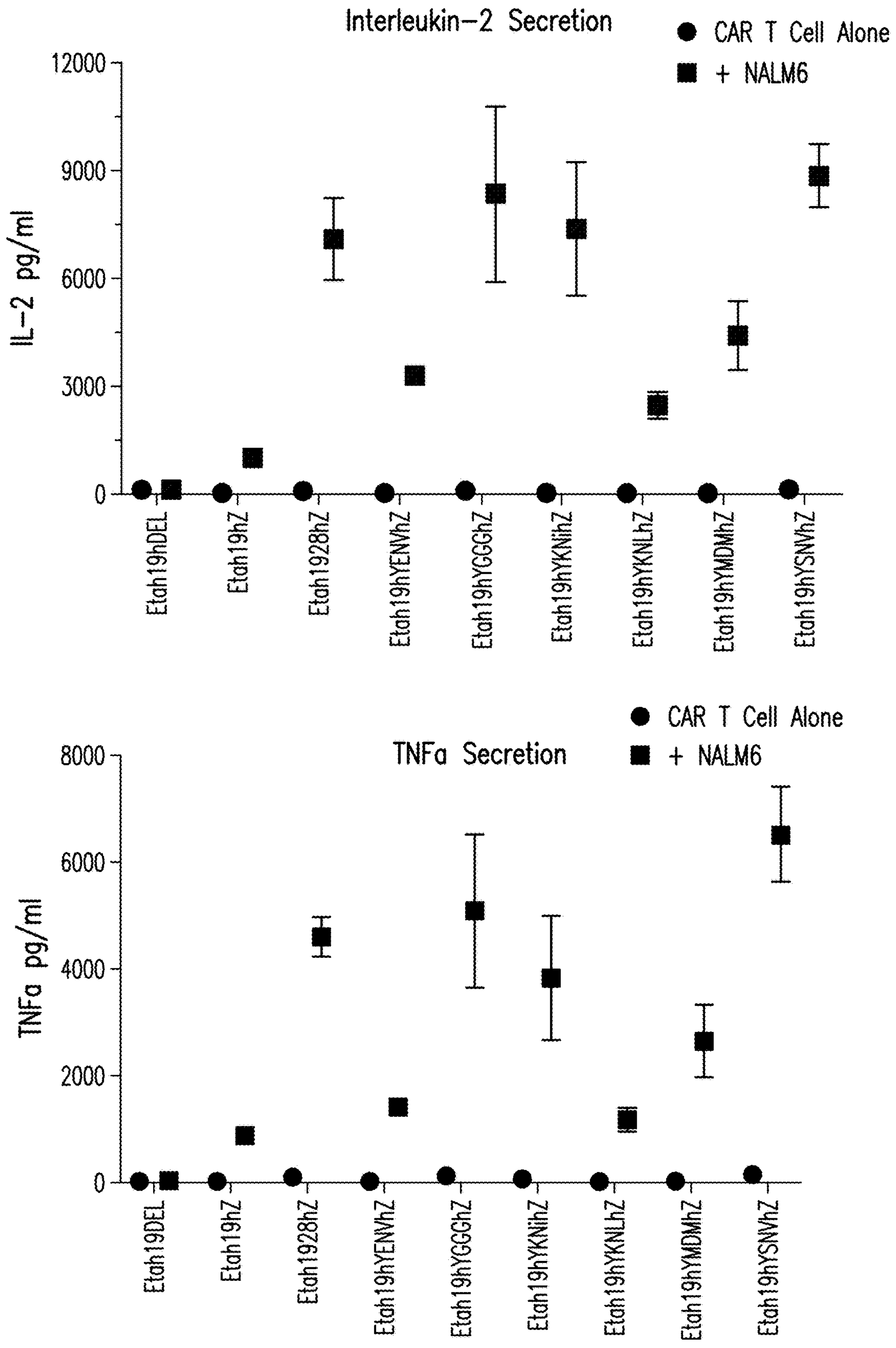
Figure 24B:
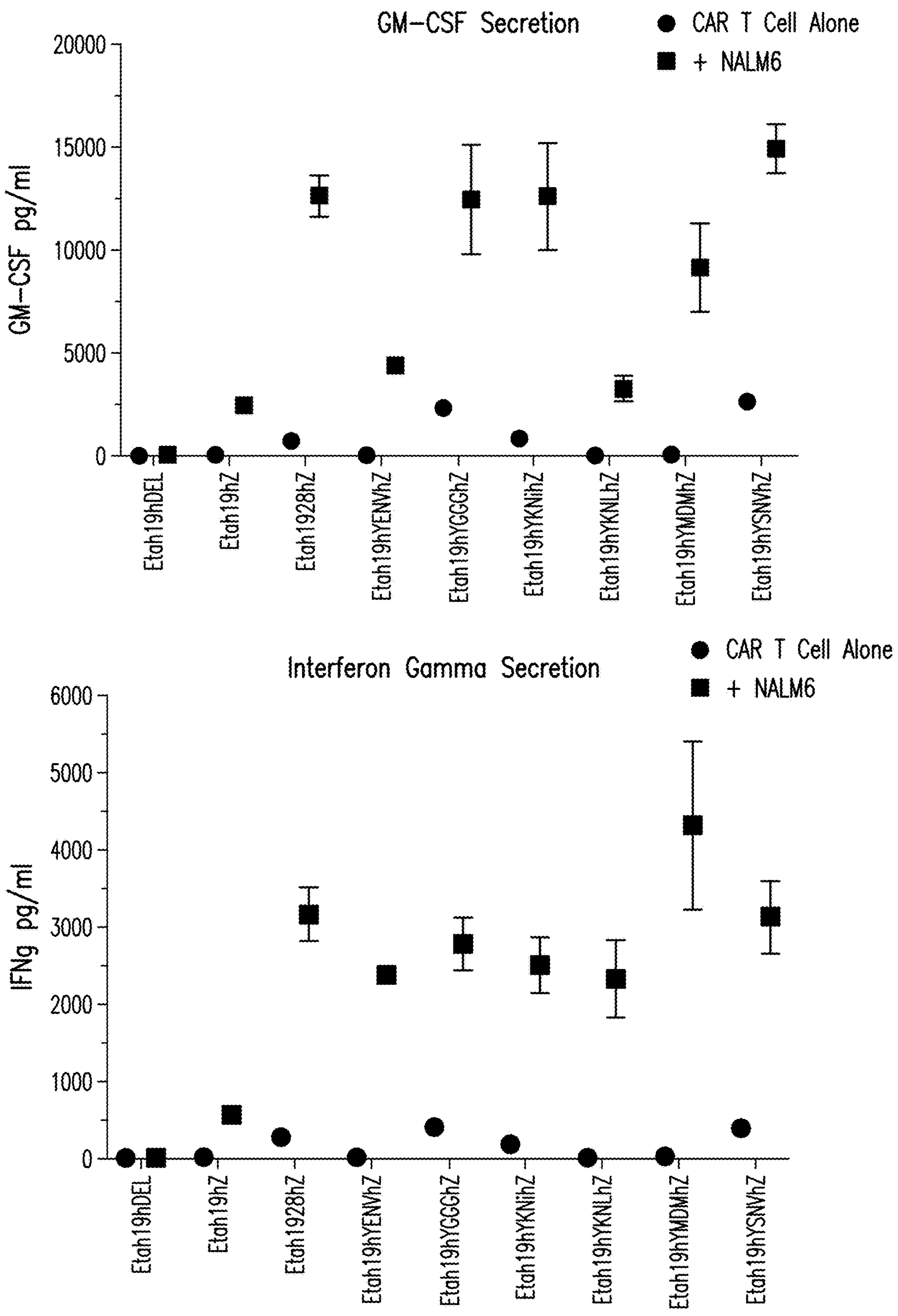
Figure 24C:
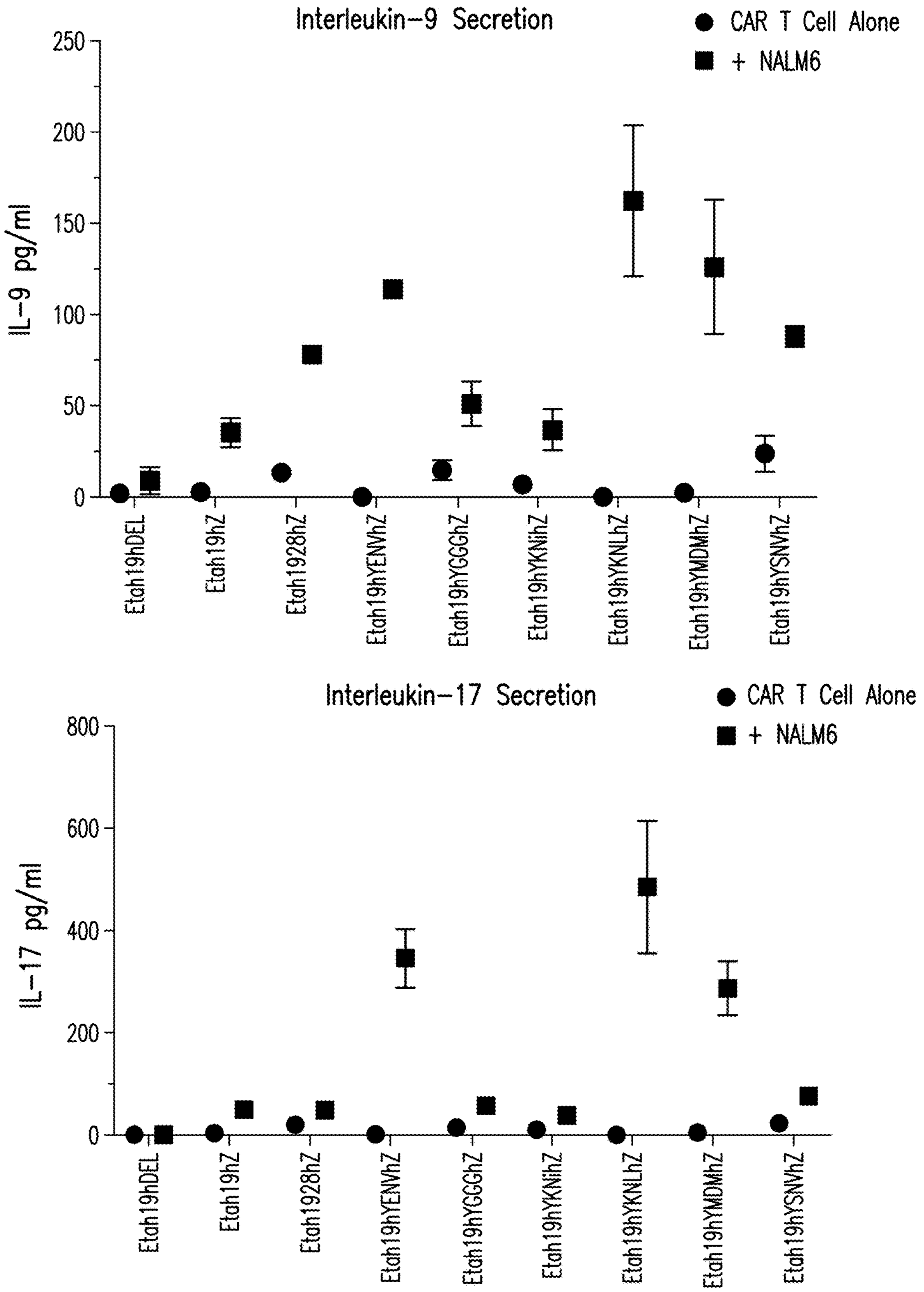

FIGS. 24A-24C show that CD28-Yxxx mutant CD19-targeted CAR T cells demonstrated unique cytokine secretion profiles on exposure to antigens. Human CD19-targeted CD28-Yxxx mutant CAR T cells were cocultured with NALM6gL. Twenty-four hours later, supernatant was collected and cytokines, including interleukin-2 (FIG. 24A), TNF-α (FIG. 24A), GM-CSF (FIG. 24B), interferon-y (FIG. 24B), IL-9 (FIG. 24C), and IL-17 (FIG. 24C) were measured by the Luminex bead-based multiplex assay.

5. DETAILED DESCRIPTION

The presently disclosed subject matter provides chimeric antigen receptors (CARs) comprising at least one co-stimulatory signaling domain that comprises a CD28 polypeptide comprising a mutated YMNM motif. The CD28 polypeptide has reduced recruitment of a p85 subunit of a phosphoinositide 3-kinase (PI3K) signaling as compared to a CD28 molecule comprising a native YMNM motif. In certain embodiments, a p85 subunit of a PI3K signaling does not bind to the mutated YMNM motif. In certain embodiments, a p85 subunit of a PI3K signaling does not bind to the mutated YMNM motif and growth factor receptor bound receptor 2 (Grb2) and/or Grb2-related adaptor downstream of Shc (GADS) binds to the mutated YMNM motif. In certain embodiments, Grb2 and/or GADS does not bind to the mutated YMNM motif. In certain embodiments, Grb2 and/or GADS does not bind to the mutated YMNM motif and a p85 subunit of a PI3K signaling binds to the mutated YMNM motif.

The presently disclosed subject matter also provides cells (e.g., immunoresponsive cells, e.g., T cells or NK cells) comprising a presently disclosed CAR. The presently disclosed subject matter further provides methods of using the presently disclosed cells for inducing and/or enhancing an immune response to a target antigen, and/or for treating and/or preventing a neoplasm or tumor, and/or a pathogen infection. The presently disclosed subject matter is based, at least in part, on the discovery that cells comprising CARs comprising a mutated CD28 intracellular motif (i.e., a mutated YMNM motif) exhibit enhanced anti-tumor effects as compared to cells comprising CARs comprising a native CD28 intracellular motif (i.e., a native YMNM motif).

Non-limiting embodiments of the present disclosure are described by the present specification and Examples.

For purposes of clarity of disclosure and not by way of limitation, the detailed description is divided into the following subsections:

5.1 Definitions;
5.2 Chimeric Antigen Receptors (CARs);
5.3. Cells;
5.4. Composition and Vectors;
5.5. Polypeptides;
5.6 Formulations and Administration;
5.7 Methods of Treatment; and
5.8. Kits 5.1. Definitions Unless defined otherwise, all technical and scientific terms used herein have the meaning commonly understood by a person skilled in the art. The following references provide one of skill with a general definition of many of the terms used in the presently disclosed subject matter: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991).

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold or within 2-fold, of a value.

By "immunoresponsive cell" is meant a cell that functions in an immune response or a progenitor, or progeny thereof. In certain embodiments, the immunoresponsive cell is a cell of lymphoid lineage. Non-limiting examples of cells of lymphoid lineage include T cells, Natural Killer (NK) cells, B cells, and stem cells from which lymphoid cells may be differentiated. In certain embodiments, the immunoresponsive cell is a cell of myeloid lineage.

By "activates an immunoresponsive cell" is meant induction of signal transduction or changes in protein expression in the cell resulting in initiation of an immune response. For example, when CD3 Chains cluster in response to ligand binding and immunoreceptor tyrosine-based inhibition motifs (ITAMs) a signal transduction cascade is produced. In certain embodiments, when an endogenous TCR or an exogenous CAR binds to an antigen, a formation of an immunological synapse occurs that includes clustering of many molecules near the bound receptor (e.g. CD4 or CD8, CD3γ/δ/ε/ζ, etc.). This clustering of membrane bound signaling molecules allows for ITAM motifs contained within the CD3 chains to become phosphorylated. This phosphorylation in turn initiates a T cell activation pathway ultimately activating transcription factors, such as NF-κB and AP-1. These transcription factors induce global gene expression of the T cell to increase IL-2 production for proliferation and expression of master regulator T cell proteins in order to initiate a T cell mediated immune response.

By "stimulates an immunoresponsive cell" is meant a signal that results in a robust and sustained immune response. In various embodiments, this occurs after immune cell (e.g., T-cell) activation or concomitantly mediated through receptors including, but not limited to, CD28, CD137 (4-1BB), OX40, CD40 and ICOS. Receiving multiple stimulatory signals can be important to mount a robust and long-term T cell mediated immune response. T cells can quickly become inhibited and unresponsive to antigen. While the effects of these co-stimulatory signals may vary, they generally result in increased gene expression in order to generate long lived, proliferative, and anti-apoptotic T cells that robustly respond to antigen for complete and sustained eradication.

The term "antigen-recognizing receptor" as used herein refers to a receptor that is capable of activating an immunoresponsive cell (e.g., a T cell) in response to its binding to an antigen.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat et al., Sequences of Proteins of Immunological Interest, Fifth Edition, U.S. Department of Health and Human Services (1991); NIH Publication No. 91-3242). In certain embodiments, the CDRs are identified according to the IMGT numbering system. As used herein, the term "single-chain variable fragment" or "scFv" is a fusion protein of the variable regions of the heavy ($V_H$) and light chains ($V_L$) of an immunoglobulin covalently linked to form a $V_H$:: $V_L$ heterodimer. The $V_H$ and $V_L$ are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker is usually rich in glycine for flexibility, as well as serine or threonine for solubility.

"Linker", as used herein, shall mean a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains).

Despite removal of the constant regions and the introduction of a linker, scFv proteins retain the specificity of the original immunoglobulin. Single chain Fv polypeptide antibodies can be expressed from a nucleic acid including $V_H$- and $V_L$-encoding sequences as described by Huston et al., *Proc Nat Acad Sci USA* (1988);85:5879-5883,; U.S. Pat. Nos. 5,091,513, 5,132,405 and 4,956,778; and U.S. Patent Publication Nos. 20050196754 and 20050196754. Antagonistic scFvs having inhibitory activity have been described (Zhao et al., *Hyrbidoma* (*Larchmt*) 2008; 27 (6): 455-51; Peter et al., *J Cachexia Sarcopenia Muscle* (2013); 4 (1): 79-86; Shieh et al., *J Imunol* (2009); 183 (4): 2277-85; Giomarelli et al., *Thromb Haemost* (2007);97 (6): 955-63; Fife et al., *J C I* (2006); 116 (8): 2252-61; Brocks et al., *Immunotechnology* (1997); 3 (3): 173-84; Moosmayer et al., *Ther Immunol* (1995); 2 (10): 31-40). Agonistic scFvs having stimulatory activity have been described (Peter et al., *J Biol Chem* (2003); 25278 (38): 36740-7; Xie et al., Nat Biotech (1997); 15 (8): 768-71; Ledbetter et al., *Crit Rev Immunol* (1997); 17 (5-6): 427-55; Ho et al., *BioChem Biophys Acta* (2003); 1638 (3): 257-66).

As used herein, the term "affinity" is meant a measure of binding strength. Affinity can depend on the closeness of stereochemical fit between antibody combining sites and antigen determinants, on the size of the area of contact between them, and/or on the distribution of charged and hydrophobic groups. Methods for calculating the affinity of an antibody for an antigen are known in the art, including, but not limited to, various antigen-binding experiments, e.g., functional assays (e.g., flow cytometry assay).

The term "chimeric antigen receptor" or "CAR" as used herein refers to a molecule comprising an extracellular antigen-binding domain that is fused to an intracellular signaling domain that is capable of activating an immunoresponsive cell, and a transmembrane domain. In certain embodiments, the extracellular antigen-binding domain of a CAR comprises an scFv. The scFv can be derived from fusing the variable heavy and light regions of an antibody. Alternatively or additionally, the scFv may be derived from Fab's (instead of from an antibody, e.g., obtained from Fab libraries). In certain embodiments, the scFv is fused to the transmembrane domain and then to the intracellular signaling domain.

As used herein, the term "nucleic acid molecules" include any nucleic acid molecule that encodes a polypeptide of interest. Such nucleic acid molecules need not to be 100% homologous or identical with an endogenous nucleic acid sequence, but may exhibit substantial identity.

By "substantially identical" or "substantially homologous" is meant a polypeptide or nucleic acid molecule exhibiting at least about 50% identical or homologous to a reference amino acid sequence (for example, any one of the amino acid sequences described herein) or a reference nucleic acid sequence (for example, any one of the nucleic acid sequences described herein). In certain embodiments, such a sequence is at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identical or homologous to the amino acid sequence or nucleic acid sequence used for comparison.

The percent identity between the two sequences is a function of the number of identical positions shared by the sequences (i.e., % homology= #of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm.

Sequence identity can be measured by using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/

PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

The percent homology or identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology or identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the amino acids sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215: 403-10. BLAST protein searches can be performed with the XBLAST program, score=50, wordlength=3 to obtain amino acid sequences homologous to the specified sequences (e.g., heavy and light chain variable region sequences of scFv m903, m904, m905, m906, and m900) disclosed herein. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used.

An "effective amount" is an amount sufficient to affect a beneficial or desired clinical result upon treatment. An effective amount can be administered to a subject in one or more doses. In certain embodiments, an effective amount can be an amount that is sufficient to palliate, ameliorate, stabilize, reverse or slow the progression of the disease, or otherwise reduce the pathological consequences of the disease. The effective amount can be determined by a physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the cells administered.

By "modulate" is meant positively or negatively alter. Exemplary modulations include a about 1%, about 2%, about 5%, about 10%, about 25%, about 50%, about 75%, or about 100% change.

By "increase" is meant to alter positively by at least about 5%. An alteration may be by about 5%, about 10%, about 25%, about 30%, about 50%, about 75%, about 100% or more.

By "reduce" is meant to alter negatively by at least about 5%. An alteration may be by about 5%, about 10%, about 25%, about 30%, about 50%, about 75%, or even by about 100%.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated cell" is meant a cell that is separated from the molecular and/or cellular components that naturally accompany the cell.

The term "antigen-binding domain" as used herein refers to a domain capable of specifically binding a particular antigenic determinant or set of antigenic determinants present on a cell.

By "neoplasm" is meant a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasm can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasia include cancers, such as sarcomas, carcinomas, or plasmacytomas (malignant tumor of the plasma cells).

By "signal sequence" or "leader sequence" is meant a peptide sequence (e.g., 5, 10, 15, 20, 25 or 30 amino acids) present at the N-terminus of newly synthesized proteins that directs their entry to the secretory pathway.

The terms "comprises", "comprising", and are intended to have the broad meaning ascribed to them in U.S. Patent Law and can mean "includes", "including" and the like.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys. The term "immunocompromised" as used herein refers to a subject who has an immunodeficiency. The subject is very vulnerable to opportunistic infections, infections caused by organisms that usually do not cause disease in a person with a healthy immune system but can affect people with a poorly functioning or suppressed immune system.

Other aspects of the presently disclosed subject matter are described in the following disclosure and are within the ambit of the presently disclosed subject matter.

5.2. Chimeric Antigen Receptor (CAR)

In certain embodiments, the present disclosure provides a chimeric antigen receptor (CAR) comprising an extracellular antigen-binding domain, a transmembrane domain, and an intracellular signaling domain comprising at least one co-stimulatory signaling domain that comprises a CD28 polypeptide comprising a mutated CD28 intracellular motif, i.e., a mutated YMNM motif.

CARs are engineered receptors, which graft or confer a specificity of interest onto an immune effector cell. CARs can be used to graft the specificity of a monoclonal antibody onto a T cell; with transfer of their coding sequence facilitated by retroviral vectors.

There are three generations of CARS. "First generation" CARs are typically composed of an extracellular antigen-binding domain (e.g., a scFv), which is fused to a transmembrane domain, which is fused to cytoplasmic/intracellular signaling domain. "First generation" CARs can provide de novo antigen recognition and cause activation of both $CD4^+$ and $CD8^+$ T cells through their CD3ζ chain signaling domain in a single fusion molecule, independent of HLA-mediated antigen presentation. "Second generation" CARs add intracellular signaling domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-1BB) and activation (CD3ζ). "Third generation" CARs comprise those that provide multiple co-stimulation (e.g., CD28 and 4-1BB) and activation (CD3ζ). In certain embodiments, the antigen-recognizing receptor is a second-generation CAR. In certain embodiments, the CAR comprises an extracellular antigen-binding domain that binds to an antigen, a transmembrane domain, and an intracellular signaling domain, wherein the intracellular signaling domain comprises a co-stimulatory signaling domain. In certain embodiments, the CAR further comprises a hinger/spacer region. In certain embodiments, the antigen-recognizing receptor is a third generation CAR that comprises multiple co-stimulatory signaling domains.

In certain embodiments, the CAR can comprise an extracellular antigen-binding domain, a transmembrane domain, and an intracellular signaling domain, wherein the extracellular antigen-binding domain specifically binds to an antigen, which can be a tumor antigen or a pathogen antigen.

5.2.1. Antigens

In certain embodiments, the CAR binds to a tumor antigen or a pathogen antigen.

In certain embodiments, the CAR binds to a tumor antigen. Any tumor antigen (e.g., antigenic peptide) can be used in the tumor-related embodiments described herein. Sources of antigen include, but are not limited to, cancer proteins. The antigen can be expressed as a peptide or as an intact protein or portion thereof. The intact protein or a portion thereof can be native or mutagenized. In certain embodiments, the antigen is expressed in a tumor tissue. Non-limiting examples of tumor antigens include Mesothelin, AXL, TIM3, HVEM, CD19, MUC16, MUC1, CA1X, CEA, CD8, CD7, CD10, CD20, CD22, CD30, CLL1, CD33, CD34, CD38, CD41, CD44, CD49f, CD56, CD70, CD74, CD99, CD123, CD133, CD138, EGP-2, EGP-40, EpCAM, Erb-B (e.g., Erb-B2, Erb-B3, Erb-B4), FBP, Fetal acetylcholine receptor, folate receptor-α, GD2, GD3, HER-2, hTERT, IL-13R-α2, κ-light chain, KDR, LeY, L1 cell adhesion molecule, MAGE-A1, MAGEA3, CT83 (also known as KK-LC-1), p53, MART1,GP100, Proteinase3 (PR1), Tyrosinase, Survivin, hTERT, EphA2, NKG2D ligands, NY-ESO-1, oncofetal antigen (h5T4), PSCA, PSMA, ROR1, TAG-72, VEGF-R2, WT-1, BCMA, CD44V6, NKCS1, EGF1R, EGFR-VIII, ADGRE2, CCR1, LILRB2, PRAME, HPV E6 oncoprotein, and HPV E7 oncoprotein. In certain embodiments, the tumor antigen is CD19.

In certain embodiments, the CAR binds to a CD19 polypeptide. In certain embodiments, the CAR binds to a human CD19 polypeptide. In certain embodiments, the human CD19 polypeptide comprises the amino acid sequence set forth in SEQ ID NO: 1 or a portion thereof. SEQ ID NO: 1 is provided below.

```
                                      [SEQ ID NO: 1]
PEEPLVVKVEEGDNAVLQCLKGTSDGPTQQLTWSRESPLKPFLKLSLGLP

GLGIHMRPLAIWLFIFNVSQQMGGFYLCQPGPPSEKAWQPGWTVNVEGSG

ELFRWNVSDLGGLGCGLKNRSSEGPSSPSGKLMSPKLYVWAKDRPEIWEG

EPPCLPPRDSLNQSLSQDLTMAPGSTLWLSCGVPPDSVSRGPLSWTHVHP

KGPKSLLSLELKDDRPARDMWVMETGLLLPRATAQDAGKYYCHRGNLTMS

FHLEITARPVLWHWLLRTGGWK
```

In certain embodiments, the CAR binds to the extracellular domain of CD19 (e.g., human CD19).

In certain embodiments, the CAR binds to a pathogen antigen, e.g., for use in treating and/or preventing a pathogen infection or other infectious disease. Non-limiting examples of pathogens include a virus, bacteria, fungi, parasite and protozoa capable of causing disease.

Non-limiting examples of viruses include, Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g., vesicular stomatitis viruses, rabies viruses); Filoviridae (e.g., Ebola viruses); Paramyxoviridae (e.g., parainfluenza viruses, mumps virus, measles virus, respiratory syncytial virus); Orthomyxoviridae (e.g., influenza viruses); Bungaviridae (e.g. Hantaan viruses, bunga viruses, phleboviruses and Naira viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses), human papilloma virus (i.e. HPV), JC virus, Epstein Bar Virus, Merkel cell polyoma virus.

Non-limiting examples of bacteria include *Pasteurella, Staphylococci, Streptococcus, Escherichia coli, Pseudomonas species*, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia, Clostridium difficile*, and *Actinomyces israelli.*

In certain embodiments, the pathogen antigen is a viral antigen present in Cytomegalovirus (CMV), a viral antigen present in Epstein Barr Virus (EBV), a viral antigen present in Human Immunodeficiency Virus (HIV), or a viral antigen present in influenza virus.

5.2.2. Extracellular Antigen-Binding Domain of a CAR

In certain embodiments, the extracellular antigen-binding domain comprises an scFv. In certain embodiments, the scFv is a human scFv. In certain embodiments, the scFv is a humanized scFv. In certain embodiments, the scFv is a murine scFv. In certain embodiments, the scFv is identified by screening scFv phage library with an antigen-Fc fusion protein.

In certain embodiments, the extracellular antigen-binding domain comprises a Fab. In certain embodiments, the Fab is crosslinked. In certain embodiments, the extracellular antigen-binding domain comprises a $F(ab)_2$. Any of the foregoing molecules may be comprised in a fusion protein with a heterologous sequence to form the extracellular antigen-binding domain.

In certain embodiments, the extracellular antigen-binding domain of the CAR (e.g., an scFv) binds to an antigen with a dissociation constant ($K_d$) of about $1\times10^{-6}$ M or less. In certain embodiments, the Kais about $1\times10^{-6}$ M or less, about $1\times10^{-7}$ M or less, about $1\times10^{-8}$ M or less, or about $1\times10^{-9}$ M or less. In certain non-limiting embodiments, the Ka is about $1\times10^{-8}$ M or less. In certain non-limiting embodiments, the Kais about $1\times10^{-9}$ M or less.

Binding of the extracellular antigen-binding domain of the CAR can be confirmed by, for example, enzyme-linked immunosorbent assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or a scFv) specific for the complex of interest. For example, the scFv can be radioactively labeled and used in a radioimmunoassay (RIA) (see, for example, Weintraub, B., Principles of Radioimmunoassays, Seventh Training Course on Radioligand Assay Techniques, The Endocrine Society, March 1986, which is incorporated by reference herein). The radioactive isotope can be detected by such means as the use of a $\gamma$ counter or a scintillation counter or by autoradiography. In certain embodiments, the extracellular antigen-binding domain is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet). In one embodiment, the human scFv is labeled with GFP.

In certain embodiments, the CDRs are identified according to the IMGT numbering system.

In certain embodiments, the extracellular antigen-binding domain of the CAR (e.g., an scFv) comprises or consists of the amino acid sequence set forth in SEQ ID NO: 2 and specifically binds to a CD19 polypeptide (e.g., a human CD19 polypeptide, e.g., a human CD19 polypeptide having the amino acid sequence SEQ ID NO: 1 or a portion thereof).

In certain embodiments, the extracellular antigen-binding domain of the CAR (e.g., an scFv) comprises a $V_H$ comprising an amino acid sequence that is at least about 80% (e.g., at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95% at least about 96%, at least about 97%, at least about 98%, or at least about 99%) homologous or identical to the amino acid sequence set forth in SEQ ID NO: 3. For example, the extracellular antigen-binding domain of the CAR (e.g., an scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 3. In certain embodiments, the extracellular antigen-binding domain comprises a $V_H$ comprising the amino acid sequence set forth in SEQ ID NO: 3. SEQ ID NO: 3 is provided in Table 1 below.

In certain embodiments, the extracellular antigen-binding domain of the CAR (e.g., an scFv) comprises a $V_L$ comprising an amino acid sequence that is at least about 80% (e.g., at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95% at least about 96%, at least about 97%, at least about 98%, or at least about 99%) homologous or identical to the amino acid sequence set forth in SEQ ID NO: 4. For example, the extracellular antigen-binding domain of the CAR (e.g., an scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 4. In certain embodiments, the extracellular antigen-binding domain comprises a $V_H$ comprising the amino acid sequence set forth in SEQ ID NO: 4. SEQ ID NO: 4 is provided in Table 1 below.

In certain embodiments, the extracellular antigen-binding domain of the CAR (e.g., an scFv) comprises a $V_H$ comprising the amino acid sequence set forth in SEQ ID NO: 3, and a $V_L$ comprising the amino acid sequence set forth in SEQ ID NO: 4. In certain embodiments, the $V_H$ and $V_L$ are linked via a linker. In certain embodiments, the linker comprises the amino acid sequence set forth in SEQ ID NO: 5. SEQ ID NO: 5 is provided below.

[SEQ ID NO: 5]
GGGGSGGGGSGGGGS

In certain embodiments, the extracellular antigen-binding domain of the CAR (e.g., an scFv) comprises a $V_H$ CDR1 comprising the amino acid sequence set forth in SEQ ID NO: 6 or a conservative modification thereof, a $V_H$ CDR2 comprising the amino acid sequence set forth in SEQ ID NO: 7 or a conservative modification thereof, and a $V_H$ CDR3 comprising the amino acid sequence set forth in SEQ ID NO: 8 or a conservative modification thereof. SEQ ID NOs: 6-8 are provided in Table 1.

In certain embodiments, the extracellular antigen-binding domain of the CAR (e.g., an scFv) comprises a $V_L$ CDR1 comprising the amino acid sequence set forth in SEQ ID NO: 9 or a conservative modification thereof, a $V_L$ CDR2 comprising the amino acid sequence set forth in SEQ ID NO: 10 or a conservative modification thereof, and a $V_L$ CDR3 comprising the amino acid sequence set forth in SEQ ID NO: 11 or a conservative modification thereof. SEQ ID NOs: 9-11 are provided in Table 1.

In certain embodiments, the extracellular antigen-binding domain of the CAR (e.g., an scFv) comprises a $V_H$ CDR1 comprising the amino acid sequence set forth in SEQ ID NO: 6 or a conservative modification thereof, a $V_H$ CDR2 comprising the amino acid sequence set forth in SEQ ID NO: 7 or a conservative modification thereof, a $V_H$ CDR3 comprising the amino acid sequence set forth in SEQ ID NO: 8 or a conservative modification thereof, a $V_L$ CDR1 comprising the amino acid sequence set forth in SEQ ID NO: 9 or a conservative modification thereof, a $V_L$ CDR2 comprising the amino acid sequence set forth in SEQ ID NO: 10 or a conservative modification, and a $V_L$ CDR3 comprising the amino acid sequence set forth in SEQ ID NO: 11 or a conservative modification thereof.

In certain embodiments, the extracellular antigen-binding domain of the CAR (e.g., an scFv) comprises a $V_H$ CDR1 comprising the amino acid sequence set forth in SEQ ID NO: 6, a $V_H$ CDR2 comprising the amino acid sequence set forth in SEQ ID NO: 7, a $V_H$ CDR3 comprising the amino acid sequence set forth in SEQ ID NO: 8, a $V_L$ CDR1 comprising the amino acid sequence set forth in SEQ ID NO: 9, a $V_L$ CDR2 comprising the amino acid sequence set forth in SEQ ID NO: 10, and a $V_L$ CDR3 comprising the amino acid sequence set forth in SEQ ID NO: 11.

TABLE 1

| Antigen | CD19 | | |
| --- | --- | --- | --- |
| CDRs | 1 | 2 | 3 |
| $V_H$ | GYAFSS [SEQ ID NO: 6] | YPGDGD [SEQ ID NO: 7] | KTISSWDF [SEQ ID NO: 8] |
| $V_L$ | NVGTNVA [SEQ ID NO: 9] | SATYRN [SEQ ID NO: 10] | FCQQYNRY [SEQ ID NO: 11] |
| Full $V_H$ | EVKLQQSGAELVRPGSSVKISCKASGYAFSSYWMNWVKQRPGQGLEWIGQIYPGDGDTNY NGKFKGQATLTADKSSSTAYMQLSGLTSEDSAVYFCARKTISSVVDFYFDYWGQGTTVTV SS [SEQ ID NO: 3] | | |
| Full $V_L$ | DIELTQSPKFMSTSVGDRVSVTCKASQNVGTNVAWYQQKPGQSPKPLIYSATYRNSGVPD RFTGSGSGTDFTLTITNVQSKDLADYFCQQYNRYPYTSGGGTKLEIKR [SEQ ID NO: 4] | | |
| scFv | EVKLQQSGAELVRPGSSVKISCKASGYAFSSYWMNWVKQRPGQGLEWIGQIYPGDGDTNY NGKFKGQATLTADKSSSTAYMQLSGLTSEDSAVYFCARKTISSVVDFYFDYWGQGTTVTV SSGGGGSGGGGSGGGGSDIELTQSPKFMSTSVGDRVSVTCKASQNVGTNVAWYQQKPGQS PKPLIYSATYRNSGVPDRFTGSGSGTDFTLTITNVQSKDLADYFCQQYNRYPYTSGGGTK LEIKR [SEQ ID NO: 2] | | |

As used herein, the term "a conservative sequence modification" refers to an amino acid modification that does not significantly affect or alter the binding characteristics of the presently disclosed CAR (e.g., the extracellular antigen-binding domain of the CAR) comprising the amino acid sequence. Conservative modifications can include amino acid substitutions, additions and deletions. Modifications can be introduced into the human scFv of the presently disclosed CAR by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (l) above) using the functional assays described herein. In certain embodiments, no more than one, no more than two, no more than three, no more than four, no more than five residues within a specified sequence or a CDR region are altered.

The $V_H$ and/or $V_L$ amino acid sequences having at least about 80%, at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homology or identity to a specific sequence (e.g., SEQ ID NOs: 3 and 4) may contain substitutions (e.g., conservative substitutions), insertions, or deletions relative to the specified sequence(s), but retain the ability to bind to a target antigen (e.g., CD19). In certain embodiments, a total of 1 to 10 amino acids are substituted, inserted and/or deleted in a specific sequence (e.g., SEQ ID NOs: 3 and 4). In certain embodiments, substitutions, insertions, or deletions occur in regions outside the CDRs (e.g., in the FRs) of the extracellular antigen-binding domain. In certain embodiments, the extracellular antigen-binding domain comprises $V_H$ and/or $V_L$ sequence selected from the group consisting of SEQ ID NOs: 3 and 4, including post-translational modifications of that sequence (SEQ ID NOs: 3 and 4).

5.2.3. Transmembrane Domain of a CAR

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal are transmitted to the cell. In certain embodiments, the transmembrane domain of the CAR comprises a native or modified transmembrane domain of CD8, CD28, CD3ζ, CD4, 4-1BB, OX40, ICOS, CD84, CD166, CD8a, CD8b, ICAM-1, CTLA-4, CD27, CD40, NKGD2, or a combination thereof.

In certain embodiments, the transmembrane domain of the CAR comprises a CD28 polypeptide (e.g., a transmembrane domain of CD28 or a portion thereof). In certain embodiments, the transmembrane domain of the CAR comprises a transmembrane domain of human CD28 or a portion thereof. In certain embodiments, the CD28 polypeptide comprises or consists of an amino acid sequence that is at least about 85%, about 90%, about 95%, about 96%, about 97%, about 98%, about 99% or 100% homologous or identical to the amino acid sequence having a NCBI Reference No: NP_006130 (SEQ ID NO: 12), or a fragment thereof, and/or may optionally comprise up to one or up to two or up to three conservative amino acid substitutions. In certain embodiments, the CD28 polypeptide comprises or consists of an amino acid sequence that is a consecutive portion of SEQ ID NO: 12, which is at least 20, or at least 30, or at least 40, or at least 50, and up to 220 amino acids in length. In certain embodiments, the CD28 polypeptide comprises or consists of an amino acid sequence of amino acids 1 to 220, 1 to 50, 50 to 100, 100 to 150, 150 to 200, 153 to 179, or 200 to 220 of SEQ ID NO: 12. In certain embodiments, the transmembrane domain of the CAR comprises a CD28 polypeptide comprising or consisting of amino acids 153 to 179 of SEQ ID NO: 12. SEQ ID NO: 12 is provided below:

```
                                             [SEQ ID NO: 12]
  1 MLRLLLALNL FPSIQVTGNK ILVKQSPMLV AYDNAVNLSC
    KYSYNLFSRE FRASLHKGLD
 61 SAVEVCVVYG NYSQQLQVYS KTGFNCDGKL GNESVTFYLQ
    NLYVNQTDIY FCKIEVMYPP
121 PYLDNEKSNG TIIHVKGKHL CPSPLFPGPS KPFWVLVVVG
    GVLACYSLLV TVAFIIFWVR
181 SKRSRLLHSD YMNMTPRRPG PTRKHYQPYA PPRDFAAYRS
```

An exemplary nucleotide sequence encoding the amino acid 153 to 179 of SEQ ID NO: 12 is set forth in SEQ ID NO: 13, which is provided below.

```
                                             [SEQ ID NO: 13]
TTTTGGGTGCTGGTGGTGGTTGGTGGAGTCCTGGCTTGCTATAGCTTGCT
AGTAACAGTGGCCTTTATTATTTTCTGGGTG
```

In certain embodiments, the transmembrane domain of the CAR comprises a transmembrane domain of mouse CD28 or a portion thereof. In certain embodiments, the CD28 polypeptide comprises or consists of an amino acid sequence that is at least about 85%, about 90%, about 95%, about 96%, about 97%, about 98%, about 99% or 100% homologous or identical to the sequence having a NCBI Reference No: NP_031668.3 (SEQ ID NO: 14), or a fragment thereof, and/or may optionally comprise up to one or up to two or up to three conservative amino acid substitutions. In non-limiting certain embodiments, the CD28 polypeptide comprises or consists of an amino acid sequence that is a consecutive portion of SEQ ID NO: 14, which is at least 20, or at least 30, or at least 40, or at least 50, and up to 218 amino acids in length. In certain embodiments, the CD28 polypeptide comprises or consists of an amino acid sequence of amino acids 1 to 220, 1 to 50, 50 to 100, 100 to 150, 150 to 200, 151 to 177, or 200 to 218 of SEQ ID NO: 14. In certain embodiments, the transmembrane domain of the CAR comprises a CD28 polypeptide comprising or consisting of amino acids 151 to 177 of SEQ ID NO: 14. SEQ ID NO: 14 is provided below:

```
                                              [SEQ ID NO: 14]
  1  MTLRLLFLAL NFFSVQVTEN KILVKQSPLL VVDSNEVSLS
     CRYSYNLLAK EFRASLYKGV
 61  NSDVEVCVGN GNFTYQPQFR SNAEFNCDGD FDNETVTFRL
     WNLHVNHTDI YFCKIEFMYP
121  PPYLDNERSN GTIIHIKEKH LCHTQSSPKL FWALVVVAGV
     LFCYGLLVTV ALCVIWTNSR
181  RNRLLQSDYM NMTPRRPGLT RKPYQPYAPA RDFAAYRP
```

In certain embodiments, the transmembrane domain of the CAR comprises a CD8 polypeptide (e.g., a transmembrane domain of CD8 or a portion thereof). In certain embodiments, the transmembrane domain of the CAR comprises a transmembrane domain of human CD8 or a portion thereof. In certain embodiments, the CD8 polypeptide comprises or consists of an amino acid sequence that is at least about 85%, about 90%, about 95%, about 96%, about 97%, about 98%, about 99% or about 100% homologous or identical to the sequence having a NCBI Reference No: NP_001139345.1 (SEQ ID NO: 15), or a fragment thereof, and/or may optionally comprise up to one or up to two or up to three conservative amino acid substitutions. In certain embodiments, the CD8 polypeptide comprises or consists of an amino acid sequence that is a consecutive portion of SEQ ID NO: 15, which is at least 20, or at least 30, or at least 40, or at least 50, and up to 235 amino acids in length. In certain embodiments, the CD8 polypeptide comprises or has an amino acid sequence of amino acids 1 to 235, 1 to 50, 50 to 100, 100 to 150, 150 to 200, 137 to 209, or 200 to 235 of SEQ ID NO: 15. In certain embodiments, the transmembrane domain of the CAR comprises a CD8 polypeptide comprising or consisting of amino acids 137 to 209 of SEQ ID NO: 15. SEQ ID NO: 15 is provided below.

```
                                              [SEQ ID NO: 15]
MALPVTALLLPLALLLHAARPSQFRVSPLDRTWNLGETVELKCQVLLSNP
TSGCSWLFQPRGAAASPTFLLYLSQNKPKAAEGLDTQRFSGKRLGDTFVL
TLSDFRRENEGYYFCSALSNSIMYFSHFVPVFLPAKPTTTPAPRPPTPAP
TIASQPLSLRPEACRPAAGGAVHTRGLDFACDIYIWAPLAGTCGVLLLSL
VITLYCNHRNRRRVCKCPRPVVKSGDKPSLSARYV
```

In certain embodiments, the transmembrane domain of the CAR comprises a transmembrane domain of mouse CD8 or a portion thereof. In certain embodiments, the CD8 polypeptide comprises or consists of an amino acid sequence that is at least about 85%, about 90%, about 95%, about 96%, about 97%, about 98%, about 99% or about 100% homologous or identical to the sequence having a NCBI Reference No: AAA92533.1 (SEQ ID NO: 16), or a fragment thereof, and/or may optionally comprise up to one or up to two or up to three conservative amino acid substitutions. In certain embodiments, the CD8 polypeptide comprises or consists of an amino acid sequence that is a consecutive portion of SEQ ID NO: 16, which is at least about 20, or at least about 30, or at least about 40, or at least about 50, or at least about 60, or at least about 70, or at least about 100, or at least about 200, and up to 247 amino acids in length. In certain embodiments, the CD8 polypeptide comprises or has an amino acid sequence of amino acids 1 to 247, 1 to 50, 50 to 100, 100 to 150, 150 to 200, 151 to 219, or 200 to 247 of SEQ ID NO: 16. In certain embodiments, the transmembrane domain of the CAR comprises a CD8 polypeptide comprising or consisting of amino acids 151 to 219 of SEQ ID NO: 16. SEQ ID NO: 16 is provided below.

```
                                              [SEQ ID NO: 16]
  1  MASPLTRFLS LNLLLMGESI ILGSGEAKPQ APELRIFPKK
     MDAELGQKVD LVCEVLGSVS
 61  QGCSWLFQNS SSKLPQPTFV VYMASSHNKI TWDEKLNSSK
     LFSAVRDTNN KYVLTLNKFS
121  KENEGYYFCS VISNSVMYFS SVVPVLQKVN STTTKPVLRT
     PSPVHPTGTS QPQRPEDCRP
181  RGSVKGTGLD FACDIYIWAP LAGICVAPLL SLIITLICYH
     RSRKRVCKCP RPLVRQEGKP
241  RPSEKIV
```

In certain embodiments, the CAR further comprises a spacer region that links the extracellular antigen-binding domain to the transmembrane domain. The spacer region can be flexible enough to allow the antigen binding domain to orient in different directions to facilitate antigen recognition while preserving the activating activity of the CAR.

In certain embodiments, the hinge/spacer region of the CAR comprises a native or modified hinge region of CD8, CD28, CD3ζ, CD40, 4-1BB, OX40, CD84, CD166, CD8a, CD8b, ICOS, ICAM-1, CTLA-4, CD27, CD40, NKGD2, a synthetic polypeptide (not based on a protein associated with the immune response), or a combination thereof. The hinge/spacer region can be the hinge region from IgG1, or the $CH_2CH_3$ region of immunoglobulin and portions of CD3, a portion of a CD28 polypeptide (e.g., a portion of SEQ ID NO: 12 or 14), a portion of a CD8 polypeptide (e.g., a portion of SEQ ID NO: 15 or 16), a variation of any of the foregoing which is at least about 80%, at least about 85%, at least about 90%, at least about 95%, or at least about 100% homologous or identical thereto, or a synthetic spacer sequence.

5.2.4. Intracellular Signaling Domain of a CAR

In certain embodiments, the CAR comprises an intracellular signaling domain. In certain embodiments, the intracellular signaling domain of the CAR comprises a CD3ζ polypeptide. CD3ζ can activate or stimulate a cell (e.g., a cell of the lymphoid lineage, e.g., a T cell). Wild type ("native") CD3ζ comprises three functional immunoreceptor tyrosine-based activation motifs (ITAMs), three functional basic-rich stretch (BRS) regions (BRS1, BRS2 and BRS3). CD3ζ transmits an activation signal to the cell (e.g., a cell of the lymphoid lineage, e.g., a T cell) after antigen is bound. The intracellular signaling domain of the CD32-chain is the primary transmitter of signals from endogenous TCRs.

In certain embodiments, the intracellular signaling domain of the CAR comprises a native CD32. In certain embodiments, the CD32 polypeptide comprises or consists of an amino acid sequence that is at least about 85%, about 90%, about 95%, about 96%, about 97%, about 98%, about 99% or about 100% homologous or identical to the sequence having a NCBI Reference No: NP_932170 (SEQ ID NO: 17), or a fragment thereof, and/or may optionally comprise up to one or up to two or up to three conservative amino acid substitutions. In certain embodiments, the CD3ζ polypeptide comprises or consists of an amino acid sequence that is a consecutive portion of SEQ ID NO: 17, which is at least 20, or at least 30, or at least 40, or at least 50, and up to 164 amino acids in length. In certain embodiments, the CD3ζ polypeptide comprises or consists of an amino acid sequence of amino acids 1 to 164, 1 to 50, 50 to 100, 52 to 164, 100 to 150, or 150 to 164 of SEQ ID NO: 17. In certain embodiments, the intracellular signaling domain of the CAR comprises a CD3ζ polypeptide comprising or consisting of amino acids 52 to 164 of SEQ ID NO: 17. SEQ ID NO: 17 is provided below:

```
                                       [SEQ ID NO: 17]
  1  MKWKALFTAA ILQAQLPITE AQSFGLLDPK LCYLLDGILF
     IYGVILTALF LRVKFSRSAD
 61  APAYQQGQNQ LYNELNLGRR EEYDVLDKRR GRDPEMGGKP
     QRRKNPQEGL YNELQKDKMA
121  EAYSEIGMKG ERRRGKGHDG LYQGLSTATK DTYDALHMQA
     LPPR
```

In certain embodiments, the intracellular signaling domain of the CAR comprises a CD3ζ polypeptide comprising or consisting of the amino acid sequence set forth in SEQ ID NO: 18. SEQ ID NO: 18 is provided below.

```
                                       [SEQ ID NO: 18]
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR
```

In certain embodiments, the intracellular signaling domain of the CAR further comprises at least one co-stimulatory signaling domain. In certain embodiments, the at least one co-stimulatory signaling domain comprises at least one co-stimulatory molecule or a portion thereof. In certain embodiments, the at least one co-stimulatory signaling domain comprises an intracellular domain of at least one co-stimulatory molecule or a portion thereof.

As used herein, a "co-stimulatory molecule" refers to a cell surface molecule other than antigen receptor or its ligand that can provide an efficient response of lymphocytes to an antigen. In certain embodiments, a co-stimulatory molecule can provide optimal lymphocyte activation. Non-limiting examples of co-stimulatory molecules include CD28, 4-1BB, OX40, ICOS, DAP-10, CD27, CD40, NKGD2, CD2, FN14, HVEM, LTBR, CD28H, TNFR1, TNFR2, BAFF-R, BCMA, TACI, TROY, RANK, CD40, CD27, CD30, EDAR, XEDAR, GITR, DR6, and NGFR, and combinations thereof. The co-stimulatory molecule can bind to a co-stimulatory ligand, which is a protein expressed on cell surface that upon binding to its receptor produces a co-stimulatory response, i.e., an intracellular response that effects the stimulation provided when a CAR binds to its target antigen.

In certain embodiments, the at least one co-stimulatory signaling domain comprises a CD28 polypeptide comprising a mutated YMNM motif.

CD28 is a transmembrane protein that plays a critical role in T cell activation through its function as a costimulatory molecule. CD28 is also known as cluster of differentiation 28, Tp44, and CD28 molecule. CD28 possesses an intracellular domain, which comprises intracellular motifs that are critical for the effective signaling of CD28. In certain embodiments, the CD28 intracellular domain comprises intracellular subdomains (also known as "intracellular motifs") that regulate signaling pathways post TCR-stimulation.

CD28 includes three intracellular motifs: a YMNM motif, and two proline-rick motifs: PRRP motif, and PYAP motif. The CD28 intracellular motifs can serve as docking sites for a number of adaptor molecules that interact with these motifs through their SH2 or SH3 domains. Such interaction transduces downstream signals terminating on transcription factors that regulate gene expression. For example, a native YMNM motif binds to a p85 subunit of a phosphoinositide 3-kinase (PI3K). A native YMNM motif also binds to growth factor receptor-bound protein 2 (Grb2) and/or Grb2-related adaptor protein 2 (GADS). Grb2 binds to Gab1 and Gab2, which in turn can recruit the p85 subunit of a PI3K.

In certain embodiments, a native YMNM motif consists of the amino acid sequence set forth in YMNM (SEQ ID NO: 19). In certain embodiments, a native YMNM motif binds to the p85 subunit of PI3K via a consensus sequence YMxM (SEQ ID NO: 20), wherein x is not an aspartic acid (N). In certain embodiments, a native YMNM motif binds to Grb2 and/or GADs via a consensus sequence YxNx (SEQ ID NO: 21), wherein x is not a methionine (M).

In certain embodiments, the CD28 polypeptide comprising a presently disclosed mutated YMNM motif has reduced recruitment of the p85 subunit of a PI3K as compared to a CD28 molecule comprising a native YMNM motif.

In certain embodiments, the p85 subunit of a PI3K does not bind to the mutated YMNM motif, thereby reducing the recruitment of the p85 subunit of a PI3K to the CD28 polypeptide. The mutated YMNM motif that blocks the binding of the p85 subunit of a PI3K retains its binding to Grb2 and/or GADS. Thus, downstream signaling of Grb2/GADS remains intact, e.g., downstream signaling leading to IL-2 secretion remains intact. Such mutated YMNM motif is referred to as "GADS/Grb2-permitting mutant".

In certain embodiments, the mutated YMNM binds to the p85 subunit of a PI3K, but does not bind to Grb2 and/or GADS. Since the binding of PI3K p85 is retained, the downstream signaling of PI3K retains intact. Since the binding of Grb2/GADS is blocked, the recruitment of PI3K p85 subunit, which is triggered by the binding of Grb2 to Gab1 and Gab2, is reduced or blocked. In addition, the downstream signaling of Grb2/GADS is blocked. Such mutated YMNM motif is referred to as "PI3K-permissive mutant".

In certain embodiments, the mutated YMNM does not bind to the p85 subunit of a PI3K, and does not bind to Grb2 and/or GADS. Such mutated YMNM motif is referred to as "non-functional mutant". Non-functional mutants do not provide binding of PI3K, Grb2, or GADS to CD28 at the YMNM motif, but do not preclude these signaling molecules from binding elsewhere in the CD28 molecule.

In certain embodiments, the mutated YMNM retains only one methionine residue of the two methionine residues present in the YMNM motif i.e. YMxx or YxxM. These motifs potentially modulate signaling via PI3K by limiting how many methionine residues can bind the p85 subunit of PI3K. Such mutated YMNM motif is referred to as "hybrid 'HEMI' mutant".

5.2.4.1. GADS/Grb-2 Permitting Mutants

In certain embodiments, the mutated YMNM motif is a GADS/Grb-2 permitting mutant. In certain embodiments, the mutated YMNM motif consists of the amino acid sequence set forth in YxNx (SEQ ID NO: 21), wherein x is not a methionine (M). In certain embodiments, x is selected from the group consisting of amino acids A, R, N, D, C, E, Q, G, H, I, K, F, P, S, T, W, Y, V, and L. In certain embodiments, the mutated YMNM motif consists of the amino acid sequence set forth in YENV (SEQ ID NO: 22), YSNV (SEQ ID NO: 23), YKNL (SEQ ID NO: 24), YENQ (SEQ ID NO: 25), YKNI (SEQ ID NO: 26), YINQ (SEQ ID NO: 27), YHNK (SEQ ID NO: 28), YVNQ (SEQ ID NO: 29), YLNP (SEQ ID NO: 30), YLNT (SEQ ID NO: 31), YDND (SEQ ID NO: 66), YENI (SEQ ID NO: 67), YENL (SEQ ID NO: 68), YKNQ (SEQ ID NO: 72), YKNV (SEQ ID NO: 73), or YANG (SEQ ID NO: 87). In certain embodiments, the mutated YMNM motif consists of the amino acid sequence set forth in YSNV (SEQ ID NO: 23). In certain embodiments, the mutated YMNM motif consists of the amino acid sequence set forth in YKNI (SEQ ID NO: 26). In certain embodiments, the mutated YMNM motif consists of the amino acid sequence set forth in YENV (SEQ ID NO: 22). In certain embodiments, the mutated YMNM motif consists of the amino acid sequence set forth in YKNL (SEQ ID NO: 24).

5.2.4.2. PI3K-Permissive Mutants

In certain embodiments, the mutated YMNM motif is a PI3K-permissive mutant. In certain embodiments, the mutated YMNM motif consists of the amino acid sequence set forth in YMxM (SEQ ID NO: 20), wherein x is not an aspartic acid (N). In certain embodiments, x is selected from the group consisting of amino acids A, R, D, C, E, Q, G, H, I, K, M, F, P, S, T, W, Y, V, and L. In certain embodiments, the mutated YMNM motif consists of the amino acid sequence set forth in YMDM (SEQ ID NO: 32), YMPM (SEQ ID NO: 79), YMRM (SEQ ID NO: 37), or YMSM (SEQ ID NO: 80). In certain embodiments, the mutated YMNM motif consists of the amino acid sequence set forth in YMDM (SEQ ID NO: 32).

In certain embodiments, the mutated YMNM motif consists of the amino acid sequence set forth in YbxM (SEQ ID NO: 33), wherein x is not an aspartic acid (N), and b is not a methionine (M). In certain embodiments, x is selected from the group consisting of amino acids A, R, D, C, E, Q, G, H, I, K, M, F, P, S, T, W, Y, V, and L. In certain embodiments, b is selected from the group consisting of amino acids A, R, N, C, E, Q, G, H, I, K, N, F, P, S, T, W, Y, V, and L. In certain embodiments, the mutated YMNM motif consists of the amino acid sequence set forth in YTHM (SEQ ID NO: 34) YVLM (SEQ ID NO: 35), YIAM (SEQ ID NO: 36), YVEM (SEQ ID NO: 83), YVKM (SEQ ID NO: 85), or YVPM (SEQ ID NO: 86).

In certain embodiments, the mutated YMNM motif consists of the amino acid sequence set forth in YMxb (SEQ ID NO: 65), wherein x is not an aspartic acid (N), and b is not a methionine (M). In certain embodiments, x is selected from the group consisting of amino acids A, R, D, C, E, Q, G, H, I, K, M, F, P, S, T, W, Y, V, and L. In certain embodiments, b is selected from the group consisting of amino acids A, R, N, C, E, Q, G, H, I, K, N, F, P, S, T, W, Y, V, and L. In certain embodiments, the mutated YMNM motif consists of the amino acid sequence set forth in YMAP (SEQ ID NO: 77).

Certain mutated YMNM motifs are described in Mol Cell Proteomics. 2010 November;9 (11): 2391-404; Virology. 2015 May; 0:568-577, both of which are incorporated by reference herein in its entirety.

5.2.4.3. Hybrid ‘HEMI’ Mutants

In certain embodiments, the mutated YMNM motif is a hybrid ‘HEMI’ mutant. In certain embodiments, the mutated YMNM motif consists of the amino acid sequence set forth in YMNx (SEQ ID NO: 38) or YxNM (SEQ ID NO: 39), wherein x is not a methionine (M). In certain embodiments, x is selected from the group consisting of amino acids A, R, N, C, E, Q, G, H, I, K, N, F, P, S, T, W, Y, V, and L. In certain embodiments, the mutated YMNM motif consists of the amino acid sequence set forth in YMNV (SEQ ID NO: 40), YENM (SEQ ID NO: 41), YMNQ (SEQ ID NO: 42), YMNL (SEQ ID NO: 78), or YSNM (SEQ ID NO: 81).

5.2.4.4. Non-Functional Mutants

In certain embodiments, the mutated YMNM motif is a non-functional mutant. In certain embodiments, the mutated YMNM motif consists of the amino acid sequence Ybxb (SEQ ID NO: 43), wherein x is not an aspartic acid (N), and b is not a methionine (M). In certain embodiments, x is selected from the group consisting of A, R, D, C, E, Q, G, H, I, K, M, F, P, S, T, W, Y, V, and L. In certain embodiments, b is selected from the group consisting of A, R, N, D, C, E, Q, G, H, I, K, F, P, S, T, W, Y, V, and L. In certain embodiments, the mutated YMNM motif consists of the amino acid sequence set forth in YGGG (SEQ ID NO: 44), YAAA (SEQ ID NO: 45), YFFF (SEQ ID NO: 46), YETV (SEQ ID NO: 69), YQQQ (SEQ ID NO: 70), YHAE (SEQ ID NO: 71), YLDL (SEQ ID NO: 74), YLIP (SEQ ID NO: 75), YLRV (SEQ ID NO: 76), YTAV (SEQ ID NO: 82), or YVHV (SEQ ID NO: 84). In certain embodiments, the mutated YMNM motif consists of the amino acid sequence set forth in YGGG (SEQ ID NO: 44).

In certain embodiments, the intracellular signaling domain of the CAR comprises a co-stimulatory signaling domain that comprises a CD28 polypeptide comprising a mutated YMNM motif consisting of the amino acid sequence set forth in YENV (SEQ ID NO: 22), wherein the CD28 polypeptide consists of the amino acid sequence set forth in SEQ ID NO: 47. SEQ ID NO: 47 is provided below.

```
                                        [SEQ ID NO: 47]
RSKRSRLLHSDYENVTPRRPGPTRKHYQPYAPPRDFAAYRS
```

In certain embodiments, the intracellular signaling domain of the CAR comprises a co-stimulatory signaling domain that comprises a CD28 polypeptide comprising a mutated YMNM motif consisting of the amino acid sequence set forth in YKNI (SEQ ID NO: 26), wherein the CD28 polypeptide consists of the amino acid sequence set forth in SEQ ID NO: 48. SEQ ID NO: 48 is provided below.

```
                                        [SEQ ID NO: 48]
RSKRSRLLHSDYKNITPRRPGPTRKHYQPYAPPRDFAAYRS
```

In certain embodiments, the intracellular signaling domain of the CAR comprises a co-stimulatory signaling domain that comprises a CD28 polypeptide comprising a mutated YMNM motif consisting of the amino acid sequence set forth in YMDM (SEQ ID NO: 32), wherein the CD28 polypeptide consists of the amino acid sequence set forth in SEQ ID NO: 49. EQ ID NO: 49 is provided below.

[SEQ ID NO: 49]
RSKRSRLLHSDYMDMTPRRPGPTRKHYQPYAPPRDFAAYRS

In certain embodiments, the intracellular signaling domain of the CAR comprises a co-stimulatory signaling domain that comprises a CD28 polypeptide comprising a mutated YMNM motif consisting of the amino acid sequence set forth in YGGG (SEQ ID NO: 44), wherein the CD28 polypeptide consists of the amino acid sequence set forth in SEQ ID NO: 63. EQ ID NO: 63 is provided below.

[SEQ ID NO: 63]
RSKRSRLLHSDYGGGTPRRPGPTRKHYQPYAPPRDFAAYRS

In certain embodiments, the intracellular signaling domain of the CAR comprises a co-stimulatory signaling domain that comprises a CD28 polypeptide comprising a mutated YMNM motif consisting of the amino acid sequence set forth in YSNV (SEQ ID NO: 23), wherein the CD28 polypeptide consists of the amino acid sequence set forth in SEQ ID NO: 64. EQ ID NO: 64 is provided below.

[SEQ ID NO: 64]
RSKRSRLLHSDYSNVTPRRPGPTRKHYQPYAPPRDFAAYRS

In certain embodiments, the intracellular signaling domain of the CAR comprises a first co-stimulatory signaling domain that comprises a CD28 polypeptide comprising a mutated YMNM motif (as disclosed herein), and a second co-stimulatory signaling domain that comprises an intracellular domain of a co-stimulatory molecule. In certain embodiments, the co-stimulatory molecule is selected from the group consisting of 4-1BB, OX40, ICOS, DAP-10, CD30, CD271, BAFFR, BCMA, DR3, FN14, HVEM, LTBR, RANK, TACI, TNFR1, TNFR2, TROY, EPOR, ILIRAcP, IL18R1, IL18RAP, ST2, and combinations thereof.

In certain embodiments, the second co-stimulatory signaling domain comprises a 4-1BB polypeptide (e.g., an intracellular domain of 4-1BB or a portion thereof). In certain embodiments, the 4-1BB polypeptide comprises or consists of an amino acid sequence that is at least about 80%, at least about 85%, at least about 90%, at least about 95%, at least about 96%, at least about 97%, at least about 98%, or at least about 99%, at least about 100% homologous or identical to the amino acid sequence having a NCBI Ref. No.: NP_001552 (SEQ ID NO: 50), or a fragment thereof, and/or may optionally comprise up to one or up to two or up to three conservative amino acid substitutions. In certain embodiments, the 4-1BB polypeptide comprises or consists of an amino acid sequence that is a consecutive portion of SEQ ID NO: 50, which is at least 20, or at least 30, or at least 40, or at least 50, or at least 100, or at least 150, or at least 150, and up to 255 amino acids in length. In certain embodiments, the 4-1BB polypeptide comprises or consists of an amino acid sequence of amino acids 1 to 255, 1 to 50, 50 to 100, 100 to 150, 150 to 200, 214 to 255, or 200 to 255 of SEQ ID NO: 50. SEQ ID NO: 50 is provided below.

[SEQ ID NO: 50]

```
1   MGNSCYNIVA TLLLVLNFER TRSLQDPCSN CPAGTFCDNN
    RNQICSPCPP NSFSSAGGQR
```

-continued

```
61  TCDICRQCKG VFRTRKECSS TSNAECDCTP GFHCLGAGCS
    MCEQDCKQGQ ELTKKGCKDC
121 CFGTFNDQKR GICRPWTNCS LDGKSVLVNG TKERDVVCGP
    SPADLSPGAS SVTPPAPARE
181 PGHSPQIISF FLALTSTALL FLLFFLTLRF SVVKRGRKKL
    LYIFKQPFMR PVQTTQEEDG
241 CSCRFPEEEE GGCEL
```

5.2.5. Exemplified CARs

In certain embodiments, the CAR is a CD19-targeted CAR. In certain embodiments, the CAR comprises (a) an extracellular antigen-binding domain that binds to human CD19 and comprises a $V_H$ CDR1 comprising the amino acid sequence set forth in SEQ ID NO: 6, a $V_H$ CDR2 comprising the amino acid sequence set forth in SEQ ID NO: 7, a $V_H$ CDR3 comprising the amino acid sequence set forth in SEQ ID NO: 8, a $V_L$ CDR1 comprising the amino acid sequence set forth in SEQ ID NO: 9, a $V_L$ CDR2 comprising the amino acid sequence set forth in SEQ ID NO: 10, and a $V_L$ CDR3 comprising the amino acid sequence set forth in SEQ ID NO: 11; (b) a transmembrane domain comprising a transmembrane domain of CD28 or a portion thereof, and (c) an intracellular signaling domain comprising (i) a CD32 polypeptide, and (ii) a co-stimulatory signaling domain that comprises a CD28 polypeptide comprising a mutated YMNM motif. In certain embodiments, the mutated YMNM motif consists of the amino acid sequence set forth in YMDM (SEQ ID NO: 32), YKNI (SEQ ID NO: 26), YENV (SEQ ID NO: 22), YSNV (SEQ ID NO: 23), YKNL (SEQ ID NO: 24), or YGGG (SEQ ID NO: 44). In certain embodiments, the $V_H$ and $V_L$ are linked via a linker having the amino acid sequence set forth in SEQ ID NO: 5.

In certain embodiments, an exemplary CD19-targeted CAR comprises a mutated YMNM motif consisting of the amino acid sequence set forth in YMDM (SEQ ID NO: 32). In certain embodiments, the exemplary CD19-targeted CAR consists of the amino acid sequence set forth in SEQ ID NO: 51, which is provided below.

[SEQ ID NO: 51]

```
EVKLQQSGAELVRPGSSVKISCKASGYAFSSYWMNWVKQRPGQGLEWIGQ
IYPGDGDTNYNGKFKGQATLTADKSSSTAYMQLSGLTSEDSAVYFCARKT
ISSVVDFYFDYWGQGTTVTVSSGGGGSGGGGSGGGGSDIELTQSPKFMST
SVGDRVSVTCKASQNVGTNVAWYQQKPGQSPKPLIYSATYRNSGVPDRFT
GSGSGTDFTLTITNVQSKDLADYFCQQYNRYPYTSGGGTKLEIKRAAAIE
VMYPPPYLDNEKSNGTIIHVKGKHLCPSPLFPGPSKPFWVLVVVGGVLAC
YSLLVTVAFIIFWVRSKRSRLLHSDYMDMTPRRPGPTRKHYQPYAPPRDF
AAYRSRVKFSRSADAPAYQQGQNQLYNELNLGRREEYDVLDKRRGRDPEM
GGKPRRKNPQEGLYNELQKDKMAEAYSEIGMKGERRRGKGHDGLYQGLST
ATKDTYDALHMQALPPR
```

An exemplary nucleotide sequence encoding the amino acid sequence of SEQ ID NO: 51 is set forth in SEQ ID NO: 52, which is provided below.

[SEQ ID NO: 52]
GAGGTGAAGCTGCAGCAGTCTGGGGCTGAGCTGGTGAGGCCTGGGTCCTC
AGTGAAGATTTCCTGCAAGGCTTCTGGCTATGCATTCAGTAGCTACTGGA
TGAACTGGGTGAAGCAGAGGCCTGGACAGGGTCTTGAGTGGATTGGACAG
ATTTATCCTGGAGATGGTGATACTAACTACAATGGAAAGTTCAAGGGTCA
AGCCACACTGACTGCAGACAAATCCTCCAGCACAGCCTACATGCAGCTCA
GCGGCCTAACATCTGAGGACTCTGCGGTCTATTTCTGTGCAAGAAAGACC
ATTAGTTCGGTAGTAGATTTCTACTTTGACTACTGGGGCCAAGGGACCAC
GGTCACCGTCTCCTCAGGTGGAGGTGGATCAGGTGGAGGTGGATCTGGTG
GAGGTGGATCTGACATTGAGCTCACCCAGTCTCCAAAATTCATGTCCACA
TCAGTAGGAGACAGGGTCAGCGTCACCTGCAAGGCCAGTCAGAATGTGGG
TACTAATGTAGCCTGGTATCAACAGAAACCAGGACAATCTCCTAAACCAC
TGATTTACTCGGCAACCTACCGGAACAGTGGAGTCCCTGATCGCTTCACA
GGCAGTGGATCTGGGACAGATTTCACTCTCACCATCACTAACGTGCAGTC
TAAAGACTTGGCAGACTATTTCTGTCAACAATATAACAGGTATCCGTACA
CGTCCGGAGGGGGGACCAAGCTGGAGATCAAACGGGCGGCCGCAATTGAA
GTTATGTATCCTCCTCCTTACCTAGACAATGAGAAGAGCAATGGAACCAT
TATCCATGTGAAAGGGAAACACCTTTGTCCAAGTCCCCTATTTCCCGGAC
CTTCTAAGCCCTTTTGGGTGCTGGTGGTGGTTGGTGGAGTCCTGGCTTGC
TATAGCTTGCTAGTAACAGTGGCCTTTATTATTTTCTGGGTGAGGAGTAA
GAGGAGCAGGCTCCTGCACAGTGACTACATGGATATGACTCCCCGCCGCC
CCGGGCCCACCCGCAAGCATTACCAGCCCTATGCCCCACCACGCGACTTC
GCAGCCTATCGCTCCAGAGTGAAGTTCAGCAGGAGCGCAGACGCCCCCGC
GTACCAGCAGGGCCAGAACCAGCTCTATAACGAGCTCAATCTAGGACGAA
GAGAGGAGTACGATGTTTTGGACAAGAGACGTGGCCGGGACCCTGAGATG
GGGGGAAAGCCGAGAAGGAAGAACCCTCAGGAAGGCCTGTACAATGAACT
GCAGAAAGATAAGATGGCGGAGGCCTACAGTGAGATTGGGATGAAAGGCG
AGCGCCGGAGGGGCAAGGGGCACGATGGCCTTTACCAGGGTCTCAGTACA
GCCACCAAGGACACCTACGACGCCCTTCACATGCAGGCCCTGCCCCCTCG
C

In certain embodiments, an exemplary CD19-targeted CAR comprises a mutated YMNM motif consisting of the amino acid sequence set forth in YENV (SEQ ID NO: 22). In certain embodiments, the exemplary CD19-targeted CAR consists of the amino acid sequence set forth in SEQ ID NO: 53, which is provided below.

[SEQ ID NO: 53]
EVKLQQSGAELVRPGSSVKISCKASGYAFSSYWMNWVKQRPGQGLEWIGQ
IYPGDGDTNYNGKFKGQATLTADKSSSTAYMQLSGLTSEDSAVYFCARKT
ISSVVDFYFDYWGQGTTVTVSSGGGGSGGGGSGGGGSDIELTQSPKFMST
SVGDRVSVTCKASQNVGTNVAWYQQKPGQSPKPLIYSATYRNSGVPDRET
GSGSGTDETLTITNVQSKDLADYFCQQYNRYPYTSGGGTKLEIKRAAAIE
VMYPPPYLDNEKSNGTIIHVKGKHLCPSPLFPGPSKPFWVLVVVGGVLAC

-continued

YSLLVTVAFIIFWVRSKRSRLLHSDYENVTPRRPGPTRKHYQPYAPPRDF
AAYRSRVKFSRSADAPAYQQGQNQLYNELNLGRREEYDVLDKRRGRDPEM
GGKPRRKNPQEGLYNELQKDKMAEAYSEIGMKGERRRGKGHDGLYQGLST
ATKDTYDALHMQALPPR

An exemplary nucleotide sequence encoding the amino acid sequence of SEQ ID NO: 53 is set forth in SEQ ID NO: 54, which is provided below.

[SEQ ID NO: 54]
GAGGTGAAGCTGCAGCAGTCTGGGGCTGAGCTGGTGAGGCCTGGGTCCTC
AGTGAAGATTTCCTGCAAGGCTTCTGGCTATGCATTCAGTAGCTACTGGA
TGAACTGGGTGAAGCAGAGGCCTGGACAGGGTCTTGAGTGGATTGGACAG
ATTTATCCTGGAGATGGTGATACTAACTACAATGGAAAGTTCAAGGGTCA
AGCCACACTGACTGCAGACAAATCCTCCAGCACAGCCTACATGCAGCTCA
GCGGCCTAACATCTGAGGACTCTGCGGTCTATTTCTGTGCAAGAAAGACC
ATTAGTTCGGTAGTAGATTTCTACTTTGACTACTGGGGCCAAGGGACCAC
GGTCACCGTCTCCTCAGGTGGAGGTGGATCAGGTGGAGGTGGATCTGGTG
GAGGTGGATCTGACATTGAGCTCACCCAGTCTCCAAAATTCATGTCCACA
TCAGTAGGAGACAGGGTCAGCGTCACCTGCAAGGCCAGTCAGAATGTGGG
TACTAATGTAGCCTGGTATCAACAGAAACCAGGACAATCTCCTAAACCAC
TGATTTACTCGGCAACCTACCGGAACAGTGGAGTCCCTGATCGCTTCACA
GGCAGTGGATCTGGGACAGATTTCACTCTCACCATCACTAACGTGCAGTC
TAAAGACTTGGCAGACTATTTCTGTCAACAATATAACAGGTATCCGTACA
CGTCCGGAGGGGGGACCAAGCTGGAGATCAAACGGGCGGCCGCAATTGAA
GTTATGTATCCTCCTCCTTACCTAGACAATGAGAAGAGCAATGGAACCAT
TATCCATGTGAAAGGGAAACACCTTTGTCCAAGTCCCCTATTTCCCGGAC
CTTCTAAGCCCTTTTGGGTGCTGGTGGTGGTTGGTGGAGTCCTGGCTTGC
TATAGCTTGCTAGTAACAGTGGCCTTTATTATTTTCTGGGTGAGGAGTAA
GAGGAGCAGGCTCCTGCACAGTGACTATGAAAATGTGACTCCCCGCCGCC
CCGGGCCCACCCGCAAGCATTACCAGCCCTATGCCCCACCACGCGACTTC
GCAGCCTATCGCTCCAGAGTGAAGTTCAGCAGGAGCGCAGACGCCCCCGC
GTACCAGCAGGGCCAGAACCAGCTCTATAACGAGCTCAATCTAGGACGAA
GAGAGGAGTACGATGTTTTGGACAAGAGACGTGGCCGGGACCCTGAGATG
GGGGGAAAGCCGAGAAGGAAGAACCCTCAGGAAGGCCTGTACAATGAACT
GCAGAAAGATAAGATGGCGGAGGCCTACAGTGAGATTGGGATGAAAGGCG
AGCGCCGGAGGGGCAAGGGGCACGATGGCCTTTACCAGGGTCTCAGTACA
GCCACCAAGGACACCTACGACGCCCTTCACATGCAGGCCCTGCCCCCTCG
CTAG

In certain embodiments, an exemplary CD19-targeted CAR comprises a mutated YMNM motif consisting of the amino acid sequence YKNI (SEQ ID NO: 26). In certain embodiments, the exemplary CD19-targeted CAR consists of the amino acid sequence set forth in SEQ ID NO: 55, which is provided below.

[SEQ ID NO: 55]
EVKLQQSGAELVRPGSSVKISCKASGYAFSSYWMNWVKQRPGQGLEWIGQ
IYPGDGDTNYNGKFKGQATLTADKSSSTAYMQLSGLTSEDSAVYFCARKT
ISSVVDFYFDYWGQGTTVTVSSGGGGSGGGGSGGGGSDIELTQSPKFMST
SVGDRVSVTCKASQNVGTNVAWYQQKPGQSPKPLIYSATYRNSGVPDRFT
GSGSGTDFTLTITNVQSKDLADYFCQQYNRYPYTSGGGTKLEIKRAAAIE
VMYPPPYLDNEKSNGTIIHVKGKHLCPSPLFPGPSKPFWVLVVVGGVLAC
YSLLVTVAFIIFWVRSKRSRLLHSDYKNITPRRPGPTRKHYQPYAPPRDF
AAYRSRVKFSRSADAPAYQQGQNQLYNELNLGRREEYDVLDKRRGRDPEM
GGKPRRKNPQEGLYNELQKDKMAEAYSEIGMKGERRRGKGHDGLYQGLST
ATKDTYDALHMQALPPR

An exemplary nucleotide sequence encoding the amino acid sequence of SEQ ID NO: 55 is set forth in SEQ ID NO: 56, which is provided below.

[SEQ ID NO: 56]
GAGGTGAAGCTGCAGCAGTCTGGGGCTGAGCTGGTGAGGCCTGGGTCCTC
AGTGAAGATTTCCTGCAAGGCTTCTGGCTATGCATTCAGTAGCTACTGGA
TGAACTGGGTGAAGCAGAGGCCTGGACAGGGTCTTGAGTGGATTGGACAG
ATTTATCCTGGAGATGGTGATACTAACTACAATGGAAAGTTCAAGGGTCA
AGCCACACTGACTGCAGACAAATCCTCCAGCACAGCCTACATGCAGCTCA
GCGGCCTAACATCTGAGGACTCTGCGGTCTATTTCTGTGCAAGAAAGACC
ATTAGTTCGGTAGTAGATTTCTACTTTGACTACTGGGGCCAAGGGACCAC
GGTCACCGTCTCCTCAGGTGGAGGTGGATCAGGTGGAGGTGGATCTGGTG
GAGGTGGATCTGACATTGAGCTCACCCAGTCTCCAAAATTCATGTCCACA
TCAGTAGGAGACAGGGTCAGCGTCACCTGCAAGGCCAGTCAGAATGTGGG
TACTAATGTAGCCTGGTATCAACAGAAACCAGGACAATCTCCTAAACCAC
TGATTTACTCGGCAACCTACCGGAACAGTGGAGTCCCTGATCGCTTCACA
GGCAGTGGATCTGGGACAGATTTCACTCTCACCATCACTAACGTGCAGTC
TAAAGACTTGGCAGACTATTTCTGTCAACAATATAACAGGTATCCGTACA
CGTCCGGAGGGGGGACCAAGCTGGAGATCAAACGGGCGGCCGCAATTGAA
GTTATGTATCCTCCTCCTTACCTAGACAATGAGAAGAGCAATGGAACCAT
TATCCATGTGAAAGGGAAACACCTTTGTCCAAGTCCCCTATTTCCCGGAC
CTTCTAAGCCCTTTTGGGTGCTGGTGGTGGTTGGTGGAGTCCTGGCTTGC
TATAGCTTGCTAGTAACAGTGGCCTTTATTATTTTCTGGGTGAGGAGTAA
GAGGAGCAGGCTCCTGCACAGTGACTATAAAAACATTACTCCCCGCCGCC
CCGGGCCCACCCGCAAGCATTACCAGCCCTATGCCCCACCACGCGACTTC
GCAGCCTATCGCTCCAGAGTGAAGTTCAGCAGGAGCGCAGACGCCCCCGC
GTACCAGCAGGGCCAGAACCAGCTCTATAACGAGCTCAATCTAGGACGAA
GAGAGGAGTACGATGTTTTGGACAAGAGACGTGGCCGGGACCCTGAGATG
GGGGGAAAGCCGAGAAGGAAGAACCCTCAGGAAGGCCTGTACAATGAACT
GCAGAAAGATAAGATGGCGGAGGCCTACAGTGAGATTGGGATGAAAGGCG

-continued

AGCGCCGGAGGGGCAAGGGGCACGATGGCCTTTACCAGGGTCTCAGTACA
GCCACCAAGGACACCTACGACGCCCTTCACATGCAGGCCCTGCCCCCTCG
C

In certain embodiments, an exemplary CD19-targeted CAR comprises a mutated YMNM motif consisting of the amino acid sequence YSNV (SEQ ID NO: 23). In certain embodiments, the exemplary CD19-targeted CAR consists of the amino acid sequence set forth in SEQ ID NO: 57, which is provided below.

[SEQ ID NO: 57]
EVKLQQSGAELVRPGSSVKISCKASGYAFSSYWMNWVKQRPGQGLEWIGQ
IYPGDGDTNYNGKFKGQATLTADKSSSTAYMQLSGLTSEDSAVYFCARKT
ISSVVDFYFDYWGQGTTVTVSSGGGGSGGGGSGGGGSDIELTQSPKFMST
SVGDRVSVTCKASQNVGTNVAWYQQKPGQSPKPLIYSATYRNSGVPDRFT
GSGSGTDFTLTITNVQSKDLADYFCQQYNRYPYTSGGGTKLEIKRAAAIE
VMYPPPYLDNEKSNGTIIHVKGKHLCPSPLFPGPSKPFWVLVVVGGVLAC
YSLLVTVAFIIFWVRSKRSRLLHSDYSNVTPRRPGPTRKHYQPYAPPRDF
AAYRSRVKFSRSADAPAYQQGQNQLYNELNLGRREEYDVLDKRRGRDPEM
GGKPRRKNPQEGLYNELQKDKMAEAYSEIGMKGERRRGKGHDGLYQGLST
ATKDTYDALHMQALPPR

An exemplary nucleotide sequence encoding the amino acid sequence of SEQ ID NO: 57 is set forth in SEQ ID NO: 58, which is provided below.

[SEQ ID NO: 58]
GAGGTGAAGCTGCAGCAGTCTGGGGCTGAGCTGGTGAGGCCTGGGTCCTC
AGTGAAGATTTCCTGCAAGGCTTCTGGCTATGCATTCAGTAGCTACTGGA
TGAACTGGGTGAAGCAGAGGCCTGGACAGGGTCTTGAGTGGATTGGACAG
ATTTATCCTGGAGATGGTGATACTAACTACAATGGAAAGTTCAAGGGTCA
AGCCACACTGACTGCAGACAAATCCTCCAGCACAGCCTACATGCAGCTCA
GCGGCCTAACATCTGAGGACTCTGCGGTCTATTTCTGTGCAAGAAAGACC
ATTAGTTCGGTAGTAGATTTCTACTTTGACTACTGGGGCCAAGGGACCAC
GGTCACCGTCTCCTCAGGTGGAGGTGGATCAGGTGGAGGTGGATCTGGTG
GAGGTGGATCTGACATTGAGCTCACCCAGTCTCCAAAATTCATGTCCACA
TCAGTAGGAGACAGGGTCAGCGTCACCTGCAAGGCCAGTCAGAATGTGGG
TACTAATGTAGCCTGGTATCAACAGAAACCAGGACAATCTCCTAAACCAC
TGATTTACTCGGCAACCTACCGGAACAGTGGAGTCCCTGATCGCTTCACA
GGCAGTGGATCTGGGACAGATTTCACTCTCACCATCACTAACGTGCAGTC
TAAAGACTTGGCAGACTATTTCTGTCAACAATATAACAGGTATCCGTACA
CGTCCGGAGGGGGGACCAAGCTGGAGATCAAACGGGCGGCCGCAATTGAA
GTTATGTATCCTCCTCCTTACCTAGACAATGAGAAGAGCAATGGAACCAT
TATCCATGTGAAAGGGAAACACCTTTGTCCAAGTCCCCTATTTCCCGGAC
CTTCTAAGCCCTTTTGGGTGCTGGTGGTGGTTGGTGGAGTCCTGGCTTGC
TATAGCTTGCTAGTAACAGTGGCCTTTATTATTTTCTGGGTGAGGAGTAA

GAGGAGCAGGCTCCTGCACAGTGACTACTCAAATGTTACTCCCCGCCGCC

CCGGGCCCACCCGCAAGCATTACCAGCCCTATGCCCCACCACGCGACTTC

GCAGCCTATCGCTCCAGAGTGAAGTTCAGCAGGAGCGCAGACGCCCCCGC

GTACCAGCAGGGCCAGAACCAGCTCTATAACGAGCTCAATCTAGGACGAA

GAGAGGAGTACGATGTTTTGGACAAGAGACGTGGCCGGGACCCTGAGATG

GGGGGAAAGCCGAGAAGGAAGAACCCTCAGGAAGGCCTGTACAATGAACT

GCAGAAAGATAAGATGGCGGAGGCCTACAGTGAGATTGGGATGAAAGGCG

AGCGCCGGAGGGGCAAGGGGCACGATGGCCTTTACCAGGGTCTCAGTACA

GCCACCAAGGACACCTACGACGCCCTTCACATGCAGGCCCTGCCCCCTCG

C

In certain embodiments, an exemplary CD19-targeted CAR comprises a mutated YMNM motif consisting of the amino acid sequence YKNL (SEQ ID NO: 24). In certain embodiments, the exemplary CD19-targeted CAR consists of the amino acid sequence set forth in SEQ ID NO: 59, which is provided below.

[SEQ ID NO: 59]

EVKLQQSGAELVRPGSSVKISCKASGYAFSSYWMNWVKQRPGQGLEWIGQ

IYPGDGDTNYNGKFKGQATLTADKSSSTAYMQLSGLTSEDSAVYFCARKT

ISSVVDFYFDYWGQGTTVTVSSGGGGSGGGGSGGGGSDIELTQSPKFMST

SVGDRVSVTCKASQNVGTNVAWYQQKPGQSPKPLIYSATYRNSGVPDRFT

GSGSGTDFTLTITNVQSKDLADYFCQQYNRYPYTSGGGTKLEIKRAAAIE

VMYPPPYLDNEKSNGTIIHVKGKHLCPSPLFPGPSKPFWVLVVVGGVLAC

YSLLVTVAFIIFWVRSKRSRLLHSDYKNLTPRRPGPTRKHYQPYAPPRDF

AAYRSRVKFSRSADAPAYQQGQNQLYNELNLGRREEYDVLDKRRGRDPEM

GGKPRRKNPQEGLYNELQKDKMAEAYSEIGMKGERRRGKGHDGLYQGLST

ATKDTYDALHMQALPPR

An exemplary nucleotide sequence encoding the amino acid sequence of SEQ ID NO: 59 is set forth in SEQ ID NO: 60, which is provided below.

[SEQ ID NO: 60]

GAGGTGAAGCTGCAGCAGTCTGGGGCTGAGCTGGTGAGGCCTGGGTCCTC

AGTGAAGATTTCCTGCAAGGCTTCTGGCTATGCATTCAGTAGCTACTGGA

TGAACTGGGTGAAGCAGAGGCCTGGACAGGGTCTTGAGTGGATTGGACAG

ATTTATCCTGGAGATGGTGATACTAACTACAATGGAAAGTTCAAGGGTCA

AGCCACACTGACTGCAGACAAATCCTCCAGCACAGCCTACATGCAGCTCA

GCGGCCTAACATCTGAGGACTCTGCGGTCTATTTCTGTGCAAGAAAGACC

ATTAGTTCGGTAGTAGATTTCTACTTTGACTACTGGGGCCAAGGGACCAC

GGTCACCGTCTCCTCAGGTGGAGGTGGATCAGGTGGAGGTGGATCTGGTG

GAGGTGGATCTGACATTGAGCTCACCCAGTCTCCAAAATTCATGTCCACA

TCAGTAGGAGACAGGGTCAGCGTCACCTGCAAGGCCAGTCAGAATGTGGG

TACTAATGTAGCCTGGTATCAACAGAAACCAGGACAATCTCCTAAACCAC

TGATTTACTCGGCAACCTACCGGAACAGTGGAGTCCCTGATCGCTTCACA

GGCAGTGGATCTGGGACAGATTTCACTCTCACCATCACTAACGTGCAGTC

TAAAGACTTGGCAGACTATTTCTGTCAACAATATAACAGGTATCCGTACA

CGTCCGGAGGGGGGACCAAGCTGGAGATCAAACGGGCGGCCGCAATTGAA

GTTATGTATCCTCCTCCTTACCTAGACAATGAGAAGAGCAATGGAACCAT

TATCCATGTGAAAGGGAAACACCTTTGTCCAAGTCCCCTATTTCCCGGAC

CTTCTAAGCCCTTTTGGGTGCTGGTGGTGGTTGGTGGAGTCCTGGCTTGC

TATAGCTTGCTAGTAACAGTGGCCTTTATTATTTTCTGGGTGAGGAGTAA

GAGGAGCAGGCTCCTGCACAGTGACTACAAAAACTTGACTCCCCGCCGCC

CCGGGCCCACCCGCAAGCATTACCAGCCCTATGCCCCACCACGCGACTTC

GCAGCCTATCGCTCCAGAGTGAAGTTCAGCAGGAGCGCAGACGCCCCCGC

GTACCAGCAGGGCCAGAACCAGCTCTATAACGAGCTCAATCTAGGACGAA

GAGAGGAGTACGATGTTTTGGACAAGAGACGTGGCCGGGACCCTGAGATG

GGGGGAAAGCCGAGAAGGAAGAACCCTCAGGAAGGCCTGTACAATGAACT

GCAGAAAGATAAGATGGCGGAGGCCTACAGTGAGATTGGGATGAAAGGCG

AGCGCCGGAGGGGCAAGGGGCACGATGGCCTTTACCAGGGTCTCAGTACA

GCCACCAAGGACACCTACGACGCCCTTCACATGCAGGCCCTGCCCCCTCG

C

In certain embodiments, an exemplary CD19-targeted CAR comprises a mutated YMNM motif consisting of the amino acid sequence YGGG (SEQ ID NO: 44). In certain embodiments, the exemplary CD19-targeted CAR consists of the amino acid sequence set forth in SEQ ID NO: 61, which is provided below.

[SEQ ID NO: 61]

EVKLQQSGAELVRPGSSVKISCKASGYAFSSYWMNWVKQRPGQGLEWIGQ

IYPGDGDTNYNGKFKGQATLTADKSSSTAYMQLSGLTSEDSAVYFCARKT

ISSVVDFYFDYWGQGTTVTVSSGGGGSGGGGSGGGGSDIELTQSPKFMST

SVGDRVSVTCKASQNVGTNVAWYQQKPGQSPKPLIYSATYRNSGVPDRFT

GSGSGTDFTLTITNVQSKDLADYFCQQYNRYPYTSGGGTKLEIKRAAAIE

VMYPPPYLDNEKSNGTIIHVKGKHLCPSPLFPGPSKPFWVLVVVGGVLAC

YSLLVTVAFIIFWVRSKRSRLLHSDYGGGTPRRPGPTRKHYQPYAPPRDF

AAYRSRVKFSRSADAPAYQQGQNQLYNELNLGRREEYDVLDKRRGRDPEM

GGKPRRKNPQEGLYNELQKDKMAEAYSEIGMKGERRRGKGHDGLYQGLST

ATKDTYDALHMQALPPR

An exemplary nucleotide sequence encoding the amino acid sequence of SEQ ID NO: 61 is set forth in SEQ ID NO: 62, which is provided below.

[SEQ ID NO: 62]

GAGGTGAAGCTGCAGCAGTCTGGGGCTGAGCTGGTGAGGCCTGGGTCCTC

AGTGAAGATTTCCTGCAAGGCTTCTGGCTATGCATTCAGTAGCTACTGGA

TGAACTGGGTGAAGCAGAGGCCTGGACAGGGTCTTGAGTGGATTGGACAG

ATTTATCCTGGAGATGGTGATACTAACTACAATGGAAAGTTCAAGGGTCA

-continued

```
AGCCACACTGACTGCAGACAAATCCTCCAGCACAGCCTACATGCAGCTCA

GCGGCCTAACATCTGAGGACTCTGCGGTCTATTTCTGTGCAAGAAAGACC

ATTAGTTCGGTAGTAGATTTCTACTTTGACTACTGGGGCCAAGGGACCAC

GGTCACCGTCTCCTCAGGTGGAGGTGGATCAGGTGGAGGTGGATCTGGTG

GAGGTGGATCTGACATTGAGCTCACCCAGTCTCCAAAATTCATGTCCACA

TCAGTAGGAGACAGGGTCAGCGTCACCTGCAAGGCCAGTCAGAATGTGGG

TACTAATGTAGCCTGGTATCAACAGAAACCAGGACAATCTCCTAAACCAC

TGATTTACTCGGCAACCTACCGGAACAGTGGAGTCCCTGATCGCTTCACA

GGCAGTGGATCTGGGACAGATTTCACTCTCACCATCACTAACGTGCAGTC

TAAAGACTTGGCAGACTATTTCTGTCAACAATATAACAGGTATCCGTACA

CGTCCGGAGGGGGGACCAAGCTGGAGATCAAACGGGCGGCCGCAATTGAA

GTTATGTATCCTCCTCCTTACCTAGACAATGAGAAGAGCAATGGAACCAT

TATCCATGTGAAAGGGAAACACCTTTGTCCAAGTCCCCTATTTCCCGGAC

CTTCTAAGCCCTTTTGGGTGCTGGTGGTGGTTGGTGGAGTCCTGGCTTGC

TATAGCTTGCTAGTAACAGTGGCCTTTATTATTTTCTGGGTGAGGAGTAA

GAGGAGCAGGCTCCTGCACAGTGACTACGGTGGAGGGACTCCCCGCCGCC

CCGGGCCCACCCGCAAGCATTACCAGCCCTATGCCCCACCACGCGACTTC

GCAGCCTATCGCTCCAGAGTGAAGTTCAGCAGGAGCGCAGACGCCCCCGC

GTACCAGCAGGGCCAGAACCAGCTCTATAACGAGCTCAATCTAGGACGAA

GAGAGGAGTACGATGTTTTGGACAAGAGACGTGGCCGGGACCCTGAGATG

GGGGGAAAGCCGAGAAGGAAGAACCCTCAGGAAGGCCTGTACAATGAACT

GCAGAAAGATAAGATGGCGGAGGCCTACAGTGAGATTGGGATGAAAGGCG

AGCGCCGGAGGGGCAAGGGGCACGATGGCCTTTACCAGGGTCTCAGTACA

GCCACCAAGGACACCTACGACGCCCTTCACATGCAGGCCCTGCCCCCTCG

C
```

5.3. Cells

The presently disclosed subject matter provides cells comprising a presently disclosed CAR (e.g., one disclosed in Section 5.2). In certain embodiments, the cell is selected from the group consisting of cells of lymphoid lineage and cells of myeloid lineage. In certain embodiments, the cell is an immunoresponsive cell. In certain embodiments, the immunoresponsive cell is a cell of lymphoid lineage.

In certain embodiments, the cell is a cell of the lymphoid lineage. Cells of the lymphoid lineage can provide production of antibodies, regulation of cellular immune system, detection of foreign agents in the blood, detection of cells foreign to the host, and the like. Non-limiting examples of cells of the lymphoid lineage include T cells, Natural Killer (NK) cells, B cells, dendritic cells, stem cells from which lymphoid cells may be differentiated. In certain embodiments, the stem cell is a pluripotent stem cell (e.g., embryonic stem cell).

In certain embodiments, the cell is a T cell. T cells can be lymphocytes that mature in the thymus and are chiefly responsible for cell-mediated immunity. T cells are involved in the adaptive immune system. The T cells of the presently disclosed subject matter can be any type of T cells, including, but not limited to, helper T cells, cytotoxic T cells, memory T cells (including central memory T cells, stem-cell-like memory T cells (or stem-like memory T cells), and two types of effector memory T cells: e.g., TEM cells and TEMRA cells, Regulatory T cells (also known as suppressor T cells), a tumor-reactive lymphocytes, tumor-infiltrating lymphocyte (TIL), Natural killer T cells, Mucosal associated invariant T cells, and γδ T cells. Cytotoxic T cells (CTL or killer T cells) are a subset of T lymphocytes capable of inducing the death of infected somatic or tumor cells. A patient's own T cells may be genetically modified to target specific antigens through the introduction of a CAR. In certain embodiments, the immunoresponsive cell is a T cell. The T cell can be a $CD4^+$ T cell or a $CD8^+$ T cell. In certain embodiments, the T cell is a $CD4^+$ T cell. In certain embodiments, the T cell is a $CD8^+$ T cell.

In certain embodiments, the cell is a NK cell. Natural killer (NK) cells can be lymphocytes that are part of cell-mediated immunity and act during the innate immune response. NK cells do not require prior activation in order to perform their cytotoxic effect on target cells.

Types of human lymphocytes of the presently disclosed subject matter include, without limitation, peripheral donor lymphocytes. e.g., those disclosed in Sadelain et al., *Nat Rev Cancer* (2003); 3:35-45 (disclosing peripheral donor lymphocytes genetically modified to express CARs), in Morgan, R. A., et al. 2006 *Science* 314:126-129 (disclosing peripheral donor lymphocytes genetically modified to express a full-length tumor antigen-recognizing T cell receptor complex comprising the a and B heterodimer), in Panelli et al., *J Immunol* (2000); 164:495-504; Panelli et al., *J Immunol* (2000); 164:4382-4392 (disclosing lymphocyte cultures derived from tumor infiltrating lymphocytes (TILs) in tumor biopsies), and in Dupont et al., Cancer Res (2005);65:5417-5427; Papanicolaou et al., *Blood* (2003); 102:2498-2505 (disclosing selectively in vitro-expanded antigen-specific peripheral blood leukocytes employing artificial antigen-presenting cells (AAPCs) or pulsed dendritic cells).

The cells (e.g., T cells) can be autologous, non-autologous (e.g., allogeneic), or derived in vitro from engineered progenitor or stem cells.

The cells of the presently disclosed subject matter can be cells of the myeloid lineage. Non-limiting examples of cells of the myeloid lineage include monocytes, macrophages, neutrophils, dendritic cells, basophils, neutrophils, eosinophils, megakaryocytes, mast cell, erythrocyte, thrombocytes, and stem cells from which myeloid cells may be differentiated. In certain embodiments, the stem cell is a pluripotent stem cell (e.g., an embryonic stem cell or an induced pluripotent stem cell).

In certain embodiments, the presently disclosed cells are capable of modulating the tumor microenvironment. Tumors have a microenvironment that is hostile to the host immune response involving a series of mechanisms by malignant cells to protect themselves from immune recognition and elimination. This "hostile tumor microenvironment" comprises a variety of immune suppressive factors including infiltrating regulatory $CD4^+$ T cells (Tregs), myeloid derived suppressor cells (MDSCs), tumor associated macrophages (TAMs), immune suppressive cytokines including TGF-β, and expression of ligands targeted to immune suppressive receptors expressed by activated T cells (CTLA-4 and PD-1). These mechanisms of immune suppression play a role in the maintenance of tolerance and suppressing inappropriate immune responses, however within the tumor microenvironment these mechanisms prevent an effective anti-tumor immune response. Collectively these immune suppressive factors can induce either marked anergy or apoptosis of adoptively transferred CAR modified T cells upon encounter with targeted tumor cells.

In certain embodiments, the cells can be transduced with the presently disclosed CAR such that the cells express the CAR.

In certain embodiments, the cell further comprises a soluble single-chain variable fragment (scFv) that binds a polypeptide that has immunosuppressive activity or immunostimulatory activity. In certain embodiments, immunosuppressive activity refers to induction of signal transduction or changes in protein expression in a cell (e.g., an activated immunoresponsive cell) resulting in a decrease in an immune response. Polypeptides known to suppress or decrease an immune response via their binding include CD47, PD-1, CTLA-4, and their corresponding ligands, including SIRPa, PD-L1, PD-L2, B7-1, and B7-2. Such polypeptides are present in the tumor microenvironment and inhibit immune responses to neoplastic cells. In various embodiments, inhibiting, blocking, or antagonizing the interaction of immunosuppressive polypeptides and/or their ligands enhances the immune response of the immunoresponsive cell.

In certain embodiments, the immunostimulatory activity refers to induction of signal transduction or changes in protein expression in a cell (e.g., an activated immunoresponsive cell) resulting in an increase in an immune response. Immunostimulatory activity may include pro-inflammatory activity. Polypeptides known to stimulate or increase an immune response via their binding include CD28, OX-40, 4-IBB, and their corresponding ligands, including B7-1, B7-2, OX-40L, and 4-1BBL. Such polypeptides are present in the tumor microenvironment and activate immune responses to neoplastic cells. In various embodiments, promoting, stimulating, or agonizing pro-inflammatory polypeptides and/or their ligands enhances the immune response of the immunoresponsive cell.

Cells comprising CAR and a soluble scFv that binds a polypeptide that has immunosuppressive activity or immunostimulatory activity are disclosed in International Patent Publication No. WO 2014/134165, which is incorporated by reference in its entirety.

In certain embodiments, the cell further comprises an exogenous CD40L. Cells comprising CAR and an exogenous CD40L are disclosed in International Patent Publication No. WO 2014/134165.

Furthermore, in certain embodiments, the cell is engineered to express IL-18. In certain embodiments, the cell further comprises an exogenous IL-18 polypeptide or a fragment thereof. In certain embodiments, the cell further comprises a modified promoter/enhancer at an IL-18 gene locus, which can increase IL-18 gene expression, e.g., a constitutive or inducible promoter is placed to drive IL-18 gene expression. Cells comprising a CAR and engineered to express IL-18, e.g., comprising an exogenous IL-18 polypeptide or a fragment thereof or a modified promoter/enhancer at an IL-18 gene locus are disclosed in International Patent Publication No. WO2018/027155, which is incorporated by reference in its entirety.

Additionally or alternatively, the cell is engineered to express IL-33. In certain embodiments, the cell further comprises an exogenous IL-33 polypeptide or a fragment thereof. In certain embodiments, the cell further comprises a modified promoter/enhancer at an IL-33 gene locus, which can increase IL-33 gene expression, e.g., a constitutive or inducible promoter placed to drive IL-33 gene expression. Cells comprising a CAR and engineered to express IL-33, e.g., comprising an exogenous IL-33 polypeptide or a fragment thereof or a modified promoter/enhancer at an IL-33 gene locus are disclosed in International Patent Publication No. WO2019/099479, which is incorporated by reference in its entirety.

Additionally or alternatively, the cell is engineered to express IL-36. In certain embodiments, the cell further comprises an exogenous IL-36 polypeptide or a fragment thereof. In certain embodiments, the cell further comprises a modified promoter/enhancer at an IL-36 gene locus, which can increase IL-36 gene expression, e.g., a constitutive or inducible promoter placed to drive IL-36 gene expression. Cells comprising a CAR and engineered to express IL-36, e.g., comprising an exogenous IL-36 polypeptide or a fragment thereof or a modified promoter/enhancer at an IL-36 gene locus are disclosed in International Patent Publication No. WO2019/099483, which is incorporated by reference in its entirety.

5.4. Compositions and Vectors

The presently disclosed subject matter provides compositions comprising a presently disclosed CAR (e.g., one disclosed in Section 5.2). Also provided are cells comprising such compositions.

In certain embodiments, the presently disclosed CAR is encoded by a nucleic acid molecule which is operably linked to a promoter.

Furthermore, the presently discloses subject matter provides nucleic acid compositions comprising a polynucleotide encoding a presently disclosed CAR (e.g., one disclosed in Section 5.2). Also provided are cells comprising such nucleic acid compositions.

In certain embodiments, the nucleic acid composition further comprises a promoter that is operably linked to the polynucleotide encoding the presently disclosed CAR.

In certain embodiments, the promoter is endogenous or exogenous. In certain embodiments, the exogenous promoter is selected from an elongation factor (EF)-1 promoter, a cytomegalovirus immediate-early promoter (CMV) promoter, a simian virus 40 early promoter (SV40) promoter, a phosphoglycerate kinase (PGK) promoter, and a metallothionein promoter. In certain embodiments, the promoter is an inducible promoter. In certain embodiment, the inducible promoter is selected from a NFAT transcriptional response element (TRE) promoter, a CD69 promoter, a CD25 promoter, and an IL-2 promoter.

The compositions and nucleic acid compositions can be administered to subjects or and/delivered into cells by art-known methods or as described herein. Genetic modification of a cell (e.g., a T cell or a NK cell) can be accomplished by transducing a substantially homogeneous cell composition with a recombinant DNA construct. In certain embodiments, a retroviral vector (e.g., gamma-retroviral vector or lentiviral vector) is employed for the introduction of the DNA construct into the cell. For example, a polynucleotide encoding an antigen-recognizing receptor can be cloned into a retroviral vector and expression can be driven from its endogenous promoter, from the retroviral long terminal repeat, or from a promoter specific for a target cell type of interest. Non-viral vectors may be used as well.

For initial genetic modification of a cell to include a presently disclosed CAR, a retroviral vector can be employed for transduction, however any other suitable viral vector or non-viral delivery system can be used. The antigen-recognizing receptor can be constructed in a single, multicistronic expression cassette, in multiple expression cassettes of a single vector, or in multiple vectors. Examples of elements that create polycistronic expression cassette include, but is not limited to, various viral and non-viral Internal Ribosome Entry Sites (IRES, e.g., FGF-1 IRES, FGF-2 IRES, VEGF IRES, IGF-II IRES, NF-κB IRES, RUNX1 IRES, p53 IRES, hepatitis A IRES, hepatitis C IRES, pestivirus IRES, aphthovirus IRES, picornavirus IRES, poliovirus IRES and encephalomyocarditis virus IRES) and cleavable linkers (e.g., 2A peptides, e.g., P2A, T2A, E2A and F2A peptides). Combinations of retroviral vector and an appropriate packaging line are also suitable, where the capsid proteins will be functional for infecting human cells. Various amphotropic virus-producing cell lines are known, including, but not limited to, PA12 (Miller et al., (1985) *Mol Cell Biol* (1985);5:431-437); PA317 (Miller., et al., *Mol Cell Biol* (1986); 6:2895-2902); and CRIP (Danos et al., *Proc Natl Acad Sci USA* (1988);85:6460-6464). Non-amphotropic particles are suitable too, e.g., particles pseudotyped with VSVG, RD114 or GALV envelope and any other known in the art.

Possible methods of transduction also include direct co-culture of the cells with producer cells (Bregni et al., *Blood* (1992);80:1418-1422), or culturing with viral supernatant alone or concentrated vector stocks with or without appropriate growth factors and polycations (Xu et al., *Exp Hemat* (1994); 22:223-230; and Hughes et al. *J Clin Invest* (1992); 89:1817).

Other transducing viral vectors can be used to modify a cell. In certain embodiments, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). Other viral vectors that can be used include, for example, adenoviral, lentiviral, and adena-associated viral vectors, vaccinia virus, a bovine papilloma virus, or a herpes virus, such as Epstein-Barr Virus (also see, for example, the vectors of Miller, *Human Gene Thera* (1990); 15-14; Friedman, Science 244:1275-1281, 1989; Eglitis et al., *BioTechniques* (1988);6:608-614; Tolstoshev et al., *Cur Opin Biotechnol* (1990); 1:55-61; Sharp, *The Lancet* (1991);337:1277-78; Cornetta et al., Nucleic Acid Research and Molecular Biology 36:311-22, 1987; Anderson, *Science* (1984);226:401-409; Moen, Blood Cells 17:407-16, 1991; Miller et al., *Biotechnol* (1989);7:980-90; LeGal La Salle et al., *Science* (1993);259:988-90; and Johnson, *Chest* (1995) 107: 77S-83S). Retroviral vectors are particularly well developed and have been used in clinical settings (Rosenberg et al., *N Engl J Med* (1990); 323:370, 1990; Anderson et al., U.S. Pat. No. 5,399,346).

Non-viral approaches can also be employed for genetic modification of a cell. For example, a nucleic acid molecule can be introduced into a cell by administering the nucleic acid in the presence of lipofection (Feigner et al., *Proc Natl Acad Sci U.S.A.* (1987);84:7413; Ono et al., *Neurosci Lett* (1990); 17:259; Brigham et al., *Am J Med Sci* (1989);298:278; Staubinger et al., Methods in Enzymol (1983); 101:512, Wu et al., *J Biol Chem* (1988);263:14621; Wu et al., *J Biol Chem* (1989);264:16985), or by micro-injection under surgical conditions (Wolff et al., *Science* (1990);247:1465). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases, CRISPR). Transient expression may be obtained by RNA electroporation.

Any targeted genome editing methods can also be used to deliver a presently disclosed antigen-recognizing receptor to a cell or a subject. In certain embodiments, a CRISPR system is used to deliver a presently disclosed antigen-recognizing receptor disclosed herein. In certain embodiments, zinc-finger nucleases are used to deliver the antigen-recognizing receptor. In certain embodiments, a TALEN system is used to deliver a presently disclosed antigen-recognizing receptor.

Clustered regularly-interspaced short palindromic repeats (CRISPR) system is a genome editing tool discovered in prokaryotic cells. When utilized for genome editing, the system includes Cas9 (a protein able to modify DNA utilizing crRNA as its guide), CRISPR RNA (crRNA, contains the RNA used by Cas9 to guide it to the correct section of host DNA along with a region that binds to tracrRNA (generally in a hairpin loop form) forming an active complex with Cas9), trans-activating crRNA (tracrRNA, binds to crRNA and forms an active complex with Cas9), and an optional section of DNA repair template (DNA that guides the cellular repair process allowing insertion of a specific DNA sequence). CRISPR/Cas9 often employs a plasmid to transfect the target cells. The crRNA needs to be designed for each application as this is the sequence that Cas9 uses to identify and directly bind to the target DNA in a cell. The repair template carrying CAR expression cassette need also be designed for each application, as it must overlap with the sequences on either side of the cut and code for the insertion sequence. Multiple crRNA's and the tracrRNA can be packaged together to form a single-guide RNA (sgRNA). This sgRNA can be joined together with the Cas9 gene and made into a plasmid in order to be transfected into cells.

A zinc-finger nuclease (ZFN) is an artificial restriction enzyme, which is generated by combining a zinc finger DNA-binding domain with a DNA-cleavage domain. A zinc finger domain can be engineered to target specific DNA sequences which allows a zinc-finger nuclease to target desired sequences within genomes. The DNA-binding domains of individual ZFNs typically contain a plurality of individual zinc finger repeats and can each recognize a plurality of basepairs. The most common method to generate new zinc-finger domain is to combine smaller zinc-finger "modules" of known specificity. The most common cleavage domain in ZFNs is the non-specific cleavage domain from the type IIs restriction endonuclease FokI. Using the endogenous homologous recombination (HR) machinery and a homologous DNA template carrying CAR expression cassette, ZFNs can be used to insert the CAR expression cassette into genome. When the targeted sequence is cleaved by ZFNs, the HR machinery searches for homology between the damaged chromosome and the homologous DNA template, and then copies the sequence of the template between the two broken ends of the chromosome, whereby the homologous DNA template is integrated into the genome.

Transcription activator-like effector nucleases (TALEN) are restriction enzymes that can be engineered to cut specific sequences of DNA. TALEN system operates on almost the same principle as ZFNs. They are generated by combining a transcription activator-like effectors DNA-binding domain with a DNA cleavage domain. Transcription activator-like effectors (TALEs) are composed of 33-34 amino acid repeating motifs with two variable positions that have a strong recognition for specific nucleotides. By assembling arrays of these TALEs, the TALE DNA-binding domain can be engineered to bind desired DNA sequence, and thereby guide the nuclease to cut at specific locations in genome.cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Methods for delivering the genome editing agents/systems can vary depending on the need. In certain embodiments, the components of a selected genome editing method are delivered as DNA constructs in one or more plasmids. In certain embodiments, the components are delivered via viral vectors. Common delivery methods include but is not limited to, electroporation, microinjection, gene gun, impalefection, hydrostatic pressure, continuous infusion, sonication, magnetofection, adeno-associated viruses, envelope protein pseudotyping of viral vectors, replication-competent vectors cis and trans-acting elements, herpes simplex virus, and chemical vehicles (e.g., oligonucleotides, lipoplexes, polymersomes, polyplexes, dendrimers, inorganic Nanoparticles, and cell-penetrating peptides).

5.5. Polypeptides

The presently disclosed subject matter provides methods for optimizing an amino acid sequence or a nucleic acid sequence by producing an alteration in the sequence. Such alterations may include certain mutations, deletions, insertions, or post-translational modifications. The presently disclosed subject matter further includes analogs of any naturally-occurring polypeptides disclosed herein (including, but not limited to, CD19, CD8, CD28, 4-1BB, and CD3ζ). Analogs can differ from a naturally-occurring polypeptide disclosed herein by amino acid sequence differences, by post-translational modifications, or by both. Analogs can exhibit at least about 85%, about 90%, about 91%, about 92%, about 93%, about 94%, about 95%, about 96%, about 97%, about 98%, about 99% or more homologous to all or part of a naturally-occurring amino, acid sequence of the presently disclosed subject matter. The length of sequence comparison is at least 5, 10, 15 or 20 amino acid residues, e.g., at least 25, 50, or 75 amino acid residues, or more than 100 amino acid residues. Again, in an exemplary approach to determining the degree of identity, a BLAST program may be used, with a probability score between e-3 and e-100 indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the presently disclosed subject matter also provides fragments of any of the polypeptides disclosed herein. As used herein, the term "a fragment" means at least 5, 10, 13, or 15 amino acids. In certain embodiments, a fragment comprises at least 20 contiguous amino acids, at least 30 contiguous amino acids, or at least 50 contiguous amino acids. In certain embodiments, a fragment comprises at least 60 to 80, 100, 200, 300 or more contiguous amino acids. Fragments can be generated by methods known to those skilled in the art or may result from normal protein processing (e.g., removal of amino acids from the nascent polypeptide that are not required for biological activity or removal of amino acids by alternative mRNA splicing or alternative protein processing events).

5.6. Formulations and Administration

The presently disclosed subject matter also provides compositions comprising the presently disclosed cells. Compositions comprising the presently disclosed cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the genetically modified cells in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the presently disclosed subject matter, however, any vehicle, diluent, or additive used would have to be compatible with the genetically modified cells.

The compositions can be isotonic, i.e., they can have the same osmotic pressure as blood and lacrimal fluid. The desired isotonicity of the compositions may be accomplished using sodium chloride, or other pharmaceutically acceptable agents such as dextrose, boric acid, sodium tartrate, propylene glycol or other inorganic or organic solutes. Sodium chloride can be particularly for buffers containing sodium ions.

Viscosity of the compositions, if desired, can be maintained at the selected level using a pharmaceutically acceptable thickening agent. For example, methylcellulose is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Compositions comprising the presently disclosed cells can be provided systemically or directly to a subject for inducing and/or enhancing an immune response to an antigen and/or treating and/or preventing a neoplasia. In certain embodiments, the presently disclosed cells or compositions comprising thereof are directly injected into an organ of interest (e.g., an organ affected by a neoplasia). Alternatively, the presently disclosed cells or compositions comprising thereof are provided indirectly to the organ of interest, for example, by administration into the circulatory system (e.g., the tumor vasculature). Expansion and differentiation agents can be provided prior to, during or after administration of the cells or compositions to increase production of cells (e.g., T cells or NK cells) in vitro or in vivo.

The presently disclosed cells can be administered in any physiologically acceptable vehicle, normally intravascularly, although they may also be introduced into bone or other convenient site where the cells may find an appropriate site for regeneration and differentiation (e.g., thymus).

The quantity of cells to be administered can vary for the subject being treated. In certain embodiments, between about $10^4$ and about $10^{10}$, between about $10^4$ and about $10^7$, between about $10^5$ and about $10^7$, between about $10^5$ and about $10^9$, between about $10^5$ and about $10^{10}$, or between about $10^6$ and about $10^8$ of the presently disclosed cells are administered to a subject. More effective cells may be administered in even smaller numbers. Usually, at least about $1\times10^5$ cells will be administered, eventually reaching about $1\times10^{10}$ or more. In certain embodiments, at least about $1\times10^5$, about $2\times10^5$, about $5\times10^5$, about $1\times10^6$, about $5\times10^6$, about $1\times10^7$, about $5\times10^7$, about $1\times10^8$, about $5\times10^8$, about $1\times10^9$, or about $5\times10^9$ of the presently disclosed cells are administered to a subject. In certain embodiments, between about $10^5$ and about $10^6$ of the presently disclosed cells are administered to a subject. In certain embodiments, about $1\times10^5$ of the presently disclosed cells are administered to a subject. In certain embodiments, about $2\times10^5$ of the presently disclosed cells are administered to a subject. In certain embodiments, about $5\times10^5$ of the presently disclosed cells are administered to a subject. In certain embodiments, about $1\times10^6$ of the presently disclosed cells are administered to a subject. The precise determination of what would be considered an effective dose can be based on factors individual to each subject, including their size, age, sex, weight, and condition of the particular subject. Dosages can be readily ascertained by those skilled in the art from this disclosure and the knowledge in the art.

The presently disclosed cells can comprise a purified population of cells. Those skilled in the art can readily determine the percentage of the presently disclosed cells in a population using various well-known methods, such as fluorescence activated cell sorting (FACS). Suitable ranges of purity in populations comprising the presently disclosed immunoresponsive cells are about 50% to about 55%, about 5% to about 60%, and about 65% to about 70%. In certain embodiments, the purity is about 70% to about 75%, about 75% to about 80%, or about 80% to about 85%. In certain embodiments, the purity is about 85% to about 90%, about 90% to about 95%, and about 95% to about 100%. Dosages can be readily adjusted by those skilled in the art (e.g., a decrease in purity may require an increase in dosage). The cells can be introduced by injection, catheter, or the like.

The skilled artisan can readily determine the amount of cells and optional additives, vehicles, and/or carrier in compositions and to be administered in methods. Typically, any additives (in addition to the active cell(s) and/or agent(s)) are present in an amount of 0.001 to 50% (weight) solution in phosphate buffered saline, and the active ingredient is present in the order of micrograms to milligrams, such as about 0.0001 to about 5 wt %, about 0.0001 to about 1 wt %, about 0.0001 to about 0.05 wt % or about 0.001 to about 20 wt %, about 0.01 to about 10 wt %, or about 0.05 to about 5 wt %. For any composition to be administered to an animal or human, the followings can be determined: toxicity such as by determining the lethal dose (LD) and LD50 in a suitable animal model e.g., rodent such as mouse; the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

In certain embodiments, the composition is a pharmaceutical composition comprising the presently disclosed cells and a pharmaceutically acceptable carrier.

Administration of the compositions can be autologous or heterologous. For example, cells can be obtained from one subject, and administered to the same subject or a different, compatible subject. Peripheral blood derived cells or their progeny (e.g., in vivo, ex vivo or in vitro derived) can be administered. When administering a presently disclosed composition (e.g., a pharmaceutical composition comprising presently disclosed cells), it can be formulated in a unit dosage injectable form (solution, suspension, emulsion).

The presently disclosed cells and compositions can be administered by any method known in the art including, but not limited to, oral administration, intravenous administration, subcutaneous administration, intranodal administration, intratumoral administration, intrathecal administration, intrapleural administration, intraosseous administration, intraperitoneal administration, pleural administration, and direct administration to the subject.

5.7. Methods of Treatment

The presently disclosed subject matter provides methods for inducing and/or increasing an immune response in a subject in need thereof. The presently disclosed cells and compositions comprising thereof can be used in a therapy or medicament. The presently disclosed subject matter provides various methods of using the cells (e.g., T cells, e.g., $CD4^+$ T cells or $CD8^+$ T cells) or compositions comprising thereof. For example, the presently disclosed cells and compositions comprising thereof can be used for reducing tumor burden in a subject. The presently disclosed cell can reduce the number of tumor cells, reduce tumor size, and/or eradicate the tumor in the subject. The presently disclosed cells and compositions comprising thereof can be used for treating and/or preventing a neoplasm or a tumor in a subject. The presently disclosed cells and compositions comprising thereof can be used for prolonging the survival of a subject suffering from a neoplasm or a tumor. The presently disclosed cells and compositions comprising thereof can be used for treating and/or preventing a pathogen infection in a subject. Such methods comprise administering the presently disclosed cells or a composition (e.g., a pharmaceutical composition) comprising thereof to achieve the desired effect, e.g., palliation of an existing condition or prevention of recurrence. For treatment, the amount administered is an amount effective in producing the desired effect. An effective amount can be provided in one or a series of administrations. An effective amount can be provided in a bolus or by continuous perfusion.

The presently disclosed subject matter provides various methods of using the cells (e.g., T cells) or compositions comprising thereof. For example, the presently disclosed subject matter provides methods of reducing tumor burden in a subject. In certain embodiments, the method of reducing tumor burden comprises administering the presently disclosed cells or a composition comprising thereof to the subject. The presently disclosed cell can reduce the number of tumor cells, reduce tumor size, and/or eradicate the tumor in the subject.

The tumor can be a solid tumor. Non-limiting examples of solid tumor include mesothelioma, lung cancer, pancreatic cancer, ovarian cancer, breast cancer, colorectal cancer, pleural tumor, glioblastoma, esophageal cancer, gastric cancer, synovial sarcoma, thymic carcinoma, endometrial carcinoma, stomach cancer, melanoma, hepatocarcinoma, renal cell carcinoma, soft tissue sarcoma, and cholangiocarcinoma.

The presently disclosed subject matter also provides methods of increasing or lengthening survival of a subject having a neoplasm. In certain embodiments, the method of increasing or lengthening survival of a subject having neoplasm comprises administering the presently disclosed immunoresponsive cells or a composition comprising thereof to the subject. The method can reduce or eradicate tumor burden in the subject. Additionally, the presently disclosed subject matter provides methods for increasing an immune response in a subject, comprising administering the presently disclosed cell or a composition comprising thereof to the subject. The presently disclosed subject matter further provides methods for treating and/or preventing a neoplasm in a subject, comprising administering the presently disclosed cells or a composition comprising thereof to the subject.

Non-limiting examples of neoplasms or tumors include B cell leukemia, B cell lymphoma, acute lymphoblastic leukemia (ALL), chronic lymphocytic leukemia (CLL), acute myeloid leukemia (AML), multiple myeloma, lymphoma (Hodgkin's lymphoma, non-Hodgkin's lymphoma), glioblastoma, myelodysplastic syndrome (MDS), and chronic myelogenous leukemia (CML), bone cancer, intestinal cancer, liver cancer, skin cancer, cancer of the head or neck, melanoma (cutaneous or intraocular malignant melanoma), renal cancer (e.g. clear cell carcinoma), throat cancer, prostate cancer (e.g. hormone refractory prostate adenocarcinoma), blood cancers (e.g. leukemias, lymphomas, and myelomas), uterine cancer, rectal cancer, cancer of the anal region, bladder cancer, brain cancer, stomach cancer, testicular cancer, carcinoma of the fallopian tubes, carcinoma of the endometrium, carcinoma of the cervix, carcinoma of the vagina, carcinoma of the vulva, leukemias (e.g., acute leukemia, acute lymphocytic leukemia, acute myelocytic leukemia, acute myeloblastic leukemia, acute promyelocytic leukemia, acute monocytic leukemia, acute erythroleukemia, chronic leukemia, chronic myelocytic leukemia, polycythemia vera, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, include Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, hepatoma, nile duct carcinoma, choriocarcinoma, seminoma, embryonal carcinoma, Wilm's tumor, cervical cancer, salivary gland cancer, uterine cancer, testicular cancer, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

In certain embodiments, the tumor or neoplasm is selected from the group consisting of B cell leukemia, B cell lymphoma, acute lymphoblastic leukemia (ALL), Chronic Lymphocytic Leukemia (CLL), non-Hodgkin's lymphoma, Burkitt lymphoma, acute myeloid leukemia (AML), and Mixed-phenotype acute leukemia (MPAL). In certain embodiments, the CAR binds to CD19.

The presently disclosed subject matter also provides methods of increasing or lengthening survival of a subject having a pathogen infection. In certain embodiments, the method comprises administering the presently disclosed immunoresponsive cells or a composition comprising thereof to the subject. Non-limiting pathogen infections include HIV and fungal infections.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Further modification can be introduced to the presently disclosed cells (e.g., T cells) to avert or minimize the risks of immunological complications (known as "malignant T-cell transformation"), e.g., graft versus-host disease (GvHD), or when healthy tissues express the same target antigens as the tumor cells, leading to outcomes similar to GvHD. A potential solution to this problem is engineering a suicide gene into the presently disclosed cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T cell elimination by administering anti-EGFR monoclonal antibody (e.g., cetuximab). EGFRt can be covalently joined to the upstream of the CAR. The suicide gene can be included within the vector comprising nucleic acids encoding a presently disclosed CAR. In this way, administration of a prodrug designed to activate the suicide gene (e.g., a prodrug (e.g., AP1903 that can activate iCasp-9) during malignant T-cell transformation (e.g., GVHD) triggers apoptosis in the suicide gene-activated cells expressing the CAR. The incorporation of a suicide gene into the a presently disclosed e.g., CAR gives an added level of safety with the ability to eliminate the majority of receptor-expressing cells within a very short time period. A presently disclosed cell (e.g., a T cell) incorporated with a suicide gene can be pre-emptively eliminated at a given timepoint post the cell infusion, or eradicated at the earliest signs of toxicity.

5.8. Kits

The presently disclosed subject matter provides kits for inducing and/or enhancing an immune response in a subject, treating and/or preventing a neoplasm or tumor in a subject, reducing tumor burden in a subject, increasing or lengthening survival of a subject having a neoplasm in a subject, and/or treating and/or preventing a pathogen infection. In certain embodiments, the kit comprises the presently disclosed cells or a composition comprising thereof. In certain embodiments, the kit comprises a sterile container; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In certain non-limiting embodiments, the kit includes a nucleic acid molecule encoding a presently disclosed CAR.

If desired, the cells and/or nucleic acid molecules are provided together with instructions for administering the cells or nucleic acid molecules to a subject having or at risk of developing a neoplasia. The instructions generally include information about the use of the composition for the treatment and/or prevention of neoplasia. In certain embodiments, the instructions include at least one of the following: description of the therapeutic agent; dosage schedule and administration for treatment or prevention of a neoplasia; precautions; warnings; indications; counter-indications; over-dosage information; adverse reactions; animal pharmacology; clinical studies; and/or references. The instructions may be printed directly on the container (when present), or as a label applied to the container, or as a separate sheet, pamphlet, card, or folder supplied in or with the container.

6. EXAMPLE

The presently disclosed subject matter will be better understood by reference to the following Example, which is provided as exemplary of the presently disclosed subject matter, and not by way of limitation.

Example 1: In Vitro and In Vivo Characterization of CD28 Mutant CAR T Cells

It appears that PI3K signaling is redundant as not only does CD28 bind to the PI3K p85 subunit directly (via the presence of the YMxM consensus in YMNM (SEQ ID NOs: 20 and 19, left to right, respectively)), but Grb2 (which binds to the YxNx consensus motif (SEQ ID NO: 21) binds to Gab1 and Gab2, which in turn can recruit the PI3K p85 subunit, initiating downstream signaling.

Figure 1:
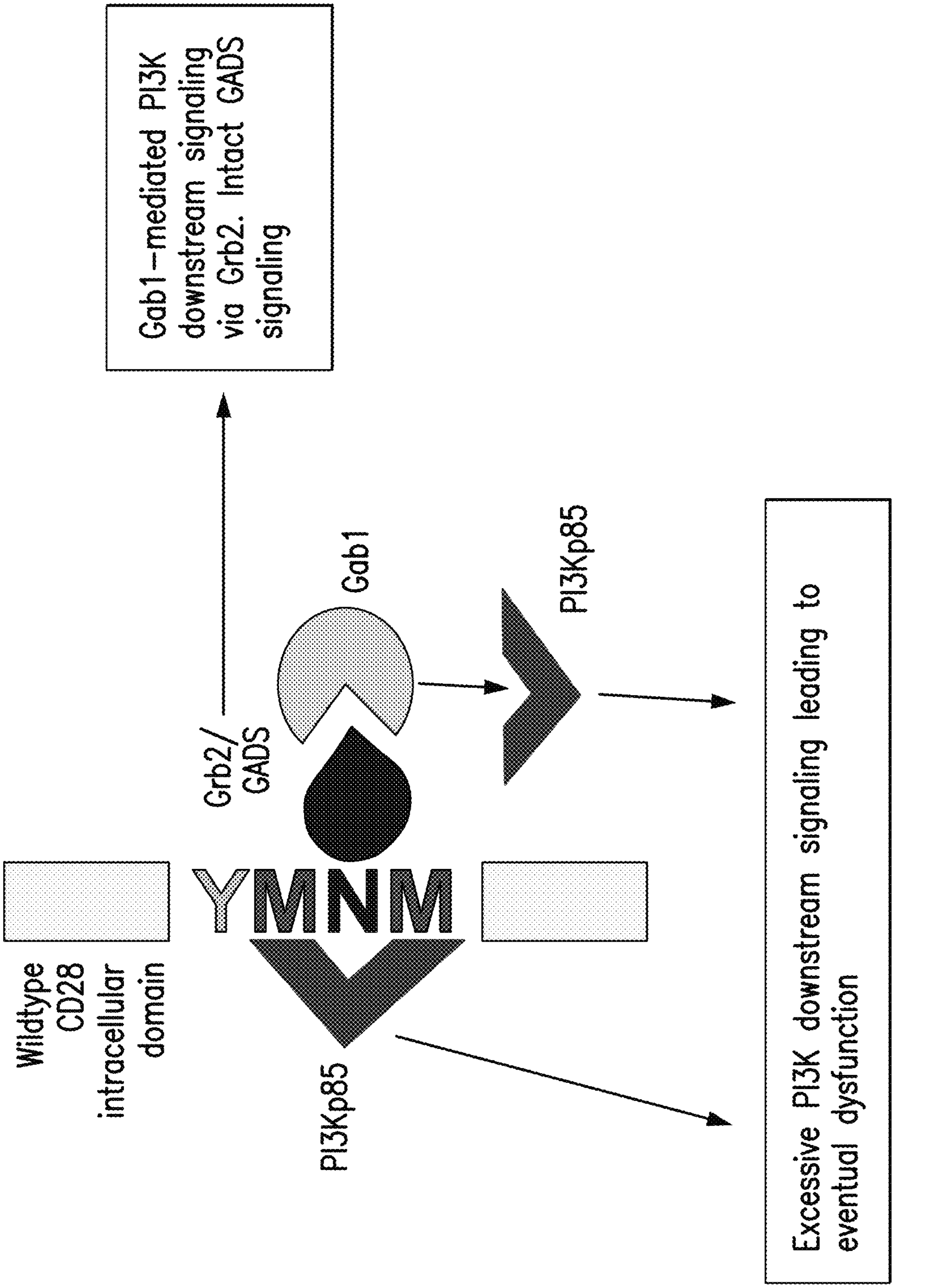
FIG. 1 is a schematic showing of physiological CD28 signaling (SEQ ID NO: 19).

Given the diverse number of adaptor molecules that can coalesce on the CD28 molecule, T cell functional outcomes (i.e. effector cytotoxicity, cytokine secretion, activation, survival, memory formation and exhaustion) are most likely as a result of the sum of downstream signaling cascades originating from the binding of these adaptor molecules to CD28. Hence, modification of these CD28 motifs may permit or restrict binding of various adaptor molecules that would alter signaling, resulting in potentiation of effector function and/or mitigation of dysfunction. Given the implication of PI3K signaling in terminal differentiation of T cells, the redundancy of this signaling pathway might be detrimental for effector function, and modulating it might be beneficial (FIG. 1).

Figure 2:
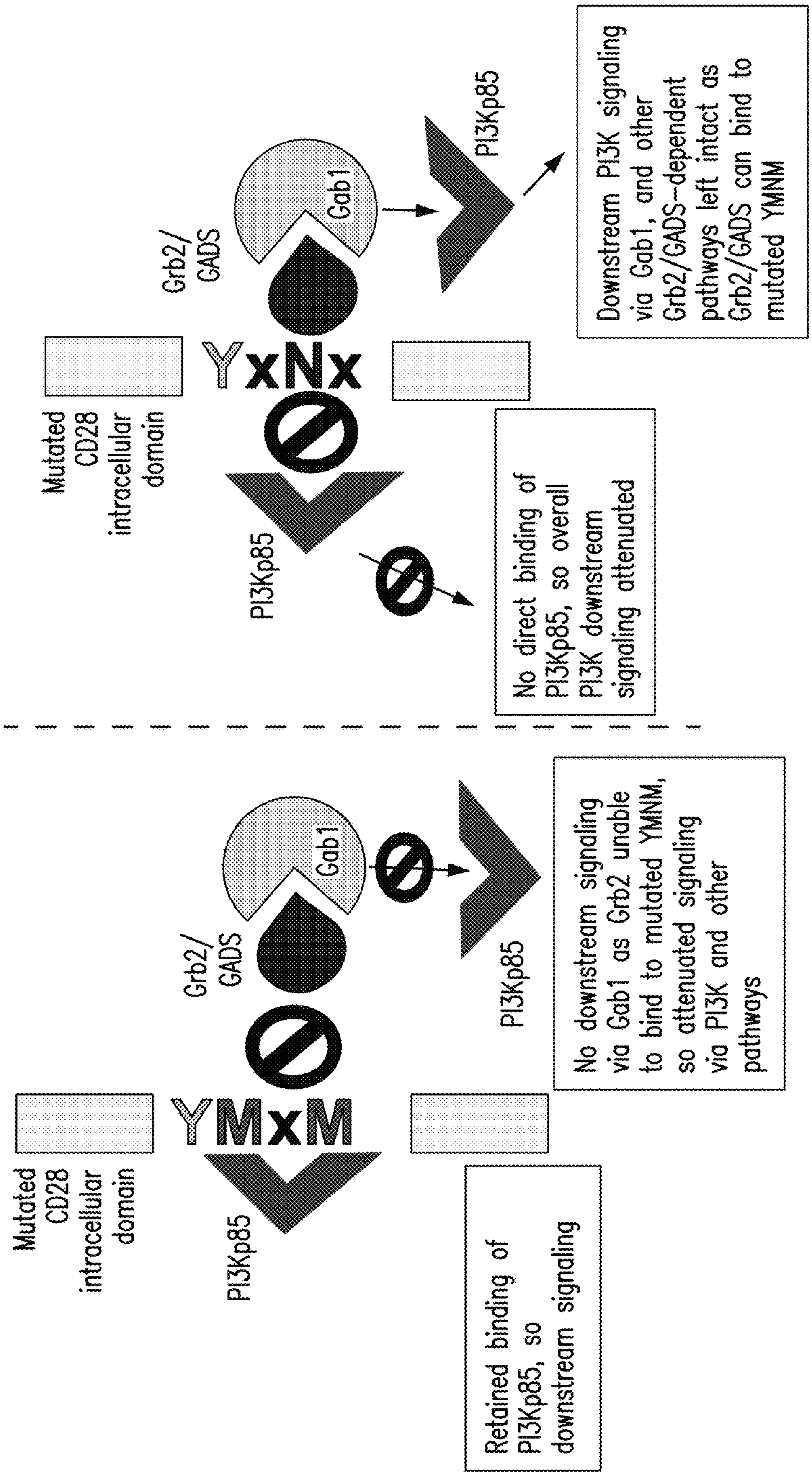
FIG. 2 is a schematic showing of CD28 modifications to modulate PI3Kp85 binding to CD28 (SEQ ID NOs: 20 and 21, left to right, respectively).

Given the capacity for the YMNM motif in CD28 to determine binding partners (adaptor molecules), and for those partners to determine T cell fate via a number of signaling cascades originating from PI3K, Grb2, and GADS, a number of CD28 mutations were created that either permitted, or excluded, the binding of these adaptor molecules to CD28 (FIG. 2, FIG. 12).

Characterization of CD28-YKNI Mutant CAR T Cells

CD28-YKNI mutant CAR T cells were created. Different human CD19-targeted CAR T cells expressing a truncated EGFR domain (Etah 19) were cocultured with CD19+ NALM6 cells expressing GFP-ffLuciferase (NALM6gL) at different effector: tumor ratios. Tumor cell lysis (relative to a non-signaling CAR T cell) was measured by bioluminescence 24 hours later. It was found that CD28-YKNI mutant CAR T cells had potent killing capacity in vitro (FIGS. 3A-3D).

Human CD19-targeted CAR T cells were cultured ALONE cocultured with CD19+ NALM6 cells at an effector: tumor ratio of 1:1. 24 hours later, supernatant was collected and cytokines were measured utilizing a bead-based multiplex assay. CD28-YKNI mutant CAR T cells had a unique cytokine secretion profile (FIGS. 4A-4N).

Different human CD19-targeted CAR T cells were cocultured with NALM6 at an E:T ratio of 1:5 and at a concentration of 50,000 CAR T cells/mL. Roughly every 5 days, CAR T cells were counted and characterized by flow cytometry, memory phenotype (CD62L+), and CD4/CD8 distribution. The starting number of tumor cells were added back into the culture at different timepoints. CD28-YKNI mutant CAR T cells also had potent killing proliferative capacity in vitro (FIG. 5). CD28-YKNI mutant CAR T cells retained a memory phenotype in the context of repeated antigen encounter in comparison to CD28 and CD28-1xx CAR T cells (FIG. 6). CD28-YKNI mutant CAR T cells retained a relatively balanced CD8: CD4 ratio in the context of repeated antigen encounter in comparison to CD28 and CD28-1xx CAR T cells (FIG. 7).

CD28-YKNI mutant CAR T cells demonstrated a constrained activation profile after single and multiple stimulations. CAR T cells were cocultured with NALM6gL at an initial E: T of 1:5 (1 stimulation). In parallel, CAR T cells were repeatedly stimulated with the same amount of tumor for a total of 5 stimulations (with 1 stimulation every 12 hours). Approximately ten days post initiation of coculture, size/blastogenesis (as assessed by forward scatter) was assessed by flow cytometry. CD28-YKNI mutant CAR T cells demonstrated lower blastogenesis post single or multiple activations (FIG. 8).

Metabolic profile of the CD28-YKNI mutant CAR T cells was measured nine days after single or multiple stimulations. CD28-YKNI mutant CAR T cells demonstrated significantly lower basal respiration after single or multiple stimulations (FIG. 9A). Significantly higher basal oxygen consumption rate (OCR) were measured in Etah19h28Z and Etah19h28Zp33 after 5× stimulation with leukemia antigens, while after only 1× stimulation this difference was not present. The increased basal oxygen consumption of cells suggested a preferential reliance on oxidative phosphorylation as the predominant energy generating mechanism to account for the metabolic demands required for enhanced CAR T cell proliferation. This was further confirmed with an increase in basal OCR following additional stimulation with tumor antigens (e.g., stim 5× compared to stim 1×).

CD28-YKNI mutant CAR T cells also demonstrated significantly lower lactic acid production after single or multiple stimulations (FIG. 9B). Extracellular acidification rate (ECAR) is a measurable surrogate for lactic acid production during glycolysis. Increase in the basal ECAR in stimulated CAR T cells suggests increased glycolytic activity, which is typically measured in T cells activated with antigens. Increase in ECAR in Etah19hMUThZ was observed, but minimal, suggesting that T cells with this modification did not experience significant stimulation.

CAR T cells were cocultured with NALM6gL at an initial E: T of 1:5 (1 stimulation). In parallel, CAR T cells were repeatedly stimulated with the same amount of tumor for a total of 5 stimulations (with 1 stimulation every 12 hours). Approximately ten days post initiation of coculture, exhaustion markers (LAG3 and PD1) were assessed by flow cytometry. CD28-YKNI mutant CAR T cells express lower levels of co-inhibitory molecules (LAG3 and PD1, TIM-3 and PD1) and in the setting of single or multiple stimulations (FIGS. 10A-10B)

The in vivo anti-tumor effect of mutant-based CAR T cells was measured. NCG mice were inoculated with $10^6$ NALM6gfp$^+$ffLUC$^+$ tumor cells, and treated with CAR T cells 4 days later. CAR T cells were derived from two different healthy donors. CD28-YKNI mutant CD19-targeted CAR T cells outperformed standard CD28-based CAR T cells in vivo (FIG. 11).

Characterization of Other CD28 Mutant CAR T Cells

Different Human CD19-targeted CD28 mutant CAR T cells (CD28-YKNI, CD28-YMDM, CD28-YGGG, CD28-YENV, CD28-YKNL, and CD28-YSNV) CD28-expressing a truncated EGFR domain (Etah19) were cocultured with CD19+ NALM6 cells expressing GFP-ffLuciferase (NALM6gL) at different effector: tumor ratios, and tumor cell lysis (relative to a non-signaling CAR T cell) was measured by bioluminescence 24 hours later. CD28-YKNI mutant CAR T cells showed comparable killing capacity in 24-hour killing assays (FIG. 13).

Different human CD19-targeted CAR T cells were cocultured with NALM6 at an E:T ratio of 1:5 at an initial concentration of 25,000 CAR T cells/mL. Concentrations of CAR$^+$ and NALM6 were measured daily and plotted over the course of 6 days. CD28-Yxxx Mutant CD19-targeted CAR T cells (YKNI, YENV, and YMDM (SEQ ID NOs: 26, 22 and 32, left to right, respectively)) outperform standard CD28-based CAR T cells in vitro (FIG. 14). CD28 mutants displayed potent long-term cytotoxic capacity in vitro.

CAR T cells were cocultured with NALM6gL at an initial E: T of 1:5 (1 stimulation). In parallel, CAR T cells were repeatedly stimulated with the same amount of tumor for a total of 5 stimulations (with 1 stimulation every 12 hours). Approximately ten days post initiation of coculture, exhaustion markers (TIM3 and PD1) were assessed by flow cytometry. CD28 mutants demonstrated a favorable exhaustion immunophenotype (FIG. 15).

CD28-Yxxx mutant CD19-targeted CAR T cells (YKNI, YENV, and YMDM (SEQ ID NOS: 26, 22 and 32, left to right, respectively)) outperformed standard CD28-based CAR T cells in vivo (FIGS. 16-18). NCG mice were inoculated with 1e6 NALM6gfp$^+$ffLUC$^+$ tumor cells, and treated with CAR T cells 4 days later. Survival rates were charted. Bioluminescence was measured weekly. CAR T cells were derived from a single healthy donor.

Example 2: Characterization of CD28 Mutant CAR T Cells

CD28-Yxxx mutant CD19-targeted CAR T cells, including YENV, YKNI, YGGG, YMDM and YSNV CD19-targeted CAR T cells were created (SEQ ID NOs: 22, 26, 44, 32, and 23 left to right, respectively). The in vitro and in vivo features of these CD28 mutant CAR T cells were characterized.

CD28-Yxxx mutant CD19-targeted CAR T cells were cocultured with NALM6gL at an E: T ratio of 1:15. Concentrations of and NALM6 were measured daily and plotted over the course of 7 days and plotted as cells/mL. It was observed that CD28-Yxxx mutant CD19-targeted CAR T cells (CD28-YENV, CD28-YKNI, CD28-YGGG, CD28-YMDM and CD28-YSNV) outperformed standard CD28-based CAR T cells, and demonstrated potent long-term cytotoxicity capacity in vitro (FIG. 19).

CD28-Yxxx mutant CD19-targeted CAR T cells were cocultured with NALM6gL at an E: T of 1:15 and 1:30. Five days later, exhaustion marker (LAG3, TIM3 and PD1) expression the CAR T cells was assessed by flow cytometry. CD28-Yxxx mutant CD19-targeted CAR T cells had a favorable exhaustion immunophenotype (FIG. 20).

To show the in vivo anti-tumor effects of CD28 mutant CAR T cells, NCG mice were inoculated with $1\times10^6$ NALM6gfp$^+$ffLUC$^+$ tumor cells, and were treated with 500,000 or 200,000 CAR T cells 4 days later. CD28-Yxxx mutant CD19-targeted CAR T cells demonstrated enhanced tumor control in vivo, and outperformed standard CD28-based CAR T cells (FIGS. 21 and 22).

CD28-Yxxx mutant CD19-targeted CAR T cells displayed enhanced proliferation in vitro independent of antigen-density. Human CD19-targeted CD28-Yxxx mutant CAR T cells were cocultured with NALM6gL with either high or low CD19 antigen density at an E:T ratio of 1:1. Every 6 days, CAR$^+$ T cells were counted and re-stimulated with NALM6gL, for a total of three stimulations. CD28-Yxxx Mutant CD19-targeted CAR T cells showed enhanced proliferation against standard CD28-based CAR T cells in vitro in the context of both high- and low-antigen density CD19 tumor cells (FIG. 23).

Cytokine secretion profiles of CD28-Yxxx mutant CD19-targeted CAR T cells were measured. Human CD19-targeted CD28-Yxxx mutant CAR T cells were cocultured with NALM6gL. Twenty-four hours later, supernatant was collected and cytokines, including interleukin-2, TNF-α, GM-CSF, interferon-y, IL-9, and IL-17 were measured by the Luminex bead-based multiplex assay. CD28-Yxxx mutant CD19-targeted CAR T cells demonstrated unique cytokine secretion profiles on exposure to antigens (FIGS. 24A-24C).

Although the presently disclosed subject matter and certain of its advantages have been described in detail, it should be understood that various changes, substitutions and alterations can be made herein without departing from the spirit and scope of the disclosure. Moreover, the scope of the present application is not intended to be limited to the particular embodiments of the process, machine, manufacture, and composition of matter, and methods described in the specification. As one of ordinary skill in the art will readily appreciate from the disclosure of the presently disclosed subject matter, processes, machines, manufacture, compositions of matter, or methods, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, or methods.

Various patents, patent applications, publications, product descriptions, protocols, and sequence accession numbers are cited throughout this application, the disclosure of which are incorporated herein by reference in their entireties for all purposes.

SEQUENCE LISTING

```
Sequence total quantity: 87
SEQ ID NO: 1            moltype = AA  length = 272
FEATURE                 Location/Qualifiers
source                  1..272
                        mol_type = protein
                        organism = Homo sapiens
SEQUENCE: 1
PEEPLVVKVE EGDNAVLQCL KGTSDGPTQQ LTWSRESPLK PFLKLSLGLP GLGIHMRPLA  60
IWLFIFNVSQ QMGGFYLCQP GPPSEKAWQP GWTVNVEGSG ELFRWNVSDL GGLGCGLKNR  120
SSEGPSSPSG KLMSPKLYVW AKDRPEIWEG EPPCLPPRDS LNQSLSQDLT MAPGSTLWLS  180
CGVPPDSVSR GPLSWTHVHP KGPKSLLSLE LKDDRPARDM WVMETGLLLP RATAQDAGKY  240
YCHRGNLTMS FHLEITARPV LWHWLLRTGG WK                                272

SEQ ID NO: 2            moltype = AA  length = 245
FEATURE                 Location/Qualifiers
REGION                  1..245
                        note = Synthetic
source                  1..245
                        mol_type = protein
                        organism = synthetic construct
SEQUENCE: 2
EVKLQQSGAE LVRPGSSVKI SCKASGYAFS SYWMNWVKQR PGQGLEWIGQ IYPGDGDTNY  60
NGKFKGQATL TADKSSSTAY MQLSGLTSED SAVYFCARKT ISSVVDFYFD YWGQGTTVTV  120
SSGGGGSGGG GSGGGGSDIE LTQSPKFMST SVGDRVSVTC KASQNVGTNV AWYQQKPGQS  180
PKPLIYSATY RNSGVPDRFT GSGSGTDFTL TITNVQSKDL ADYFCQQYNR YPYTSGGGTK  240
LEIKR                                                              245

SEQ ID NO: 3            moltype = AA  length = 122
FEATURE                 Location/Qualifiers
REGION                  1..122
                        note = Synthetic
source                  1..122
                        mol_type = protein
                        organism = synthetic construct
SEQUENCE: 3
EVKLQQSGAE LVRPGSSVKI SCKASGYAFS SYWMNWVKQR PGQGLEWIGQ IYPGDGDTNY  60
NGKFKGQATL TADKSSSTAY MQLSGLTSED SAVYFCARKT ISSVVDFYFD YWGQGTTVTV  120
SS                                                                 122

SEQ ID NO: 4            moltype = AA  length = 108
FEATURE                 Location/Qualifiers
REGION                  1..108
                        note = Synthetic
source                  1..108
                        mol_type = protein
                        organism = synthetic construct
SEQUENCE: 4
DIELTQSPKF MSTSVGDRVS VTCKASQNVG TNVAWYQQKP GQSPKPLIYS ATYRNSGVPD  60
RFTGSGSGTD FTLTITNVQS KDLADYFCQQ YNRYPYTSGG GTKLEIKR               108

SEQ ID NO: 5            moltype = AA  length = 15
FEATURE                 Location/Qualifiers
REGION                  1..15
                        note = Synthetic
source                  1..15
                        mol_type = protein
                        organism = synthetic construct
SEQUENCE: 5
GGGGSGGGGS GGGGS                                                   15
```

-continued

```
SEQ ID NO: 6            moltype = AA  length = 6
FEATURE                 Location/Qualifiers
REGION                  1..6
                        note = Synthetic
source                  1..6
                        mol_type = protein
                        organism = synthetic construct
SEQUENCE: 6
GYAFSS                                                                    6

SEQ ID NO: 7            moltype = AA  length = 6
FEATURE                 Location/Qualifiers
REGION                  1..6
                        note = Synthetic
source                  1..6
                        mol_type = protein
                        organism = synthetic construct
SEQUENCE: 7
YPGDGD                                                                    6

SEQ ID NO: 8            moltype = AA  length = 9
FEATURE                 Location/Qualifiers
REGION                  1..9
                        note = Synthetic
source                  1..9
                        mol_type = protein
                        organism = synthetic construct
SEQUENCE: 8
KTISSVVDF                                                                 9

SEQ ID NO: 9            moltype = AA  length = 7
FEATURE                 Location/Qualifiers
REGION                  1..7
                        note = Synthetic
source                  1..7
                        mol_type = protein
                        organism = synthetic construct
SEQUENCE: 9
NVGTNVA                                                                   7

SEQ ID NO: 10           moltype = AA  length = 6
FEATURE                 Location/Qualifiers
REGION                  1..6
                        note = Synthetic
source                  1..6
                        mol_type = protein
                        organism = synthetic construct
SEQUENCE: 10
SATYRN                                                                    6

SEQ ID NO: 11           moltype = AA  length = 8
FEATURE                 Location/Qualifiers
REGION                  1..8
                        note = Synthetic
source                  1..8
                        mol_type = protein
                        organism = synthetic construct
SEQUENCE: 11
FCQQYNRY                                                                  8

SEQ ID NO: 12           moltype = AA  length = 220
FEATURE                 Location/Qualifiers
REGION                  1..220
                        note = Synthetic
source                  1..220
                        mol_type = protein
                        organism = synthetic construct
SEQUENCE: 12
MLRLLLALNL FPSIQVTGNK ILVKQSPMLV AYDNAVNLSC KYSYNLFSRE FRASLHKGLD  60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                        220

SEQ ID NO: 13           moltype = AA  length = 81
FEATURE                 Location/Qualifiers
REGION                  1..81
                        note = Synthetic
source                  1..81
                        mol_type = protein
```

```
                         organism = synthetic construct
SEQUENCE: 13
TTTTGGGTGC TGGTGGTGGT TGGTGGAGTC CTGGCTTGCT ATAGCTTGCT AGTAACAGTG  60
GCCTTTATTA TTTTCTGGGT G                                            81

SEQ ID NO: 14            moltype = AA  length = 218
FEATURE                  Location/Qualifiers
REGION                   1..218
                         note = Synthetic
source                   1..218
                         mol_type = protein
                         organism = synthetic construct
SEQUENCE: 14
MTLRLLFLAL NFFSVQVTEN KILVKQSPLL VVDSNEVSLS CRYSYNLLAK EFRASLYKGV  60
NSDVEVCVGN GNFTYQPQFR SNAEFNCDGD FDNETVTFRL WNLHVNHTDI YFCKIEFMYP  120
PPYLDNERSN GTIIHIKEKH LCHTQSSPKL FWALVVVAGV LFCYGLLVTV ALCVIWTNSR  180
RNRLLQSDYM NMTPRRPGLT RKPYQPYAPA RDFAAYRP                          218

SEQ ID NO: 15            moltype = AA  length = 235
FEATURE                  Location/Qualifiers
REGION                   1..235
                         note = Synthetic
source                   1..235
                         mol_type = protein
                         organism = synthetic construct
SEQUENCE: 15
MALPVTALLL PLALLLHAAR PSQFRVSPLD RTWNLGETVE LKCQVLLSNP TSGCSWLFQP  60
RGAAASPTFL LYLSQNKPKA AEGLDTQRFS GKRLGDTFVL TLSDFRRENE GYYFCSALSN  120
SIMYFSHFVP VFLPAKPTTT PAPRPPTPAP TIASQPLSLR PEACRPAAGG AVHTRGLDFA  180
CDIYIWAPLA GTCGVLLLSL VITLYCNHRN RRRVCKCPRP VVKSGDKPSL SARYV       235

SEQ ID NO: 16            moltype = AA  length = 247
FEATURE                  Location/Qualifiers
REGION                   1..247
                         note = Synthetic
source                   1..247
                         mol_type = protein
                         organism = synthetic construct
SEQUENCE: 16
MASPLTRFLS LNLLLMGESI ILGSGEAKPQ APELRIFPKK MDAELGQKVD LVCEVLGSVS  60
QGCSWLFQNS SSKLPQPTFV VYMASSHNKI TWDEKLNSSK LFSAVRDTNN KYVLTLNKFS  120
KENEGYYFCS VISNSVMYFS SVVPVLQKVN STTTKPVLRT PSPVHPTGTS QPQRPEDCRP  180
RGSVKGTGLD FACDIYIWAP LAGICVAPLL SLIITLICYH RSRKRVCKCP RPLVRQEGKP  240
RPSEKIV                                                            247

SEQ ID NO: 17            moltype = AA  length = 164
FEATURE                  Location/Qualifiers
REGION                   1..164
                         note = Synthetic
source                   1..164
                         mol_type = protein
                         organism = synthetic construct
SEQUENCE: 17
MKWKALFTAA ILQAQLPITE AQSFGLLDPK LCYLLDGILF IYGVILTALF LRVKFSRSAD  60
APAYQQGQNQ LYNELNLGRR EEYDVLDKRR GRDPEMGGKP QRRKNPQEGL YNELQKDKMA  120
EAYSEIGMKG ERRRGKGHDG LYQGLSTATK DTYDALHMQA LPPR                   164

SEQ ID NO: 18            moltype = AA  length = 112
FEATURE                  Location/Qualifiers
REGION                   1..112
                         note = Synthetic
source                   1..112
                         mol_type = protein
                         organism = synthetic construct
SEQUENCE: 18
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 19            moltype = AA  length = 4
FEATURE                  Location/Qualifiers
REGION                   1..4
                         note = Synthetic
source                   1..4
                         mol_type = protein
                         organism = synthetic construct
SEQUENCE: 19
YMNM                                                               4

SEQ ID NO: 20            moltype =   length =
```

```
SEQUENCE: 20
000

SEQ ID NO: 21          moltype =   length =
SEQUENCE: 21
000

SEQ ID NO: 22          moltype = AA  length = 4
FEATURE                Location/Qualifiers
REGION                 1..4
                       note = Synthetic
source                 1..4
                       mol_type = protein
                       organism = synthetic construct
SEQUENCE: 22
YENV                                                          4

SEQ ID NO: 23          moltype = AA  length = 4
FEATURE                Location/Qualifiers
REGION                 1..4
                       note = Synthetic
source                 1..4
                       mol_type = protein
                       organism = synthetic construct
SEQUENCE: 23
YSNV                                                          4

SEQ ID NO: 24          moltype = AA  length = 4
FEATURE                Location/Qualifiers
REGION                 1..4
                       note = Synthetic
source                 1..4
                       mol_type = protein
                       organism = synthetic construct
SEQUENCE: 24
YKNL                                                          4

SEQ ID NO: 25          moltype = AA  length = 4
FEATURE                Location/Qualifiers
REGION                 1..4
                       note = Synthetic
source                 1..4
                       mol_type = protein
                       organism = synthetic construct
SEQUENCE: 25
YENQ                                                          4

SEQ ID NO: 26          moltype = AA  length = 4
FEATURE                Location/Qualifiers
REGION                 1..4
                       note = Synthetic
source                 1..4
                       mol_type = protein
                       organism = synthetic construct
SEQUENCE: 26
YKNI                                                          4

SEQ ID NO: 27          moltype = AA  length = 4
FEATURE                Location/Qualifiers
REGION                 1..4
                       note = Synthetic
source                 1..4
                       mol_type = protein
                       organism = synthetic construct
SEQUENCE: 27
YINQ                                                          4

SEQ ID NO: 28          moltype = AA  length = 4
FEATURE                Location/Qualifiers
REGION                 1..4
                       note = Synthetic
source                 1..4
                       mol_type = protein
                       organism = synthetic construct
SEQUENCE: 28
YHNK                                                          4

SEQ ID NO: 29          moltype = AA  length = 4
FEATURE                Location/Qualifiers
```

```
REGION                1..4
                      note = Synthetic
source                1..4
                      mol_type = protein
                      organism = synthetic construct
SEQUENCE: 29
YVNQ                                                                        4

SEQ ID NO: 30         moltype = AA  length = 4
FEATURE               Location/Qualifiers
REGION                1..4
                      note = Synthetic
source                1..4
                      mol_type = protein
                      organism = synthetic construct
SEQUENCE: 30
YLNP                                                                        4

SEQ ID NO: 31         moltype = AA  length = 4
FEATURE               Location/Qualifiers
REGION                1..4
                      note = Synthetic
source                1..4
                      mol_type = protein
                      organism = synthetic construct
SEQUENCE: 31
YLNT                                                                        4

SEQ ID NO: 32         moltype = AA  length = 4
FEATURE               Location/Qualifiers
REGION                1..4
                      note = Synthetic
source                1..4
                      mol_type = protein
                      organism = synthetic construct
SEQUENCE: 32
YMDM                                                                        4

SEQ ID NO: 33         moltype =   length =
SEQUENCE: 33
000

SEQ ID NO: 34         moltype = AA  length = 4
FEATURE               Location/Qualifiers
REGION                1..4
                      note = Synthetic
source                1..4
                      mol_type = protein
                      organism = synthetic construct
SEQUENCE: 34
YTHM                                                                        4

SEQ ID NO: 35         moltype = AA  length = 4
FEATURE               Location/Qualifiers
REGION                1..4
                      note = Synthetic
source                1..4
                      mol_type = protein
                      organism = synthetic construct
SEQUENCE: 35
YVLM                                                                        4

SEQ ID NO: 36         moltype = AA  length = 4
FEATURE               Location/Qualifiers
REGION                1..4
                      note = Synthetic
source                1..4
                      mol_type = protein
                      organism = synthetic construct
SEQUENCE: 36
YIAM                                                                        4

SEQ ID NO: 37         moltype = AA  length = 4
FEATURE               Location/Qualifiers
REGION                1..4
                      note = Synthetic
source                1..4
                      mol_type = protein
                      organism = synthetic construct
```

```
SEQUENCE: 37
YMRM                                                                    4

SEQ ID NO: 38           moltype =   length =
SEQUENCE: 38
000

SEQ ID NO: 39           moltype =   length =
SEQUENCE: 39
000

SEQ ID NO: 40           moltype = AA  length = 4
FEATURE                 Location/Qualifiers
REGION                  1..4
                        note = Synthetic
source                  1..4
                        mol_type = protein
                        organism = synthetic construct
SEQUENCE: 40
YMNV                                                                    4

SEQ ID NO: 41           moltype = AA  length = 4
FEATURE                 Location/Qualifiers
REGION                  1..4
                        note = Synthetic
source                  1..4
                        mol_type = protein
                        organism = synthetic construct
SEQUENCE: 41
YENM                                                                    4

SEQ ID NO: 42           moltype = AA  length = 4
FEATURE                 Location/Qualifiers
REGION                  1..4
                        note = Synthetic
source                  1..4
                        mol_type = protein
                        organism = synthetic construct
SEQUENCE: 42
YMNQ                                                                    4

SEQ ID NO: 43           moltype =   length =
SEQUENCE: 43
000

SEQ ID NO: 44           moltype = AA  length = 4
FEATURE                 Location/Qualifiers
REGION                  1..4
                        note = Synthetic
source                  1..4
                        mol_type = protein
                        organism = synthetic construct
SEQUENCE: 44
YGGG                                                                    4

SEQ ID NO: 45           moltype = AA  length = 4
FEATURE                 Location/Qualifiers
REGION                  1..4
                        note = Synthetic
source                  1..4
                        mol_type = protein
                        organism = synthetic construct
SEQUENCE: 45
YAAA                                                                    4

SEQ ID NO: 46           moltype = AA  length = 4
FEATURE                 Location/Qualifiers
REGION                  1..4
                        note = Synthetic
source                  1..4
                        mol_type = protein
                        organism = synthetic construct
SEQUENCE: 46
YFFF                                                                    4

SEQ ID NO: 47           moltype = AA  length = 41
FEATURE                 Location/Qualifiers
REGION                  1..41
                        note = Synthetic
```

```
source                  1..41
                        mol_type = protein
                        organism = synthetic construct
SEQUENCE: 47
RSKRSRLLHS DYENVTPRRP GPTRKHYQPY APPRDFAAYR S                   41

SEQ ID NO: 48           moltype = AA  length = 41
FEATURE                 Location/Qualifiers
REGION                  1..41
                        note = Synthetic
source                  1..41
                        mol_type = protein
                        organism = synthetic construct
SEQUENCE: 48
RSKRSRLLHS DYKNITPRRP GPTRKHYQPY APPRDFAAYR S                   41

SEQ ID NO: 49           moltype = AA  length = 41
FEATURE                 Location/Qualifiers
REGION                  1..41
                        note = Synthetic
source                  1..41
                        mol_type = protein
                        organism = synthetic construct
SEQUENCE: 49
RSKRSRLLHS DYMDMTPRRP GPTRKHYQPY APPRDFAAYR S                   41

SEQ ID NO: 50           moltype = AA  length = 255
FEATURE                 Location/Qualifiers
REGION                  1..255
                        note = Synthetic
source                  1..255
                        mol_type = protein
                        organism = synthetic construct
SEQUENCE: 50
MGNSCYNIVA TLLLVLNFER TRSLQDPCSN CPAGTFCDNN RNQICSPCPP NSFSSAGGQR  60
TCDICRQCKG VFRTRKECSS TSNAECDCTP GFHCLGAGCS MCEQDCKQGQ ELTKKGCKDC  120
CFGTFNDQKR GICRPWTNCS LDGKSVLVNG TKERDVVCGP SPADLSPGAS SVTPPAPARE  180
PGHSPQIISF FLALTSTALL FLLFFLTLRF SVVKRGRKKL LYIFKQPFMR PVQTTQEEDG  240
CSCRFPEEEE GGCEL                                                255

SEQ ID NO: 51           moltype = AA  length = 467
FEATURE                 Location/Qualifiers
REGION                  1..467
                        note = Synthetic
source                  1..467
                        mol_type = protein
                        organism = synthetic construct
SEQUENCE: 51
EVKLQQSGAE LVRPGSSVKI SCKASGYAFS SYWMNWVKQR PGQGLEWIGQ IYPGDGDTNY  60
NGKFKGQATL TADKSSSTAY MQLSGLTSED SAVYFCARKT ISSVVDFYFD YWGQGTTVTV  120
SSGGGGSGGG GSGGGGSDIE LTQSPKFMST SVGDRVSVTC KASQNVGTNV AWYQQKPGQS  180
PKPLIYSATY RNSGVPDRFT GSGSGTDFTL TITNVQSKDL ADYFCQQYNR YPYTSGGGTK  240
LEIKRAAAIE VMYPPPYLDN EKSNGTIIHV KGKHLCPSPL FPGPSKPFWV LVVVGGVLAC  300
YSLLVTVAFI IFWVRSKRSR LLHSDYMDMT PRRPGPTRKH YQPYAPPRDF AAYRSRVKFS  360
RSADAPAYQQ GQNQLYNELN LGRREEYDVL DKRRGRDPEM GGKPRRKNPQ EGLYNELQKD  420
KMAEAYSEIG MKGERRRGKG HDGLYQGLST ATKDTYDALH MQALPPR              467

SEQ ID NO: 52           moltype = DNA  length = 1401
FEATURE                 Location/Qualifiers
misc_feature            1..1401
                        note = Synthetic
source                  1..1401
                        mol_type = other DNA
                        organism = synthetic construct
SEQUENCE: 52
gaggtgaagc tgcagcagtc tggggctgag ctggtgaggc ctgggtcctc agtgaagatt  60
tcctgcaagg cttctggcta tgcattcagt agctactgga tgaactgggt gaagcagagg  120
cctggacagg gtcttgagtg gattggacag atttatcctg gagatggtga tactaactac  180
aatggaaagt tcaagggtca agccacactg actgcagaca aatcctccag cacagcctac  240
atgcagctca gcggcctaac atctgaggac tctgcggtct atttctgtgc aagaaagacc  300
attagttcgg tagtagattt ctactttgac tactggggcc aagggaccac ggtcaccgtc  360
tcctcaggtg gaggtggatc aggtggaggt ggatctggtg gaggtggatc tgacattgag  420
ctcacccagt ctccaaaatt catgtccaca tcagtaggag acagggtcag cgtcacctgc  480
aaggccagtc agaatgtggg tactaatgta gcctggtatc aacagaaacc aggacaatct  540
cctaaaccac tgatttactc ggcaacctac cggaacagtg gagtccctga tcgcttcaca  600
ggcagtggat ctgggacaga tttcactctc accatcacta acgtgcagtc taaagacttg  660
gcagactatt tctgtcaaca atataacagg tatccgtaca cgtccggagg ggggaccaag  720
ctggagatca aacgggcggc cgcaattgaa gttatgtatc ctcctcctta cctagacaat  780
gagaagagca atggaaccat tatccatgtg aaagggaaac acctttgtcc aagtccccta  840
```

```
tttcccggac cttctaagcc cttttgggtg ctggtggtgg ttggtggagt cctggcttgc  900
tatagcttgc tagtaacagt ggcctttatt attttctggg tgaggagtaa gaggagcagg  960
ctcctgcaca gtgactacat ggatatgact ccccgccgcc ccgggcccac ccgcaagcat  1020
taccagccct atgccccacc acgcgacttc gcagcctatc gctccagagt gaagttcagc  1080
aggagcgcag acgcccccgc gtaccagcag ggccagaacc agctctataa cgagctcaat  1140
ctaggacgaa gagaggagta cgatgttttg gacaagagac gtggccggga ccctgagatg  1200
gggggaaagc cgagaaggaa gaaccctcag gaaggcctgt acaatgaact gcagaaagat  1260
aagatggcgg aggcctacag tgagattggg atgaaaggcg agcgccggag gggcaagggg  1320
cacgatggcc tttaccaggg tctcagtaca gccaccaagg acacctacga cgcccttcac  1380
atgcaggccc tgccccctcg c                                            1401

SEQ ID NO: 53          moltype = AA  length = 467
FEATURE                Location/Qualifiers
REGION                 1..467
                       note = Synthetic
source                 1..467
                       mol_type = protein
                       organism = synthetic construct
SEQUENCE: 53
EVKLQQSGAE LVRPGSSVKI SCKASGYAFS SYWMNWVKQR PGQGLEWIGQ IYPGDGDTNY  60
NGKFKGQATL TADKSSSTAY MQLSGLTSED SAVYFCARKT ISSVVDFYFD YWGQGTTVTV  120
SSGGGGSGGG GSGGGGSDIE LTQSPKFMST SVGDRVSVTC KASQNVGTNV AWYQQKPGQS  180
PKPLIYSATY RNSGVPDRFT GSGSGTDFTL TITNVQSKDL ADYFCQQYNR YPYTSGGGTK  240
LEIKRAAAIE VMYPPPYLDN EKSNGTIIHV KGKHLCPSPL FPGPSKPFWV LVVVGGVLAC  300
YSLLVTVAFI IFWVRSKRSR LLHSDYENVT PRRPGPTRKH YQPYAPPRDF AAYRSRVKFS  360
RSADAPAYQQ GQNQLYNELN LGRREEYDVL DKRRGRDPEM GGKPRRKNPQ EGLYNELQKD  420
KMAEAYSEIG MKGERRRGKG HDGLYQGLST ATKDTYDALH MQALPPR                467

SEQ ID NO: 54          moltype = DNA  length = 1404
FEATURE                Location/Qualifiers
misc_feature           1..1404
                       note = Synthetic
source                 1..1404
                       mol_type = other DNA
                       organism = synthetic construct
SEQUENCE: 54
gaggtgaagc tgcagcagtc tggggctgag ctggtgaggc ctgggtcctc agtgaagatt  60
tcctgcaagg cttctggcta tgcattcagt agctactgga tgaactgggt gaagcagagg  120
cctggacagg gtcttgagtg gattggacag atttatcctg gagatggtga tactaactac  180
aatggaaagt tcaagggtca agccacactg actgcagaca aatcctccag cacagcctac  240
atgcagctca gcggcctaac atctgaggac tctgcggtct atttctgtgc aagaaagacc  300
attagttcgg tagtagattt ctactttgac tactggggcc aagggaccac ggtcaccgtc  360
tcctcaggtg gaggtggatc aggtggaggt ggatctggtg gaggtggatc tgacattgag  420
ctcacccagt ctccaaaatt catgtccaca tcagtaggag acagggtcag cgtcacctgc  480
aaggccagtc agaatgtggg tactaatgta gcctggtatc aacagaaacc aggacaatct  540
cctaaaccac tgatttactc ggcaacctac cggaacagtg gagtccctga tcgcttcaca  600
ggcagtggat ctgggacaga tttcactctc accatcacta acgtgcagtc taaagacttg  660
gcagactatt tctgtcaaca atataacagg tatccgtaca cgtccggagg ggggaccaag  720
ctggagatca aacgggcggc cgcaattgaa gttatgtatc ctcctcctta cctagacaat  780
gagaagagca atggaaccat tatccatgtg aaagggaaac acctttgtcc aagtccccta  840
tttcccggac cttctaagcc cttttgggtg ctggtggtgg ttggtggagt cctggcttgc  900
tatagcttgc tagtaacagt ggcctttatt attttctggg tgaggagtaa gaggagcagg  960
ctcctgcaca gtgactatga aaatgtgact ccccgccgcc ccgggcccac ccgcaagcat  1020
taccagccct atgccccacc acgcgacttc gcagcctatc gctccagagt gaagttcagc  1080
aggagcgcag acgcccccgc gtaccagcag ggccagaacc agctctataa cgagctcaat  1140
ctaggacgaa gagaggagta cgatgttttg gacaagagac gtggccggga ccctgagatg  1200
gggggaaagc cgagaaggaa gaaccctcag gaaggcctgt acaatgaact gcagaaagat  1260
aagatggcgg aggcctacag tgagattggg atgaaaggcg agcgccggag gggcaagggg  1320
cacgatggcc tttaccaggg tctcagtaca gccaccaagg acacctacga cgcccttcac  1380
atgcaggccc tgccccctcg ctag                                         1404

SEQ ID NO: 55          moltype = AA  length = 467
FEATURE                Location/Qualifiers
REGION                 1..467
                       note = Synthetic
source                 1..467
                       mol_type = protein
                       organism = synthetic construct
SEQUENCE: 55
EVKLQQSGAE LVRPGSSVKI SCKASGYAFS SYWMNWVKQR PGQGLEWIGQ IYPGDGDTNY  60
NGKFKGQATL TADKSSSTAY MQLSGLTSED SAVYFCARKT ISSVVDFYFD YWGQGTTVTV  120
SSGGGGSGGG GSGGGGSDIE LTQSPKFMST SVGDRVSVTC KASQNVGTNV AWYQQKPGQS  180
PKPLIYSATY RNSGVPDRFT GSGSGTDFTL TITNVQSKDL ADYFCQQYNR YPYTSGGGTK  240
LEIKRAAAIE VMYPPPYLDN EKSNGTIIHV KGKHLCPSPL FPGPSKPFWV LVVVGGVLAC  300
YSLLVTVAFI IFWVRSKRSR LLHSDYKNIT PRRPGPTRKH YQPYAPPRDF AAYRSRVKFS  360
RSADAPAYQQ GQNQLYNELN LGRREEYDVL DKRRGRDPEM GGKPRRKNPQ EGLYNELQKD  420
KMAEAYSEIG MKGERRRGKG HDGLYQGLST ATKDTYDALH MQALPPR                467

SEQ ID NO: 56          moltype = DNA  length = 1401
```

```
FEATURE               Location/Qualifiers
misc_feature          1..1401
                      note = Synthetic
source                1..1401
                      mol_type = other DNA
                      organism = synthetic construct
SEQUENCE: 56
gaggtgaagc tgcagcagtc tggggctgag ctggtgaggc ctgggtcctc agtgaagatt  60
tcctgcaagg cttctggcta tgcattcagt agctactgga tgaactgggt gaagcagagg  120
cctggacagg gtcttgagtg gattggacag atttatcctg gagatggtga tactaactac  180
aatggaaagt tcaagggtca agccacactg actgcagaca aatcctccag cacagcctac  240
atgcagctca gcggcctaac atctgaggac tctgcggtct atttctgtgc aagaaagacc  300
attagttcgg tagtagattt ctactttgac tactggggcc aagggaccac ggtcaccgtc  360
tcctcaggtg gaggtggatc aggtggaggt ggatctggtg gaggtggatc tgacattgag  420
ctcacccagt ctccaaaatt catgtccaca tcagtaggag acagggtcag cgtcacctgc  480
aaggccagtc agaatgtggg tactaatgta gcctggtatc aacagaaacc aggacaatct  540
cctaaaccac tgatttactc ggcaacctac cggaacagtg gagtccctga tcgcttcaca  600
ggcagtggat ctgggacaga tttcactctc accatcacta acgtgcagtc taaagacttg  660
gcagactatt tctgtcaaca atataacagg tatccgtaca cgtccggagg ggggaccaag  720
ctggagatca aacgggcggc cgcaattgaa gttatgtatc ctcctcctta cctagacaat  780
gagaagagca atggaaccat tatccatgtg aaagggaaac acctttgtcc aagtccccta  840
tttcccggac cttctaagcc cttttgggtg ctggtggtgg ttggtggagt cctggcttgc  900
tatagcttgc tagtaacagt ggcctttatt attttctggg tgaggagtaa gaggagcagg  960
ctcctgcaca gtgactataa aaacattact ccccgccgcc ccgggcccac ccgcaagcat  1020
taccagccct atgccccacc acgcgacttc gcagcctatc gctccagagt gaagttcagc  1080
aggagcgcag acgcccccgc gtaccagcag ggccagaacc agctctataa cgagctcaat  1140
ctaggacgaa gagaggagta cgatgttttg gacaagagac gtggccggga ccctgagatg  1200
gggggaaagc cgagaaggaa gaaccctcag gaaggcctgt acaatgaact gcagaaagat  1260
aagatggcgg aggcctacag tgagattggg atgaaaggcg agcgccggag gggcaagggg  1320
cacgatggcc tttaccaggg tctcagtaca gccaccaagg acacctacga cgcccttcac  1380
atgcaggccc tgccccctcg c                                            1401

SEQ ID NO: 57         moltype = AA  length = 467
FEATURE               Location/Qualifiers
REGION                1..467
                      note = Synthetic
source                1..467
                      mol_type = protein
                      organism = synthetic construct
SEQUENCE: 57
EVKLQQSGAE LVRPGSSVKI SCKASGYAFS SYWMNWVKQR PGQGLEWIGQ IYPGDGDTNY  60
NGKFKGQATL TADKSSSTAY MQLSGLTSED SAVYFCARKT ISSVVDFYFD YWGQGTTVTV  120
SSGGGGSGGG GSGGGGSDIE LTQSPKFMST SVGDRVSVTC KASQNVGTNV AWYQQKPGQS  180
PKPLIYSATY RNSGVPDRFT GSGSGTDFTL TITNVQSKDL ADYFCQQYNR YPYTSGGGTK  240
LEIKRAAAIE VMYPPPYLDN EKSNGTIIHV KGKHLCPSPL FPGPSKPFWV LVVVGGVLAC  300
YSLLVTVAFI IFWVRSKRSR LLHSDYSNVT PRRPGPTRKH YQPYAPPRDF AAYRSRVKFS  360
RSADAPAYQQ GQNQLYNELN LGRREEYDVL DKRRGRDPEM GGKPRRKNPQ EGLYNELQKD  420
KMAEAYSEIG MKGERRRGKG HDGLYQGLST ATKDTYDALH MQALPPR                467

SEQ ID NO: 58         moltype = DNA  length = 1401
FEATURE               Location/Qualifiers
misc_feature          1..1401
                      note = Synthetic
source                1..1401
                      mol_type = other DNA
                      organism = synthetic construct
SEQUENCE: 58
gaggtgaagc tgcagcagtc tggggctgag ctggtgaggc ctgggtcctc agtgaagatt  60
tcctgcaagg cttctggcta tgcattcagt agctactgga tgaactgggt gaagcagagg  120
cctggacagg gtcttgagtg gattggacag atttatcctg gagatggtga tactaactac  180
aatggaaagt tcaagggtca agccacactg actgcagaca aatcctccag cacagcctac  240
atgcagctca gcggcctaac atctgaggac tctgcggtct atttctgtgc aagaaagacc  300
attagttcgg tagtagattt ctactttgac tactggggcc aagggaccac ggtcaccgtc  360
tcctcaggtg gaggtggatc aggtggaggt ggatctggtg gaggtggatc tgacattgag  420
ctcacccagt ctccaaaatt catgtccaca tcagtaggag acagggtcag cgtcacctgc  480
aaggccagtc agaatgtggg tactaatgta gcctggtatc aacagaaacc aggacaatct  540
cctaaaccac tgatttactc ggcaacctac cggaacagtg gagtccctga tcgcttcaca  600
ggcagtggat ctgggacaga tttcactctc accatcacta acgtgcagtc taaagacttg  660
gcagactatt tctgtcaaca atataacagg tatccgtaca cgtccggagg ggggaccaag  720
ctggagatca aacgggcggc cgcaattgaa gttatgtatc ctcctcctta cctagacaat  780
gagaagagca atggaaccat tatccatgtg aaagggaaac acctttgtcc aagtccccta  840
tttcccggac cttctaagcc cttttgggtg ctggtggtgg ttggtggagt cctggcttgc  900
tatagcttgc tagtaacagt ggcctttatt attttctggg tgaggagtaa gaggagcagg  960
ctcctgcaca gtgactactc aaatgttact ccccgccgcc ccgggcccac ccgcaagcat  1020
taccagccct atgccccacc acgcgacttc gcagcctatc gctccagagt gaagttcagc  1080
aggagcgcag acgcccccgc gtaccagcag ggccagaacc agctctataa cgagctcaat  1140
ctaggacgaa gagaggagta cgatgttttg gacaagagac gtggccggga ccctgagatg  1200
gggggaaagc cgagaaggaa gaaccctcag gaaggcctgt acaatgaact gcagaaagat  1260
aagatggcgg aggcctacag tgagattggg atgaaaggcg agcgccggag gggcaagggg  1320
```

```
cacgatggcc tttaccaggg tctcagtaca gccaccaagg acacctacga cgcccttcac  1380
atgcaggccc tgccccctcg c                                            1401

SEQ ID NO: 59           moltype = AA  length = 467
FEATURE                 Location/Qualifiers
REGION                  1..467
                        note = Synthetic
source                  1..467
                        mol_type = protein
                        organism = synthetic construct
SEQUENCE: 59
EVKLQQSGAE LVRPGSSVKI SCKASGYAFS SYWMNWVKQR PGQGLEWIGQ IYPGDGDTNY  60
NGKFKGQATL TADKSSSTAY MQLSGLTSED SAVYFCARKT ISSVVDFYFD YWGQGTTVTV  120
SSGGGGSGGG GSGGGGSDIE LTQSPKFMST SVGDRVSVTC KASQNVGTNV AWYQQKPGQS  180
PKPLIYSATY RNSGVPDRFT GSGSGTDFTL TITNVQSKDL ADYFCQQYNR YPYTSGGGTK  240
LEIKRAAAIE VMYPPPYLDN EKSNGTIIHV KGKHLCPSPL FPGPSKPFWV LVVVGGVLAC  300
YSLLVTVAFI IFWVRSKRSR LLHSDYKNLT PRRPGPTRKH YQPYAPPRDF AAYRSRVKFS  360
RSADAPAYQQ GQNQLYNELN LGRREEYDVL DKRRGRDPEM GGKPRRKNPQ EGLYNELQKD  420
KMAEAYSEIG MKGERRRGKG HDGLYQGLST ATKDTYDALH MQALPPR                467

SEQ ID NO: 60           moltype = DNA  length = 1401
FEATURE                 Location/Qualifiers
misc_feature            1..1401
                        note = Synthetic
source                  1..1401
                        mol_type = other DNA
                        organism = synthetic construct
SEQUENCE: 60
gaggtgaagc tgcagcagtc tggggctgag ctggtgaggc ctgggtcctc agtgaagatt  60
tcctgcaagg cttctggcta tgcattcagt agctactgga tgaactgggt gaagcagagg  120
cctggacagg gtcttgagtg gattggacag atttatcctg gagatggtga tactaactac  180
aatggaaagt tcaagggtca agccacactg actgcagaca aatcctccag cacagcctac  240
atgcagctca gcggcctaac atctgaggac tctgcggtct atttctgtgc aagaaagacc  300
attagttcgg tagtagattt ctactttgac tactggggcc aagggaccac ggtcaccgtc  360
tcctcaggtg gaggtggatc aggtggaggt ggatctggtg gaggtggatc tgacattgag  420
ctcacccagt ctccaaaatt catgtccaca tcagtaggag acagggtcag cgtcacctgc  480
aaggccagtc agaatgtggg tactaatgta gcctggtatc aacagaaacc aggacaatct  540
cctaaaccac tgatttactc ggcaacctac cggaacagtg gagtccctga tcgcttcaca  600
ggcagtggat ctgggacaga tttcactctc accatcacta acgtgcagtc taaagacttg  660
gcagactatt tctgtcaaca atataacagg tatccgtaca cgtccggagg ggggaccaag  720
ctggagatca aacgggcggc cgcaattgaa gttatgtatc ctcctcctta cctagacaat  780
gagaagagca atggaaccat tatccatgtg aaagggaaac acctttgtcc aagtccccta  840
tttcccggac cttctaagcc cttttgggtg ctggtggtgg ttggtggagt cctggcttgc  900
tatagcttgc tagtaacagt ggcctttatt attttctggg tgaggagtaa gaggagcagg  960
ctcctgcaca gtgactacaa aaacttgact ccccgccgcc ccgggcccac ccgcaagcat  1020
taccagccct atgccccacc acgcgacttc gcagcctatc gctccagagt gaagttcagc  1080
aggagcgcag acgcccccgc gtaccagcag ggccagaacc agctctataa cgagctcaat  1140
ctaggacgaa gagaggagta cgatgttttg gacaagagac gtggccggga ccctgagatg  1200
gggggaaagc cgagaaggaa gaaccctcag gaaggcctgt acaatgaact gcagaaagat  1260
aagatggcgg aggcctacag tgagattggg atgaaaggcg agcgccggag gggcaagggg  1320
cacgatggcc tttaccaggg tctcagtaca gccaccaagg acacctacga cgcccttcac  1380
atgcaggccc tgccccctcg c                                            1401

SEQ ID NO: 61           moltype = AA  length = 467
FEATURE                 Location/Qualifiers
REGION                  1..467
                        note = Synthetic
source                  1..467
                        mol_type = protein
                        organism = synthetic construct
SEQUENCE: 61
EVKLQQSGAE LVRPGSSVKI SCKASGYAFS SYWMNWVKQR PGQGLEWIGQ IYPGDGDTNY  60
NGKFKGQATL TADKSSSTAY MQLSGLTSED SAVYFCARKT ISSVVDFYFD YWGQGTTVTV  120
SSGGGGSGGG GSGGGGSDIE LTQSPKFMST SVGDRVSVTC KASQNVGTNV AWYQQKPGQS  180
PKPLIYSATY RNSGVPDRFT GSGSGTDFTL TITNVQSKDL ADYFCQQYNR YPYTSGGGTK  240
LEIKRAAAIE VMYPPPYLDN EKSNGTIIHV KGKHLCPSPL FPGPSKPFWV LVVVGGVLAC  300
YSLLVTVAFI IFWVRSKRSR LLHSDYGGGT PRRPGPTRKH YQPYAPPRDF AAYRSRVKFS  360
RSADAPAYQQ GQNQLYNELN LGRREEYDVL DKRRGRDPEM GGKPRRKNPQ EGLYNELQKD  420
KMAEAYSEIG MKGERRRGKG HDGLYQGLST ATKDTYDALH MQALPPR                467

SEQ ID NO: 62           moltype = DNA  length = 1401
FEATURE                 Location/Qualifiers
misc_feature            1..1401
                        note = Synthetic
source                  1..1401
                        mol_type = other DNA
                        organism = synthetic construct
SEQUENCE: 62
gaggtgaagc tgcagcagtc tggggctgag ctggtgaggc ctgggtcctc agtgaagatt  60
```

```
tcctgcaagg cttctggcta tgcattcagt agctactgga tgaactgggt gaagcagagg  120
cctggacagg gtcttgagtg gattggacag atttatcctg gagatggtga tactaactac  180
aatggaaagt tcaagggtca agccacactg actgcagaca aatcctccag cacagcctac  240
atgcagctca gcggcctaac atctgaggac tctgcggtct atttctgtgc aagaaagacc  300
attagttcgg tagtagattt ctactttgac tactggggcc aagggaccac ggtcaccgtc  360
tcctcaggtg gaggtggatc aggtggaggt ggatctggtg gaggtggatc tgacattgag  420
ctcacccagt ctccaaaatt catgtccaca tcagtaggag acagggtcag cgtcacctgc  480
aaggccagtc agaatgtggg tactaatgta gcctggtatc aacagaaacc aggacaatct  540
cctaaaccac tgatttactc ggcaacctac cggaacagtg gagtccctga tcgcttcaca  600
ggcagtggat ctgggacaga tttcactctc accatcacta acgtgcagtc taaagacttg  660
gcagactatt tctgtcaaca atataacagg tatccgtaca cgtccggagg ggggaccaag  720
ctggagatca aacgggcggc cgcaattgaa gttatgtatc ctcctcctta cctagacaat  780
gagaagagca atggaaccat tatccatgtg aaagggaaac acctttgtcc aagtccccta  840
tttcccggac cttctaagcc cttttgggtg ctggtggtgg ttggtggagt cctggcttgc  900
tatagcttgc tagtaacagt ggcctttatt attttctggg tgaggagtaa gaggagcagg  960
ctcctgcaca gtgactacgg tggagggact ccccgccgcc ccgggcccac ccgcaagcat  1020
taccagccct atgccccacc acgcgacttc gcagcctatc gctccagagt gaagttcagc  1080
aggagcgcag acgcccccgc gtaccagcag ggccagaacc agctctataa cgagctcaat  1140
ctaggacgaa gagaggagta cgatgttttg gacaagagac gtggccggga ccctgagatg  1200
gggggaaagc cgagaaggaa gaaccctcag gaaggcctgt acaatgaact gcagaaagat  1260
aagatggcgg aggcctacag tgagattggg atgaaaggcg agcgccggag gggcaagggg  1320
cacgatggcc tttaccaggg tctcagtaca gccaccaagg acacctacga cgcccttcac  1380
atgcaggccc tgccccctcg c                                            1401

SEQ ID NO: 63          moltype = AA  length = 4
FEATURE                Location/Qualifiers
REGION                 1..4
                       note = Synthetic
source                 1..4
                       mol_type = protein
                       organism = synthetic construct
SEQUENCE: 63
YGGG                                                               4

SEQ ID NO: 64          moltype = AA  length = 4
FEATURE                Location/Qualifiers
REGION                 1..4
                       note = Synthetic
source                 1..4
                       mol_type = protein
                       organism = synthetic construct
SEQUENCE: 64
YSNV                                                               4

SEQ ID NO: 65          moltype =   length =
SEQUENCE: 65
000

SEQ ID NO: 66          moltype = AA  length = 4
FEATURE                Location/Qualifiers
REGION                 1..4
                       note = Synthetic
source                 1..4
                       mol_type = protein
                       organism = synthetic construct
SEQUENCE: 66
YDND                                                               4

SEQ ID NO: 67          moltype = AA  length = 4
FEATURE                Location/Qualifiers
REGION                 1..4
                       note = Synthetic
source                 1..4
                       mol_type = protein
                       organism = synthetic construct
SEQUENCE: 67
YENI                                                               4

SEQ ID NO: 68          moltype = AA  length = 4
FEATURE                Location/Qualifiers
REGION                 1..4
                       note = Synthetic
source                 1..4
                       mol_type = protein
                       organism = synthetic construct
SEQUENCE: 68
YENL                                                               4

SEQ ID NO: 69          moltype = AA  length = 4
```

```
FEATURE                 Location/Qualifiers
REGION                  1..4
                        note = Synthetic
source                  1..4
                        mol_type = protein
                        organism = synthetic construct
SEQUENCE: 69
YETV                                                                   4

SEQ ID NO: 70           moltype = AA  length = 4
FEATURE                 Location/Qualifiers
REGION                  1..4
                        note = Synthetic
source                  1..4
                        mol_type = protein
                        organism = synthetic construct
SEQUENCE: 70
YQQQ                                                                   4

SEQ ID NO: 71           moltype = AA  length = 4
FEATURE                 Location/Qualifiers
REGION                  1..4
                        note = Synthetic
source                  1..4
                        mol_type = protein
                        organism = synthetic construct
SEQUENCE: 71
YHAE                                                                   4

SEQ ID NO: 72           moltype = AA  length = 4
FEATURE                 Location/Qualifiers
REGION                  1..4
                        note = Synthetic
source                  1..4
                        mol_type = protein
                        organism = synthetic construct
SEQUENCE: 72
YKNQ                                                                   4

SEQ ID NO: 73           moltype = AA  length = 4
FEATURE                 Location/Qualifiers
REGION                  1..4
                        note = Synthetic
source                  1..4
                        mol_type = protein
                        organism = synthetic construct
SEQUENCE: 73
YKNV                                                                   4

SEQ ID NO: 74           moltype = AA  length = 4
FEATURE                 Location/Qualifiers
REGION                  1..4
                        note = Synthetic
source                  1..4
                        mol_type = protein
                        organism = synthetic construct
SEQUENCE: 74
YLDL                                                                   4

SEQ ID NO: 75           moltype = AA  length = 4
FEATURE                 Location/Qualifiers
REGION                  1..4
                        note = Synthetic
source                  1..4
                        mol_type = protein
                        organism = synthetic construct
SEQUENCE: 75
YLIP                                                                   4

SEQ ID NO: 76           moltype = AA  length = 4
FEATURE                 Location/Qualifiers
REGION                  1..4
                        note = Synthetic
source                  1..4
                        mol_type = protein
                        organism = synthetic construct
SEQUENCE: 76
YLRV                                                                   4
```

```
SEQ ID NO: 77          moltype = AA  length = 4
FEATURE                Location/Qualifiers
REGION                 1..4
                       note = Synthetic
source                 1..4
                       mol_type = protein
                       organism = synthetic construct
SEQUENCE: 77
YMAP                                                                4

SEQ ID NO: 78          moltype = AA  length = 4
FEATURE                Location/Qualifiers
REGION                 1..4
                       note = Synthetic
source                 1..4
                       mol_type = protein
                       organism = synthetic construct
SEQUENCE: 78
YMNL                                                                4

SEQ ID NO: 79          moltype = AA  length = 4
FEATURE                Location/Qualifiers
REGION                 1..4
                       note = Synthetic
source                 1..4
                       mol_type = protein
                       organism = synthetic construct
SEQUENCE: 79
YMPM                                                                4

SEQ ID NO: 80          moltype = AA  length = 4
FEATURE                Location/Qualifiers
REGION                 1..4
                       note = Synthetic
source                 1..4
                       mol_type = protein
                       organism = synthetic construct
SEQUENCE: 80
YMSM                                                                4

SEQ ID NO: 81          moltype = AA  length = 4
FEATURE                Location/Qualifiers
REGION                 1..4
                       note = Synthetic
source                 1..4
                       mol_type = protein
                       organism = synthetic construct
SEQUENCE: 81
YSNM                                                                4

SEQ ID NO: 82          moltype = AA  length = 4
FEATURE                Location/Qualifiers
REGION                 1..4
                       note = Synthetic
source                 1..4
                       mol_type = protein
                       organism = synthetic construct
SEQUENCE: 82
YTAV                                                                4

SEQ ID NO: 83          moltype = AA  length = 4
FEATURE                Location/Qualifiers
REGION                 1..4
                       note = Synthetic
source                 1..4
                       mol_type = protein
                       organism = synthetic construct
SEQUENCE: 83
YVEM                                                                4

SEQ ID NO: 84          moltype = AA  length = 4
FEATURE                Location/Qualifiers
REGION                 1..4
                       note = Synthetic
source                 1..4
                       mol_type = protein
                       organism = synthetic construct
SEQUENCE: 84
YVHV                                                                4
```

-continued

```
SEQ ID NO: 85           moltype = AA  length = 4
FEATURE                 Location/Qualifiers
REGION                  1..4
                        note = Synthetic
source                  1..4
                        mol_type = protein
                        organism = synthetic construct
SEQUENCE: 85
YVKM                                                              4

SEQ ID NO: 86           moltype = AA  length = 4
FEATURE                 Location/Qualifiers
REGION                  1..4
                        note = Synthetic
source                  1..4
                        mol_type = protein
                        organism = synthetic construct
SEQUENCE: 86
YVPM                                                              4

SEQ ID NO: 87           moltype = AA  length = 4
FEATURE                 Location/Qualifiers
REGION                  1..4
                        note = Synthetic
source                  1..4
                        mol_type = protein
                        organism = synthetic construct
SEQUENCE: 87
YANG                                                              4
```

What is claimed is:

1. A chimeric antigen receptor (CAR) comprising an extracellular antigen-binding domain, a transmembrane domain, and an intracellular signaling domain comprising a CD3ζ polypeptide and at least one co-stimulatory signaling domain that comprises a CD28 polypeptide comprising a mutated YMNM motif consisting of the amino acid sequence set forth in YSNV (SEQ ID NO: 23).

2. The CAR of claim 1, wherein the extracellular antigen-binding domain binds to an antigen.

3. The CAR of claim 2, wherein the antigen is a tumor antigen selected from the group consisting of CD19, mesothelin, AXL, TIM3, HVEM, MUC16, MUC1, CA1X, CEA, CD8, CD7, CD10, CD20, CD22, CD30, CLL1, CD33, CD34, CD38, CD41, CD44, CD49f, CD56, CD70, CD74, CD99, CD123, CD133, CD138, EGP-2, EGP-40, EpCAM, Erb-B, FBP, Fetal acetylcholine receptor, folate receptor-α, GD2, GD3, HER-2, hTERT, IL-13R-α2, κ-light chain, KDR, LeY, L1 cell adhesion molecule, MAGE-A1, MAGEA3, CT83 KK-LC-1), p53, MART1,GP100, Proteinase3 (PR1), Tyrosinase, Survivin, hTERT, EphA2, NKG2D ligands, NY-ESO-1, oncofetal antigen (h5T4), PSCA, PSMA, ROR1, TAG-72, VEGF-R2, WT-1, BCMA, CD44V6, NKCS1, EGF1R, EGFR-VIII, ADGRE2, CCR1, LILRB2, PRAME, HPV E6 oncoprotein, and HPV E7 oncoprotein.

4. The CAR of claim 1, wherein the CAR comprises the amino acid sequence set forth in SEQ ID NO: 57.

5. The CAR of claim 1, wherein the CD28 polypeptide comprises the amino acid sequence set forth in SEQ ID NO: 64.

6. The CAR of claim 1, wherein the CD3ζ polypeptide comprises the amino acid sequence set forth in SEQ ID NO: 18.

7. The CAR of claim 1, wherein the transmembrane domain comprises a transmembrane domain of a CD8 polypeptide, a CD28 polypeptide, a CD3ζ polypeptide, a CD4 polypeptide, a 4-1BB polypeptide, a OX40 polypeptide, an ICOS polypeptide, a CD84 polypeptide, a CD166 polypeptide, a CD8a polypeptide, a CD8b polypeptide, an ICAM-1 polypeptide, a CTLA-4 polypeptide, a CD27 polypeptide, a CD40 polypeptide, a NKGD2 polypeptide, or a combination thereof.

8. The CAR of claim 1 further comprising a hinge/spacer region that links the extracellular antigen-binding domain to the transmembrane domain.

9. The CAR of claim 1, wherein hinge/spacer region comprises a hinge region of a CD8 polypeptide, a CD2ζ polypeptide, a CD32 polypeptide, a 4-1BB polypeptide, a OX40 polypeptide, an ICOS polypeptide, a CD84 polypeptide, a CD166 polypeptide, a CD8a polypeptide, a CD8b polypeptide, an ICAM-1 polypeptide, a CTLA-4 polypeptide, a CD27 polypeptide, a CD40 polypeptide, a NKGD2 polypeptide, or a combination thereof.

10. The CAR of claim 1, wherein the CD28 polypeptide consists of the amino acid sequence set forth in SEQ ID NO: 64.

11. A method for producing an antigen-specific cell, the method comprising introducing into a cell a nucleic acid molecule encoding a CAR of claim 1.

12. A nucleic acid molecule encoding the CAR of claim 1.

13. A vector comprising the nucleic acid molecule of claim 12.

14. A host cell expressing the nucleic acid molecule of claim 12.

15. A kit comprising a CAR of claim 1.

16. A nucleic acid molecule encoding the CAR of claim 1 comprising the nucleotide sequence set forth in SEQ ID NO:58.

17. An immunoresponsive cell comprising the CAR of claim 1.

18. The immunoresponsive cell of claim 17, wherein the cell is a cell of the lymphoid lineage, a cell of the myeloid lineage, a T cell, a Natural Killer (NK) cell, or a stem cell from which lymphoid cells may be differentiated.

19. The immunoresponsive cell of claim 17, wherein the immunoresponsive cell is a T cell.

20. The immunoresponsive cell of claim 19, wherein the T cell is selected from the group consisting of a cytotoxic T lymphocyte (CTL), a γδ T cell, a tumor-reactive lymphocyte, a tumor-infiltrating lymphocyte (TIL), a regulatory T cell, and a Natural Killer T (NKT) cell.

21. A composition comprising the immunoresponsive cell of claim 17.

22. A method of reducing tumor burden in a subject, treating a neoplasm or a tumor, and/or lengthening survival of a subject having a neoplasm or a tumor, the method comprising administering to the subject the cell of claim 17 or a composition thereof.

23. The method of claim 22, wherein the method reduces the number of tumor cells, reduces tumor size, and/or eradicates the tumor in the subject.

24. The method of claim 22, wherein the neoplasm and/or tumor is selected from the group consisting of B cell leukemia, B cell lymphoma, acute lymphoblastic leukemia (ALL), chronic lymphocytic leukemia (CLL), non-Hodgkin's lymphoma, Burkitt lymphoma, acute myeloid leukemia (AML) and Mixed-phenotype acute leukemia (MPAL).

25. The immunoresponsive cell of claim 17, said cell further comprising an exogenous IL-18 polypeptide, an exogenous IL-33 polypeptide, an exogenous IL-36 polypeptide, or an exogenous CD40L polypeptide.

26. The immunoresponsive cell of claim 17, said cell further comprising an exogenous IL-18 polypeptide.

27. A composition comprising the immunoresponsive cell of claim 26.

28. A method of reducing tumor burden in a subject, treating a neoplasm or a tumor, and/or lengthening survival of a subject having a neoplasm or a tumor, the method comprising administering to the subject the cell of claim 26 or a composition thereof.

* * * * *